United States Patent
Kokkotou

(10) Patent No.: US 10,458,996 B1
(45) Date of Patent: Oct. 29, 2019

(54) METHODS FOR DETERMINING CLINICAL RESPONSE TO TNF-ALPHA AND/OR JAK INHIBITORS IN SUBJECTS WITH INFLAMMATORY DISEASES

(71) Applicant: Beth Israel Deaconess Medical Center, Inc., Boston, MA (US)

(72) Inventor: Efi Kokkotou, Chestnut Hill, MA (US)

(73) Assignee: Beth Israel Deaconess Medical Center, Inc., Boston, MA (US)

( * ) Notice: Subject to any disclaimer, the term of this patent is extended or adjusted under 35 U.S.C. 154(b) by 0 days.

(21) Appl. No.: 15/601,509

(22) Filed: May 22, 2017

Related U.S. Application Data

(60) Provisional application No. 62/339,678, filed on May 20, 2016.

(51) Int. Cl.

| | |
|---|---|
| *G01N 33/68* | (2006.01) |
| *G01N 33/50* | (2006.01) |
| *A61K 39/00* | (2006.01) |
| *C07K 16/24* | (2006.01) |
| *A61K 39/395* | (2006.01) |
| *A61K 31/519* | (2006.01) |
| *C07K 16/28* | (2006.01) |

(52) U.S. Cl.
CPC ....... *G01N 33/6863* (2013.01); *A61K 31/519* (2013.01); *A61K 39/39575* (2013.01); *C07K 16/241* (2013.01); *C07K 16/2839* (2013.01); *G01N 33/5023* (2013.01); *G01N 33/6869* (2013.01); *A61K 2039/505* (2013.01); *C07K 2317/24* (2013.01); *G01N 2800/065* (2013.01)

(58) Field of Classification Search
CPC .......... G01N 33/5023; G01N 33/6863; G01N 33/6869; G01N 2800/065; C07K 16/2839; C07K 16/241; C07K 2317/24; A61K 31/519; A61K 39/39575; A61K 2039/505
See application file for complete search history.

(56) References Cited

PUBLICATIONS

Tsilingiri K, et al. (2013) J. Vis. Exp. 75:4368. http://dx.doi.org/10.3791/4368.*
Tracey D, et al. (Feb. 2008) Pharmacol Ther. 117(2):244-79. DOI:10.1016/j.pharmthera.2007.10.001. Epub Oct. 26, 2007.*
Rismo R, et al. (May 2012) Scand J Gastroenterol. 47(5):538-47. DOI:10.3109/00365521.2012.667146.*
Iskandar HN, et al. (Apr. 2012) Transl Res. 159(4):313-25. DOI:10.1016/j.trsl.2012.01.001. Epub Feb. 1, 2012.*
Umehara Y, et al. (Nov.-Dec. 2006) Hepatogastroenterology. 53(72):879-82.*
Muzes G, et al. (Nov. 7, 2012) World J Gastroenterol. 18(41):5848-5861. DOI:10.3748/wjg.v18.i41.5848.*

Aggarwal et al., Historical perspectives on tumor necrosis factor and its superfamily: 25 years later, a golden journey. Blood. Jan. 19, 2012;119(3):651-65.
Ahluwalia et al., Immunopathogenesis of inflammatory bowel disease and mechanisms of biological therapies. Scand J Gastroenterol. Apr. 2018;53(4):379-389.
Aittomaki et al., Therapeutic targeting of the Jak/STAT pathway. Basic Clin Pharmacol Toxicol. Jan. 2014;114(1):18-23.
Algaba et al., The effects of infliximab or adalimumab on vascular endothelial growth factor and angiopoietin 1 angiogenic factor levels in inflammatory bowel disease: serial observations in 37 patients. Inflamm Bowel Dis. Apr. 2014;20(4):695-702.
Allen et al., Review article: moving towards common therapeutic goals in Crohn's disease and rheumatoid arthritis. Aliment Pharmacol Ther. Apr. 2017;45(8):1058-1072.
Alonzi et al., Induced somatic inactivation of STAT3 in mice triggers the development of a fulminant form of enterocolitis. Cytokine. Apr. 21, 2004;26(2):45-56.
Arias et al., A panel to predict long-term outcome of infliximab therapy for patients with ulcerative colitis. Clin Gastroenterol Hepatol. Mar. 2015;13(3):531-8.
Arijs et al., Mucosal gene signatures to predict response to infliximab in patients with ulcerative colitis. Gut. Dec. 2009;58(12):1612-9.
Arijs et al., Predictive value of epithelial gene expression profiles for response to infliximab in Crohn's disease. Inflamm Bowel Dis. Dec. 2010;16(12):2090-8.
Atreya et al., IBD pathogenesis in 2014: Molecular pathways controlling barrier function in IBD. Nat Rev Gastroenterol Hepatol. Feb. 2015;12(2):67-8.
Atreya et al., In vivo imaging using fluorescent antibodies to tumor necrosis factor predicts therapeutic response in Crohn's disease. Nat Med. Mar. 2014;20(3):313-8.
Banks et al., Associations between functional polymorphisms in the NF?B signaling pathway and response to anti-TNF treatment in Danish patients with inflammatory bowel disease. Pharmacogenomics J. Dec. 2014;14(6):526-34.
Boland et al., Update on Janus kinase antagonists in inflammatory bowel disease. Gastroenterol Clin North Am. Sep. 2014;43(3):603-17.
Caruso et al., A functional role for interleukin-21 in promoting the synthesis of the T-cell chemoattractant, MIP-3alpha, by gut epithelial cells. Gastroenterology. Jan. 2007;132(1):166-75.

(Continued)

*Primary Examiner* — Robert S Landsman
(74) *Attorney, Agent, or Firm* — McCarter & English, LLP; Thomas O. Hoover; Yu Lu

(57) ABSTRACT

Embodiments of the present invention relate to biomarkers, including signatures containing a plurality of such biomarkers, which are predictive of responsiveness to therapy of gastrointestinal inflammatory disorders such as inflammatory bowel diseases (IBD), e.g., ulcerative colitis and Crohn's disease, with TNFα inhibitors or JAK-STAT inhibitors, such as anti-TNFα antibodies and JAK inhibitors. Further embodiments relate to the use of such biomarkers and/or signatures in determining the responsiveness of a patient with IBD to therapy with TNFα inhibitors or JAK inhibitors, such as anti-TNFα antibodies or small molecule JAK inhibitors. Additional embodiments relate to methods of treating gastrointestinal inflammatory disorders in patients, based on detection of one or more biomarkers.

20 Claims, 11 Drawing Sheets

(56) References Cited

PUBLICATIONS

Chang et al., Studies in human intestinal tissues: is it time to reemphasize research in human immunology? Gastroenterology. Jul. 2014;147(1):26-30.

Clark et al., Discovery and development of Janus kinase (JAK) inhibitors for inflammatory diseases. J Med Chem. Jun. 26, 2014;57(12):5023-38.

Coskun et al., Involvement of JAK/STAT signaling in the pathogenesis of inflammatory bowel disease. Pharmacol Res. Oct. 2013;76:1-8.

Costa et al., Development of a 3D printed device to support long term intestinal culture as an alternative to hyperoxic chamber methods. 3D Print Med. 2017;3(1):9. 5 pages.

Couch et al., Cannabidiol and Palmitoylethanolamide are anti-inflammatory in the acutely inflamed human colon. Clinical Science. Pre-publication edition. 36 pages, DOI 10.1042/CS20171288, (2017).

Danese et al., JAK inhibition using tofacitinib for inflammatory bowel disease treatment: a hub for multiple inflammatory cytokines. Am J Physiol Gastrointest Liver Physiol. Feb. 1, 2016;310(3):G155-62.

Danese, Mechanisms of action of infliximab in inflammatory bowel disease: an anti-inflammatory multitasker. Dig Liver Dis. Jul. 2008;40 Suppl 2:S225-8.

Di Sabatino et al., Blockade of transforming growth factor beta upregulates T-box transcription factor T-bet, and increases T helper cell type 1 cytokine and matrix metalloproteinase-3 production in the human gut mucosa. Gut. May 2008;57(5):605-12.

Drew et al., Molecular Profiling of Multiplexed Gene Markers to Assess Viability of Ex Vivo Human Colon Explant Cultures. Biores Open Access. Nov. 1, 2015;4(1):425-30.

Edwards et al., Preclinical target validation using patient-derived cells. Nat Rev Drug Discov. Mar. 2015;14(3):149-50.

Feagan, Update on Tofacitinib for Inflammatory Bowel Disease. Gastroenterol Hepatol (N Y). Sep. 2016;12(9):572-574.

Fina et al., Monteleone G. Interleukin-25 production is differently regulated by TNF-a and TGF-β1 in the human gut. Mucosal Immunol. Mar. 2011;4(2):239-44.

Gerich et al., Towards personalized care in IBD. Nat Rev Gastroenterol Hepatol. May 2014;11(5):287-99.

Ghoreschi et al., Modulation of innate and adaptive immune responses by tofacitinib (CP-690,550). J Immunol. Apr. 1, 2011;186(7):4234-43.

Harvey et al., Cannabinoid CB2 receptor activation attenuates cytokine-evoked mucosal damage in a human colonic explant model without changing epithelial permeability. Cytokine. Aug. 2013;63(2):209-17.

Harvey et al., Interleukin 17A evoked mucosal damage is attenuated by cannabidiol and anandamide in a human colonic explant model. Cytokine. Feb. 2014;65(2):236-44.

Hlavaty et al., Polymorphisms in apoptosis genes predict response to infliximab therapy in luminal and fistulizing Crohn's disease. Aliment Pharmacol Ther. Oct. 1, 2005;22(7):613-26.

Huff et al., Extracellular matrix-associated cytokines regulate CD4+ effector T-cell responses in the human intestinal mucosa. Mucosal Immunol. Jul. 2011;4(4):420-7.

Jarry et al., Interferon-Alpha Promotes Th1 Response and Epithelial Apoptosis via Inflammasome Activation in Human Intestinal Mucosa. Cell Mol Gastroenterol Hepatol. Sep. 20, 2016;3(1):72-81.

Jarry et al., Loss of interleukin-10 or transforming growth factor beta signaling in the human colon initiates a T-helper 1 response via distinct pathways. Gastroenterology. Nov. 2011;141(5):1887-96.e1-2.

Jarry et al., Mucosal IL-10 and TGF-beta play crucial roles in preventing LPS-driven, IFN-gamma-mediated epithelial damage in human colon explants. J Clin Invest. Mar. 2008;118(3):1132-42.

Jones et al., Profiling drugs for rheumatoid arthritis that inhibit synovial fibroblast activation. Nat Chem Biol. Jan. 2017;13(1):38-45.

Jurgens et al., Levels of C-reactive protein are associated with response to infliximab therapy in patients with Crohn's disease. Clin Gastroenterol Hepatol. May 2011;9(5):421-7.e1.

Karaman et al., A quantitative analysis of kinase inhibitor selectivity. Nat Biotechnol. Jan. 2008;26(1):127-32.

Koon et al., Human monoclonal antibodies against Clostridium difficile toxins A and B inhibit inflammatory and histologic responses to the toxins in human colon and peripheral blood monocytes. Antimicrob Agents Chemother. Jul. 2013;57(7):3214-23.

Kornbluth et al., Ulcerative colitis practice guidelines in adults: American College of Gastroenterology, Practice Parameters Committee. Am J Gastroenterol. Mar. 2010;105(3):501-23.

Kubo et al., The JAK inhibitor, tofacitinib, reduces the T cell stimulatory capacity of human monocyte-derived dendritic cells. Ann Rheum Dis. Dec. 2014;73(12):2192-8.

Lacruz-Guzman et al., Influence of polymorphisms and TNF and IL1beta serum concentration on the infliximab response in Crohn's disease and ulcerative colitis. Eur J Clin Pharmacol. Mar. 2013;69(3):431-8.

Leal et al., Identification of inflammatory mediators in patients with Crohn's disease unresponsive to anti-TNFa therapy. Gut. Feb. 2015;64(2):233-42.

Li et al., Inter-individual variability and genetic influences on cytokine responses to bacteria and fungi. Nat Med. Aug. 2016;22(8):952-60.

Llopis et al., Lactobacillus casei downregulates commensals' inflammatory signals in Crohn's disease mucosa. Inflamm Bowel Dis. Feb. 2009;15(2):275-83.

Lopetuso et al., Can We Predict the Efficacy of Anti-TNF-a Agents? Int J Mol Sci. Sep. 14, 2017;18(9). 17 pages.

Lowenberg et al., Next-Generation Therapeutics for IBD. Curr Gastroenterol Rep. Jun. 2015;17(6):21. 8 pages.

Maeshima et al., The JAK inhibitor tofacitinib regulates synovitis through inhibition of interferon—? and interleukin-17 production by human CD4+ T cells. Arthritis Rheum. Jun. 2012;64(6):1790-8.

Magnusson et al., Cultured blood T-cell responses predict anti-TNF therapy response in patients with ulcerative colitis. Aliment Pharmacol Ther. Jun. 2015;41(11):1149-61.

Magnusson et al., Response to infliximab therapy in ulcerative colitis is associated with decreased monocyte activation, reduced CCL2 expression and downregulation of Tenascin C. J Crohns Colitis. Jan. 2015;9(1):56-65.

Marafini et al., CCL20 Is Negatively Regulated by TGF-β1 in Intestinal Epithelial Cells and Reduced in Crohn's Disease Patients With a Successful Response to Mongersen, a Smad7 Antisense Oligonucleotide. J Crohns Colitis. May 1, 2017;11(5):603-609.

Meijer et al., Effect of the anti-tumor necrosis factor-alpha antibody infliximab on the ex vivo mucosal matrix metalloproteinase-proteolytic phenotype in inflammatory bowel disease. Inflamm Bowel Dis. Feb. 2007;13(2):200-10.

Meyer et al., Anti-inflammatory activity and neutrophil reductions mediated by the JAK1/JAK3 inhibitor, CP-690,550, in rat adjuvant-induced arthritis. J Inflamm (Lond). Aug. 11, 2010;7:41. 12 pages.

Migita et al., Inhibition of Janus kinase/signal transducer and activator of transcription (JAK/STAT) signalling pathway in rheumatoid synovial fibroblasts using small molecule compounds. Clin Exp Immunol. Dec. 2013;174(3):356-63.

Migita et al., Inhibitory effects of the JAK inhibitor CP690,550 on human CD4(+) T lymphocyte cytokine production. BMC Immunol. Aug. 31, 2011;12:51. 10 pages.

Mitroulis et al., Leukocyte integrins: role in leukocyte recruitment and as therapeutic targets in inflammatory disease. Pharmacol Ther. Mar. 2015;147:123-135.

Molander et al., Fecal calprotectin concentration predicts outcome in inflammatory bowel disease after induction therapy with TNFa blocking agents. Inflamm Bowel Dis. 7 pages, pre-publication edition. (2012).

Monteleone et al., Blocking Smad7 restores TGF-beta1 signaling in chronic inflammatory bowel disease. J Clin Invest. Aug. 2001;108(4):601-9.

Montero-Melendez et al., Identification of novel predictor classifiers for inflammatory bowel disease by gene expression profiling. PLoS One. Oct. 14, 2013;8(10):e76235. 9 pages.

(56) References Cited

PUBLICATIONS

Moodley et al., Network pharmacology of JAK inhibitors. Proc Natl Acad Sci U S A. Aug. 30, 2016;113(35):9852-7.
Neurath et al., Current and emerging therapeutic targets for IBD. Nat Rev Gastroenterol Hepatol. May 2017;14(5):269-278.
Neurath, New targets for mucosal healing and therapy in inflammatory bowel diseases. Mucosal Immunol. Jan. 2014;7(1):6-19.
Olivera et al., JAK inhibition in inflammatory bowel disease. Expert Rev Clin Immunol. Jul. 2017;13(7):693-703.
Olsen et al., TNF-alpha gene expression in colorectal mucosa as a predictor of remission after induction therapy with infliximab in ulcerative colitis. Cytokine. May 2009;46(2):222-7.
Paul et al., How to improve R&D productivity: the pharmaceutical industry's grand challenge. Nat Rev Drug Discov. Mar. 2010;9(3):203-14.
Petito et al., Direct effect of infliximab on intestinal mucosa sustains mucosal healing: exploring new mechanisms of action. Dig Liver Dis. Apr. 2016;48(4):391-8.
Philippe et al., Mu opioid receptor expression is increased in inflammatory bowel diseases: implications for homeostatic intestinal inflammation. Gut. Jun. 2006;55(6):815-23.
Pierik et al., Tumour necrosis factor-alpha receptor 1 and 2 polymorphisms in inflammatory bowel disease and their association with response to infliximab. Aliment Pharmacol Ther. Aug. 1, 2004;20(3):303-10.
Piscianz et al., Fate of lymphocytes after withdrawal of tofacitinib treatment. PLoS One. Jan. 9, 2014;9(1):e85463. 8 pages.
Pritchard et al., Making better drugs: Decision gates in non-clinical drug development. Nat Rev Drug Discov. Jul. 2003;2(7):542-53.
Rosengren et al., The JAK inhibitor CP-690,550 (tofacitinib) inhibits TNF-induced chemokine expression in fibroblast-like synoviocytes: autocrine role of type I interferon. Ann Rheum Dis. Mar. 2012;71(3):440-7.
Sandborn et al., Anti-CD3 antibody visilizumab is not effective in patients with intravenous corticosteroid-refractory ulcerative colitis. Gut. Nov. 2010;59(11):1485-92.
Sandborn et al., Tofacitinib as Induction and Maintenance Therapy for Ulcerative Colitis. N Engl J Med. May 4, 2017;376(18)1723-1736.
Sandborn et al., Tofacitinib, an oral Janus kinase inhibitor, in active ulcerative colitis. N Engl J Med. Aug. 16, 2012;367(7):616-24.
Sands, New drugs on the horizon for IBD. Dig Dis. 2014;32 Suppl 1:74-81.
Semerano et al., Developments with investigational Janus kinase inhibitors for rheumatoid arthritis. Expert Opin Investig Drugs. Dec. 2016;25(12):1355-1359.
Singh et al., Chemokine and cytokine levels in inflammatory bowel disease patients. Cytokine. Jan. 2016;77:44-9.
Strittmatter, Overcoming Drug Development Bottlenecks With Repurposing: Old drugs learn new tricks. Nat Med. Jun. 2014;20(6):590-1.
Strober et al., Proinflammatory cytokines in the pathogenesis of inflammatory bowel diseases. Gastroenterology. May 2011;140(6):1756-1767.
Takeda et al., Enhanced Th1 activity and development of chronic enterocolitis in mice devoid of Stat3 in macrophages and neutrophils. Immunity. Jan. 1999;10(1):39-49.
Te Velde et al., Comparative analysis of colonic gene expression of three experimental colitis models mimicking inflammatory bowel disease. Inflamm Bowel Dis. Mar. 2007;13(3):325-30.
Telliez et al., Discovery of a JAK3-Selective Inhibitor: Functional Differentiation of JAK3-Selective Inhibition over pan-JAK or JAK1-Selective Inhibition. ACS Chem Biol. Dec. 16, 2016;11(12):3442-3451.
Terciolo et al., *Saccharomyces boulardii* CNCM I-745 Restores intestinal Barrier Integrity by Regulation of E-cadherin Recycling. J Crohns Colitis. Aug. 1, 2017;11(8):999-1010. 12 pages.
Thorarensen et al., ATP-mediated kinome selectivity: the missing link in understanding the contribution of individual JAK Kinase isoforms to cellular signaling. ACS Chem Biol. Jul. 18, 2014;9(7)1552-8.
Tsilingiri et al., Probiotic and postbiotic activity in health and disease: comparison on a novel polarised ex-vivo organ culture model. Gut. Jul. 2012;61(7):1007-15.
Tsilingiri et al., Should probiotics be tested on ex vivo organ culture models? Gut Microbes. Sep.-Oct. 2012;3(5):442-8.
Vandussen et al., Development of an enhanced human gastrointestinal epithelial culture system to facilitate patient-based assays. Gut. Jun. 2015;64(6):911-20.
Vermeire et al., Etrolizumab as induction therapy for ulcerative colitis: a randomised, controlled, phase 2 trial. Lancet. Jul. 26, 2014;384(9940):309-18.
Vossenkamper et al., A CD3-specific antibody reduces cytokine production and alters phosphoprotein profiles in intestinal tissues from patients with inflammatory bowel disease. Gastroenterology. Jul. 2014;147(1):172-83.
Wehling, Assessing the translatability of drug projects: what needs to be scored to predict success? Nat Rev Drug Discov. Jul. 2009;8(7):541-6.
Weiser et al., Molecular classification of Crohn's disease reveals two clinically relevant subtypes. Gut. Jan. 2018;67(1):36-42.
Wildenberg et al., A major advance in ex vivo intestinal organ culture. Gut. Jul. 2012;61(7):961-2.
Willson et al., Deletion of intestinal epithelial cell STAT3 promotes T-lymphocyte STAT3 activation and chronic colitis following acute dextran sodium sulfate injury in mice. Inflamm Bowel Dis. Mar. 2013;19(3):512-25.
Yamamoto-Furusho, Inflammatory bowel disease therapy: blockade of cytokines and cytokine signaling pathways. Curr Opin Gastroenterol. Jul. 2018;34(4):187-193.
Yarilina et al., Regulation of inflammatory responses in tumor necrosis factor-activated and rheumatoid arthritis synovial macrophages by JAK inhibitors. Arthritis Rheum. Dec. 2012;64(12):3856-66.

\* cited by examiner

FIG. 5A Anti-TNF (Infliximab 0.5mg/ml)
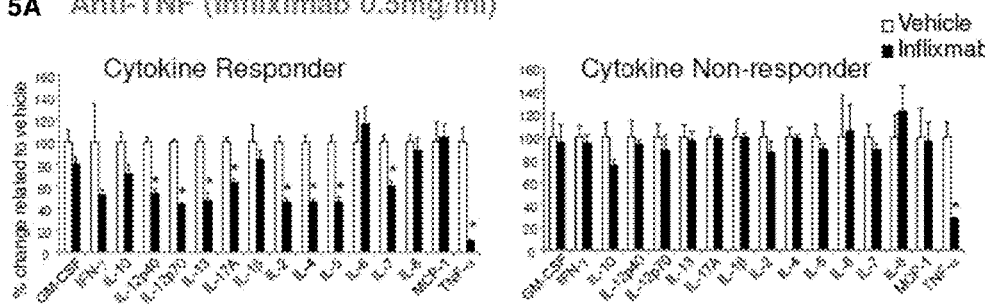
FIG. 5B JAK inhibitor (tofacitinib 100μM)
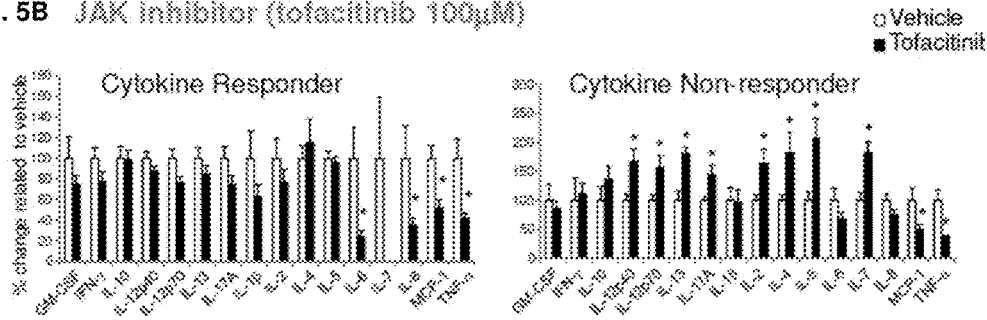
FIG. 5C Experimental drug (ED 10μM)
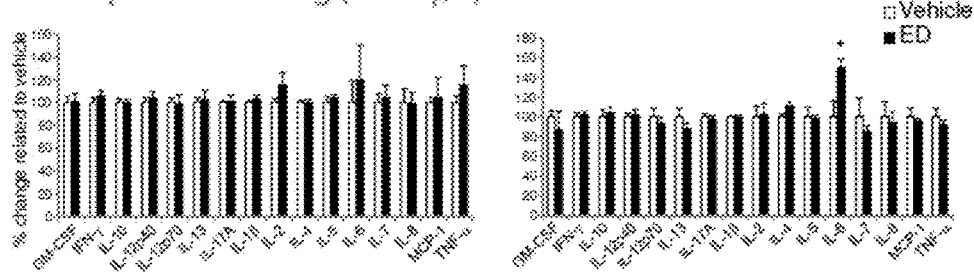

Anti-TNFα (Infliximab - patient ID 13-384)

JAK Inhibitor (tofacitinib - patient ID 13-394)

Anti-Integrin Antibody (vedolizumab - patient ID 130562)

Drug A (small molecule GPCR antagonist - patient ID 13-426)

Drug B (small molecule protease inhibitor - patient ID 13-445)

METHODS FOR DETERMINING CLINICAL RESPONSE TO TNF-ALPHA AND/OR JAK INHIBITORS IN SUBJECTS WITH INFLAMMATORY DISEASES

REFERENCE TO RELATED APPLICATIONS

This application claims the benefit of the filing date under 35 U.S.C. § 119(e) to U.S. Provisional Application No. 62/339,678, filed on May 20, 2016, the entire content of which is incorporated herein by reference.

FIELD OF THE INVENTION

Embodiments provided herein relate to assay methods, modules, and kits for conducting diagnostic assays for inflammatory diseases.

BACKGROUND OF THE INVENTION

Inflammatory Bowel Disease (IBD) is presented in two main forms, Crohn's Disease (CD) or Ulcerative Colitis (UC) and can last for more than 20 years, with periods of remissions and relapses, for which there are treatment options but no cure.

The proportion of patients with CD vs. UC varies geographically, with a reported prevalence of 100-200 per 100,000 for UC and 50-100 per 100,000 for CD in western societies. In the U.S. alone, IBD affects 1.6 million Americans (among them 80,000 children) and as many as 75,000 news cases are diagnosed every year. In fact, it appears that the problem has been overly underestimated. A more recent survey indicated that 3.1 million Americans reported a diagnosis of IBD in year 2015.

The impact of the disease to society is disproportionally high, since the majority of patients are diagnosed before the age of 35. Often, disease symptoms like abdominal pain and cramps, urgency, bloody diarrhea, fatigue and weight loss are precipitated under psychological stress and severely compromise the patient's quality of life. Indeed, due to their affliction, about 15% of patients with IBD cannot sustain a full time job (Carter et al., *Gut* 53 Suppl 5: v1-16, 2004). In addition to frequent hospitalizations, more than half of the patients with IBD require some type of surgical intervention during their lifetime, despite the introduction recently of biological therapies that have revolutionized the medical management of IBD.

Part of the problem that hampers the development of effective treatments for IBD is that disease etiology remains unclear. The current prevailing notion is that an inappropriate activation of the mucosal immune response to intestinal microbiome in genetically predisposed individuals leads to local invasion of effector immune cells, unbalanced production of cytokines and chronic tissue injury (Abraham et al., *Pharmacol Ther* 117:244-279, 2008).

One of the prominent cytokines secreted during the process is TNFα. TFNα can be produced by different immune and non-immune cell types including macrophages, T-cells, granulocytes, NK cells, fibroblasts and smooth muscle cells in a form of a soluble cytokine (sTNF) or a cell surface bound precursor (tmTNF) (Tracey et al., *Pharmacol Ther* 117:244-279, 2008; Aggarwal et al., *Blood* 119:651-665). Both TNF forms are biologically active and interact with two distinct receptors, TNFR1 and TNFR2; of them TNFR1 is rather ubiquitously expressed while TNFR2 is inducible on hematopoietic and endothelial cells. sTNFα favors signaling via TNFR1 and the NFκB pathway while mTNF generally stimulates cells via TNFR2. TNFα expression can be triggered by diverse stimuli including bacteria, viruses, immune complexes, cytokines (IL-1β, IL-17A, IFNγ, GM-CSF) as well as tissue hypoxia or trauma (Tracey et al., 2008). Therefore, while under homeostatic responses TNFα plays an important role in host defense against intracellular bacteria (*Mycobacterium* or *Listeria*) and malignant cells, unbalanced TNFα activity has been implicated in the pathogenesis not only of IBD but also of rheumatoid arthritis, psoriasis and ankylosing spondylitis (Aggarwal et al., 2012).

Ongoing research on the complex biology of TNFα has uncovered several mechanisms by which TNFα modulates inflammation and matrix destruction in these diseases. TNF receptor signaling promotes activation of proinflammatory pathways or apoptosis, depending on the metabolic state of the cell (Brenner et al., *Nat Rev Immunol* 15:362-374, 2015; Pimentel-Muinos et al., *Immunity* 11:783-793, 1999). In several target cells, TNFα stimulates the production of cytokines such as IL-1β, IFNγ, IL-6 and IL-2, which in turn can act as TNFα inducers, as well as some negative feedback regulators like IL-10 and PGE2 (Tracey et al., 2008).

Current medical management for IBD aims to relieve symptomatology and improve the patient's quality of life. Patients can initially be treated with corticosteroids, aminosalicylates (sulfasalazine, mesalamine), and immunomodulators (azathioprine, 6-mercaptopurine, methoxetrate), followed by biologic therapies like anti-TNFα (infliximab, adalimumab, certolizumab, golimumab).

TNFα antagonists like infliximab, adalimumab, golimumab and certolizumab pegol are humanized or human/mouse chimeric antibodies (infliximab) to TNFα, and are parentally administered protein therapeutics (biologics). For example, infliximab (Remicade) is a chimeric mouse/human monoclonal antibody against TNFα with an indication for the treatment of moderately to severely active CD or UC in patients who have not responded well to the more conventional therapies. The current therapeutic scheme for infliximab is three doses (usually 5 mg/kg) of induction (week 0, 2 and 6) followed by maintenance therapy every 8 weeks. The exact mechanisms of action of these drugs in IBD remain largely unknown (Oikonomopoulos et al., *Curr Drug Targets* 14:1421-1432, 2013).

The introduction of the anti-TNFα antibodies to IBD treatment has revolutionized the field of IBD therapeutics. Indeed, in the past, 70%-80% of patients with CD would require some form of surgical intervention during their lifetime and up to one third of patients with UC would be subjected to colectomy.

TNFα blockers have improved symptomatology in a significant percentage of patients with IBD (Colombel et al., *N Engl J Med* 362:1383-1395, 2010; Rutgeerts et al., *N Engl J Med* 353:2462-2476, 2005). Primary response rates to induction therapy with infliximab are up to 60% in randomized clinical trials of CD and UC while placebo responses range from 25-35% (Papamichael et al., *Inflamm Bowel Dis* 21:182-197, 2015).

However, only a fraction of IBD patients commenced on anti-TNFα treatment achieve clinical remission; and about half of the patients who initially benefit the treatment will lose response within 1 year of maintenance therapy. For example, sustained response rates beyond week 30 are substantially lower (30-40% infliximab versus 15-25% placebo treatment), and are comparable between the different anti-TNFα biologics, leaving a concerning number of IBD patients with active disease (Sands et al., Dig Dis 32 Suppl 1:74-81, 2014). While it has become well accepted that secondary loss of response to infliximab is mainly due to the development in 10% of patients of anti-drug antibodies (ADA) which might directly block drug activity or enhance its clearance, the causes of primary non-response are less clear and might be attributed to inadequate dosing, drug pharmacokinetics, the patient's genetic make-up but also to a non-TNF-driven disease (Papamichael et al., 2015).

The beneficial effect of anti-TNFα treatment appears to be overestimated when patient-reported outcomes are used, since those have been linked with higher drug and placebo responses. In the ACT1 study that examined the efficacy of infliximab in UC, clinical response rates during induction with 10 mg/kg of infliximab (week 8) were 61.5% (vs 37.2% in placebo), and dropped to 19.8% at week 53 of maintenance therapy (1 vs 9.8% in placebo). The association between serum infliximab levels and efficacy has been evaluated in many studies and it is well accepted now that therapeutic drug monitoring and adjustment of the drug dose can further improve therapeutic outcomes.

Several factors can contribute to low infliximab levels. For example, in severe UC, high CRP and TNF and low albumin and hemoglobin levels, have been associated with more rapid drug clearance and increased drug leakage in the stool. One of the main reasons of low drug levels is the development of anti-drug antibodies (ADA) which can accelerate drug clearance through the reticuloendothelial system. Evaluation of 483 patients with CD during maintenance therapy has shown that 23% of patients had undetectable infliximab serum levels; of those 72% were positive for anti-drug antibodies (ADA). A recent metanalysis estimated a 3.2-fold risk (95% CI:2-4.9) to loose response to infliximab in the presence of ADA. Moreover, the presence of ADA almost doubles the risk for acute reactions following drug infusion often resulting in drug discontinuation. The addition of an immunomodulator such as azathioprine to anti-TNF therapy has been shown to reduce the incidence of ADA (38% in monotherapy vs 22% in combined therapy). In the SONIC trial, 508 patients with moderate-to-severe CD were randomized to receive azathioprine, infliximab, or the two drugs combined. Mucosal healing rates at week 24 of intervention were 16.5% vs 30.1% vs 43.9%, respectively.

These results clearly indicate that even under optimized treatment conditions, a significant percentage of patients with IBD can remain unresponsive to anti-TNF therapy. As a result, there is increasing pressure from stakeholders to develop new and more effective treatments for IBD and with fewer side effects.

In addition to a severe unmet need for more effective treatments in IBD, there is also a significant unmet need for personalized treatments in IBD.

Specifically, regarding long term safety, several studies attempted to quantify the risks associated with anti-TNF treatment with mixed results so far, primarily due to concomitant or previous patient exposure to immunosuppressants. Blocking TNFα, an important pathway in host defense, might reduce the patient's ability to fight infections, especially in older individuals, or increase susceptibility to certain cancers (hepatosplenic T-cell or other non-Hodgkin's lymphomas, non-melanoma skin cancer) in younger individuals. The FDA has already issued a black box warning for infliximab about "tuberculosis and additional serious opportunistic infections such as histoplasmosis, listeriosis and pneumocystosis."

Thus it has become increasingly apparent that "one size does not fit all" in IBD therapeutics. Following the FDA approval of newest therapies for IBD, like vedolizumab (Entyvio, May 2014), an antibody against alpha4beta7 integrin that blocks lymphocyte trafficking, and ustekinumab (Stelara, September 2016), an antibody against the common p40 subunit of IL-12 and IL-23, it is becoming even more urgent to identify those IBD patients who are less likely to benefit from an anti-TNFα treatment and offer them alternative options, while sparing them for potential health risks associated with ineffective therapies.

In fact, "imprecision medicine" is not restricted to IBD. A recent analysis estimates that for the ten highest-grossing drugs in the US (including three anti-TNFα drugs), for every person they do help, they fail to improve the clinical condition of 3-24 patients. Besides poor clinical outcomes, imprecision medicine has a tremendous impact on health care costs, since waste therapies can account for up to 30% of health care spending.

Thus it becomes imperative to identify among patients with IBD those whose disease is not TNFα dependent, since these individuals are not good candidates for treatment with anti-TNFα.

For example, infliximab therapy requires hospital infusions which are quite uncomfortable for some patients while in others may trigger allergic reactions or flu-like symptoms further diminishing the patient's quality of life (Hansel et al., *Nat Rev Drug Discov* 9:325-338, 2010). Most importantly, and particularly for the pediatric IBD population, anti-TNFα treatments have been associated with rare but life threatening adverse effects, including opportunistic infections, demyelinating disease and certain malignancies (Lichtenstein et al., *Am J Gastroenterol* 107:1409-1422, 2012; Ford et al., *Am J Gastroenterol* 108:1268-1276, 2013; Bosch et al., *Nat Rev Neurol* 7:165-172, 2013; Bongartz et al., *JAMA* 295:2275-2285, 2006; Targownik et al., *Am J Gastroenterol* 108:1835-1842, 2013; Slifman et al., *Arthritis Rheum* 48:319-324, 2003).

Over the years, several biological predictors of response to anti-TNFα in IBD have been offered, including polymorphisms in TNFα and its receptors, apoptotic genes and downstream targets (Bank et al., *Pharmacogenomics J* 14:526-534, 2014; Pierik et al., *Aliment Pharmacol Ther* 20:303-310, 2004; Hlavaty et al., *Aliment Pharmacol Ther* 22:613-626, 2005); various mucosal gene expression signatures (Leal et al, 2015; Olsen et al, *Cytokine* 46:222-227, 2009; Arijs et al., Gut 58:1612-1619, 2009; Arijs et al., *Inflamm Bowel Dis* 16:2090-2098, 2010; Montero et al., *PLoS One* 8:e76235, 2013; Rismo et al., *Scand J Gastroenterol* 47:538-547, 2012); serum factors like CRP (Jurgens et al., *Clin Gastroenterol Hepatol* 9:421-427 e421, 2011; Cornillie et al., Gut 63:1721-1727, 2014) or VEGF (Algaba et al., *Inflamm Bowel Dis* 20:695-702, 2014) and fecal biomarkers (Molander et al., *Inflamm Bowel Dis* 18:2011-2017, 2012). However, none of them has found its way to the clinical practice.

On the other hand, studies have shown that patient enrichment using various biomarkers can significantly improve clinical responses to anti-TNFα therapy. For instance, using confocal endomicroscopy in combination with fluorescent adalimumab to quantify the number of TNFα positive cells in the affected mucosa (mTNF(+) cells) of 25 patients with Crohn's disease prior to initiation of treatment, Atreya et al. (*Nat Med* 20:313-318, 2014) found that patients with high numbers of mTNF(+) cells showed significantly higher short-term response rates (92%) at week 12 upon subsequent anti-TNFα therapy, as compared to patients with low amounts of mTNF(+) cells (15%) (p=0.0002). This clinical response in the former patients was sustained over a follow-up period of 1 year, and was associated with mucosal healing observed in follow-up endoscopy. In general, when patients were enriched based on a screening test, the clinical response rate rose from 52% to 92%.

The described tool appears to be a robust predictor; however, it requires advanced technology, is target specific and does not allow flexibility in testing different drugs in parallel or their combinations.

Accordingly, there is a pressing and still unmet need for utilization of new markers, which can be tied to existing therapeutic regimen, which will help maximize therapeutic benefit in responders while concomitantly reducing the risk of unnecessary exposure in subjects who are unlikely to respond. Such goals are particularly important in the context of diseases such as IBD which are characterized by wide biological variability. See, Gerich et al., *Gastroenterol Hepatol* 11:287-299, 2014.

SUMMARY OF THE INVENTION

The compositions and methods of the instant invention provide for effective tailoring of IBD therapy to patients based on ex vivo treatment of patient's diseased biopsy materials.

The present invention provides a solution to the problem of effectively treating inflammatory bowel disease (IBD) based on the analysis of changes in certain cytokines/chemokines/inflammatory mediators (biomarkers) after ex vivo treatment of the patient's sample. More specifically, embodiments of the instant invention are based on the utilization of a correlation between statistically significant changes in the expression levels of certain cytokines/chemokines/inflammatory mediators in ex vivo explant culture of samples obtained from the inflamed areas of the intestinal mucosa of IBD subjects in the presence of a potential IBD drug (e.g., a TNFα or JAK inhibitor), and clinical response rate following therapy with the IBD drug. The present invention thus provides proteomic signatures which serve as useful diagnostic markers as well as markers that can be used to monitor disease states, disease progression, and efficacy of therapeutic intervention.

Thus in one aspect, the invention provides a method of determining the number of cytokines exhibiting statistically significant down-regulation, after contacting a candidate compound with a mucosal explant culture of a biopsy from a diseased area of an inflamed intestinal mucosa from a subject having inflammatory bowel disease (IBD), the method comprising: (a) obtaining a biopsy from a macroscopically diseased area of an inflamed intestinal mucosa from a subject having inflammatory bowel disease (IBD); (b) producing a first mucosal explant culture of the biopsy in the absence of a candidate compound, and a second mucosal explant culture of the biopsy in the presence of the candidate compound; (c) comparing the expression levels of a panel of cytokines, chemokines, and inflammatory mediators relating to IBD or treatment thereof, in the supernatant of said first mucosal explant culture and the supernatant of said second mucosal explant culture; and, (d) determining the number of said cytokines, chemokines and inflammatory mediators, from said panel of cytokines, that exhibit statistically significant down-regulation after contacting the candidate compound with the second mucosal explant culture.

Another aspect of the invention provides a method of selecting two or more test compounds for combination therapy for inflammatory bowel disease (IBD) treatment, the method comprising: (a) using the above method, identifying a first candidate compound resulting in statistically significant down-regulation of a first subset of three or more of said cytokines, chemokines and inflammatory mediators; (b) using the above method, identifying a second candidate compound resulting in statistically significant down-regulation of a second subset of three or more of said cytokines, chemokines and inflammatory mediators; (c) administering an effective amount of the first candidate compound and an effective amount of the second candidate compound to the subject for combination therapy, when said first subset and said second subset of three or more of said cytokines, chemokines and inflammatory mediators are different (e.g., completely different, or with no more than 1 or 2 overlap).

Another aspect of the invention provides a method of identifying a test compounds suitable for inflammatory bowel disease (IBD) treatment, the method comprising: using the above method, identifying, from a library of test compounds, a test compound that results in statistically significant down-regulation of three or more of said cytokines, chemokines and inflammatory mediators, thereby identifying a test compounds suitable for inflammatory bowel disease (IBD) treatment. Optionally, the method further comprises administering the test compound to a test subject to determine safety, efficacy, and/or adverse event of the test compound.

Another aspect of the invention provides a method of diagnosing and treating inflammatory bowel disease (IBD) in a subject, the method comprising: (a) obtaining a biopsy from a macroscopically diseased area of an inflamed intestinal mucosa from the subject; (b) producing a first mucosal explant culture of the biopsy in the absence of a candidate compound, and a second mucosal explant culture of the biopsy in the presence of the candidate compound; (c) comparing the expression levels of a panel of cytokines, chemokines, and inflammatory mediators relating to IBD or treatment thereof, in the supernatant of said first mucosal explant culture and the supernatant of said second mucosal explant culture; (d) diagnosing the subject as being suitable for IBD treatment using the candidate compound, when three or more said cytokines, chemokines, and inflammatory mediators (or two or more cytokines, chemokines, and inflammatory mediators that are not direct target of the candidate compound), from said panel of cytokines, chemokines, and inflammatory mediators, exhibit statistically significant down-regulation after contacting the candidate compound with the second mucosal explant culture, and, (e) administering an effective amount of the candidate compound to the subject diagnosed in step (d) as being suitable for IBD treatment using the candidate compound, thereby diagnosing and treating IBD in said subject.

Another aspect of the invention provides a method of selecting a patient population sensitive to inflammatory bowel disease (IBD) treatment using a compound, the method comprising: (a) obtaining a biopsy from a macroscopically diseased area of an inflamed intestinal mucosa from a subject, from a plurality of patients that are candidates for IBD treatment; (b) producing a first mucosal explant culture of the biopsy in the absence of a compound, and a second mucosal explant culture of the biopsy in the presence of the compound; (c) comparing the expression levels of a panel of cytokines, chemokines, and inflammatory mediators relating to IBD or treatment thereof, in the supernatant of said first mucosal explant culture and the supernatant of said second mucosal explant culture; (d) selecting the subject as being suitable for IBD treatment using the compound, when three or more said cytokines, chemokines, and inflammatory mediators (or two or more said cytokines, chemokines, and inflammatory mediators that are not direct target of the candidate compound), from said panel of cytokines, chemokines, and inflammatory mediators, exhibit statistically significant down-regulation after contacting the compound with the second mucosal explant culture; and, (e) repeating steps (a)-(d) for a different subject from said plurality of patients, until a pre-determined number of subjects are selected as being suitable for IBD treatment using the compound.

In certain embodiments, the IBD is selected from the group consisting of: ulcerative colitis (UC), Crohn's disease (CD), collagenous colitis, and lymphocytic colitis. In certain embodiments, the CD is moderately to severely active Crohn's disease.

In certain embodiments, the panel of cytokines, chemokines, and inflammatory mediators comprise, consist essentially of, or consist of: interleukin 17A (IL-17A), interleukin 7 (IL-7), interleukin 5 (IL-5), interleukin 4 (IL-4) and interleukin 13 (IL-13), granulocyte macrophage colony-stimulating factor (GM-CSF), interferon gamma (IFNγ), interleukin 10 (IL-10), interleukin 12 70-kDa (IL-12p70), interleukin 12 40-kDa (IL-12p40), interleukin 1 beta (IL-1β), interleukin 2 (IL-2), interleukin 6 (IL-6), interleukin 8 (IL-8), monocyte chemoattractant protein-1 (MCP-1), and tumor necrosis factor alpha (TNFα), optionally further comprising, consisting essentially of, or consisting of one or more of: IL-3, IL-9, IL-22, IL-23, IL-25, IL-35, IL-36, IL-37, TL1A, LIGHT and TGF-beta.

In certain embodiments, the three or more cytokines, chemokines, and inflammatory mediators are at least 5, 6, or 7 cytokines.

In certain embodiments, the compound is infliximab, and the three or more cytokines, chemokines, and inflammatory mediators are IL-17A, IL-7, IL-5, IL-4 and IL-13. In certain embodiments, the compound is tofacitinib, and said three or more cytokines, chemokines, and inflammatory mediators are IL-6, IL-8, MCP-1, and TNFα.

In certain embodiments, the compound is a nucleic acid (antisense-RNA; miRNA inhibitor or mimetic); a bioactive lipid; a metabolite; a natural product; a bacteria (probiotics, or engineered) or bacterial product.

In certain embodiments, the compound is a JAK inhibitor.

In certain embodiments, the JAK inhibitor is ruxolitinib, tofacitinib (tasocitinib; CP-690550), upadacitinib (ABT-494), baricitinib (LY3009104, INCB28050), CYT387, Filgotinib (GLPG0634), lestaurtinib, pacritinib (SB1518), JSI-124, and CHZ868, or a combination thereof.

In certain embodiments, the compound is a TNFα inhibitor.

In certain embodiments, the TNFα inhibitor is an anti-TNFα antibody or an antigen-binding fragment thereof, a small molecule antagonist, anti-sense TNFα, or siRNA or miRNA targeting TNFα.

In certain embodiments, the anti-TNFα antibody comprises infliximab, adalimumab, golimumab, certolizumab pegol, a biosimilar thereof, or a combination thereof.

In certain embodiments, expression levels of the panel of cytokines, chemokines, and inflammatory mediators are determined using an assay selected from the group consisting of: enzyme-linked immuosorbent assay (ELISA), mass spectrometry (MS), immunoblotting (WB), and immunohistochemistry (IHC).

In certain embodiments, the subject is a treatment-naïve subject who has not previously undergone therapy for IBD with a biological agent.

In certain embodiments, the subject is a treatment-naïve subject who has previously undergone therapy for IBD with a steroid, an immunomodulator, or a combination thereof.

In certain embodiments, the subject has previously undergone therapy for IBD.

In certain embodiments, the subject has previously undergone therapy with an anti-TNFα antibody or antigen-binding fragment thereof, selected from the group consisting of infliximab, adalimumab, golimumab, certolizumab pegol, or an antigen-binding fragment thereof.

In certain embodiments, the subject is in remission from treatment with the anti-TNFα antibody or antigen-binding fragment thereof; or is refractory or non-responsive to the anti-TNFα antibody or antigen-binding fragment thereof.

In certain embodiments, the biopsy is obtained through an endoscopic procedure (e.g., colonoscopy or sigmoidoscopy).

In certain embodiments, the biopsy is used in said explant culture within 30 minutes of excision.

In certain embodiments, the biopsy and the explant culture thereof comprise a mixture of different intestinal cell types including epithelial cells, immune cells, and stroma cells.

In certain embodiments, the biopsy and the explant culture thereof are not stimulated or activated with an exogenous factor to promote cytokine secretion.

In certain embodiments, the biopsy is obtained from the macroscopically most diseased area(s) of the inflamed intestinal mucosa.

In certain embodiments, the biopsy is obtained from terminal ileum, ileocolonic region, or colon of the subject.

In certain embodiments, the first and second explant cultures are maintained at about 37° C. for about 18 hrs in a humidified chamber with 95% $O_2$/5% $CO_2$.

In certain embodiments, the first and second explant cultures each comprises 2, 3, 4, 5, or 6 replicas.

In certain embodiments, statistical significance (e.g., $p<0.05$) is established based on Mann-Whitney test.

Another aspect of the invention provides a method for determining whether a subject having inflammatory bowel disease (IBD) will be responsive to treatment with a tumor necrosis factor alpha (TNFα) inhibitor, comprising determining a level of one or more (e.g., 3 or more) biomarkers selected from the group consisting of interleukin 17A (IL-17A), interleukin 7 (IL-7), interleukin 5 (IL-5), interleukin 4 (IL-4) and interleukin 13 (IL-13), or a fragment thereof, in a sample obtained from the subject (e.g., ex vivo explant culture of a tissue biopsy), in the presence and absence of a TNFα inhibitor; wherein a decrease in a level of the one or more (e.g., 3 or more) biomarkers in the presence of the TNFα inhibitor as compared to a level of the one or more (e.g., 3 or more) biomarkers in the absence of the TNFα inhibitor indicates that the subject is responsive to treatment with the TNFα inhibitor, thereby determining whether a subject having IBD is responsive to treatment with the TNFα inhibitor.

In certain embodiments, the biomarkers are detected in an intestinal mucosal sample obtained from the subject.

In certain embodiments, the biomarkers are detected in a biopsy obtained from an affected area of an inflamed intestinal mucosa.

In certain embodiments, the biomarkers are detected in a blood sample, a stool sample, or an (intestinal) luminal wash obtained from the subject.

A related aspect of the invention provides a method for determining whether a subject having IBD which is selected from the group consisting of ulcerative colitis (UC), Crohn's disease (CD), collagenous colitis and lymphocytic colitis will be responsive to treatment with a TNFα inhibitor, comprising determining a level of one or more (e.g., 3 or more) biomarkers selected from the group consisting of IL-17A, IL-7, IL-5, IL-4 and IL-13, or a fragment thereof, in a sample obtained from the subject (e.g., ex vivo explant culture of a tissue biopsy), in the presence and absence of a TNFα inhibitor; wherein a decrease in a level of the one or more (e.g., 3 or more) biomarkers in the presence of the TNFα inhibitor as compared to a level of the one or more (e.g., 3 or more) biomarkers in the absence of the TNFα inhibitor indicates that the subject is responsive to treatment with the TNFα inhibitor.

Another related aspect of the invention provides a method for determining whether a subject having IBD will be responsive to treatment with a TNFα inhibitor which is an anti-TNFα antibody, or antigen-binding fragment thereof, comprising determining a level of one or more (e.g., 3 or more) biomarkers selected from the group consisting of IL-17A, IL-7, IL-5, IL-4 and IL-13, or a fragment thereof, in a sample obtained from the subject (e.g., ex vivo explant culture of a tissue biopsy), in the presence and absence of an anti-TNFα antibody or antigen-binding fragment thereof; wherein a decrease in a level of the one or more (e.g., 3 or more) biomarkers in the presence of the anti-TNFα antibody or antigen-binding fragment thereof as compared to a level of the one or more (e.g., 3 or more) biomarkers in the absence of the anti-TNFα antibody or antigen-binding fragment thereof indicates that the subject is responsive to treatment with the anti-TNFα antibody or antigen-binding fragment thereof.

In certain embodiments, the anti-TNFα antibody or antigen-binding fragment thereof is selected from the group consisting of infliximab, adalimumab, golimumab and certolizumab pegol, or antigen-binding fragment thereof, or a combination thereof.

In certain embodiment, the anti-TNFα antibody, or antigen-binding fragment thereof, is infliximab, or an antigen-binding fragment thereof.

In one embodiment, the biomarker is a protein biomarker. Thus under this embodiment, the biomarker is selected from the group consisting of IL-17A, IL-7, IL-5, IL-4 and IL-13, or a fragment thereof.

In another embodiment, the biomarker is a nucleic acid biomarker. Thus, under this embodiment, the nucleic acid biomarker is a nucleic acid which encodes IL-17A, IL-7, IL-5, IL-4 and IL-13, or a fragment thereof. For example, such nucleic acid can be mRNA extracted from the cells in the ex vivo explant culture of the patient tissue biopsy, or from exosomes released to the supernatant of such cultures.

Another aspect of the invention provides a method for determining whether a subject having IBD will be responsive to treatment with a TNFα inhibitor, comprising determining a level of one or more protein biomarkers selected from the group consisting of IL-17A, IL-7, IL-5, IL-4 and IL-13, or a fragment thereof, in a sample obtained from the subject (e.g., ex vivo explant culture of a tissue biopsy), with an assay selected from the group consisting of enzyme-linked immuosorbent assay (ELISA), mass spectrometry (MS), immunoblotting (WB) and immunohistochemistry (IHC). The protein biomarkers are determined in the presence and absence of a TNFα inhibitor; wherein a decrease in a level of the one or more (e.g., 3 or more) protein biomarkers in the presence of the TNFα inhibitor as compared to a level of the one or more (e.g., 3 or more) biomarkers in the absence of the TNFα inhibitor indicates that the subject is responsive to treatment with the TNFα inhibitor.

Another aspect of the invention provides a method for determining whether a treatment-naïve subject having IBD will be responsive to treatment with TNFα inhibitor, comprising determining a level of one or more (e.g., 3 or more) biomarkers selected from the group consisting of IL-17A, IL-7, IL-5, IL-4 and IL-13, or a fragment thereof, in a sample obtained from the subject, in the presence and absence of a TNFα inhibitor; wherein a decrease in a level of the one or more (e.g., 3 or more) biomarkers in the presence of the TNFα inhibitor as compared to a level of the one or more (e.g., 3 or more) biomarkers in the absence of the TNFα inhibitor indicates that the subject is responsive to treatment with the TNFα inhibitor. In these embodiments, the treatment-naïve subject is a subject who has not previously undergone therapy for IBD with a biological agent.

In certain embodiments, the biological agent is an anti-TNFα antibody selected from the group consisting of infliximab, adalimumab, golimumab and certolizumab pegol, or antigen-binding fragment thereof.

In certain embodiments, the biological agent is a TNFα-binding protein selected from the group consisting of etanercept.

In certain embodiments, the treatment-naïve subject is a subject who has previously undergone therapy for IBD with a steroid, an immunomodulator, or a combination thereof, but not with one or more of the aforementioned biological agents.

Another aspect of the invention provides a method for determining whether a subject having IBD who has previously undergone therapy with a TNFα inhibitor will be responsive to treatment with TNFα inhibitor, comprising determining a level of one or more (e.g., 3 or more) biomarkers selected from the group consisting of IL-17A, IL-7, IL-5, IL-4 and IL-13, or a fragment thereof, in a sample obtained from the subject (e.g., ex vivo explant culture of a tissue biopsy), in the presence and absence of a TNFα inhibitor; wherein a decrease in a level of the one or more (e.g., 3 or more) biomarkers in the presence of the TNFα inhibitor as compared to a level of the one or more (e.g., 3 or more) biomarkers in the absence of the TNFα inhibitor indicates that the subject is responsive to treatment with the TNFα inhibitor.

In certain embodiments, the subject has previously undergone therapy with an anti-TNFα antibody or antigen-binding fragment thereof, selected from the group consisting of infliximab, adalimumab, golimumab and certolizumab pegol, or antigen-binding fragment thereof.

In certain embodiments, the subject who has previously undergone therapy with an anti-TNFα antibody or antigen-binding fragment thereof is in remission from treatment with the anti-TNFα antibody or antigen-binding fragment thereof.

In certain embodiments, the subject who has previously undergone therapy with an anti-TNFα antibody or antigen-binding fragment thereof is refractory or non-responsive to the anti-TNFα antibody or antigen-binding fragment thereof.

In certain embodiments, the subject who is refractory or non-responsive to the anti-TNFα antibody or antigen-binding fragment thereof is a subject undergoing treatment with a second agent selected from the group consisting of vedolizumab, tofacitinib and ustekinumab, or a combination thereof.

Another aspect of the invention provides a method for determining whether a subject having IBD will be responsive to treatment with a TNFα inhibitor, comprising determining a severity of the IBD in the subject; determining a level of one or more (e.g., 3 or more) biomarkers selected from the group consisting of IL-17A, IL-7, IL-5, IL-4 and IL-13, or a fragment thereof, in a sample obtained from the subject (e.g., ex vivo explant culture of a tissue biopsy), in the presence and absence of a TNFα inhibitor; wherein a decrease in a level of the one or more (e.g., 3 or more) biomarkers in the presence of the TNFα inhibitor as compared to a level of the one or more (e.g., 3 or more) biomarkers in the absence of the TNFα inhibitor indicates that the subject is responsive to treatment with the TNFα inhibitor, thereby determining whether a subject having IBD is responsive to treatment with the TNFα inhibitor.

In certain embodiments, the disease severity may be determined via Harvey-Bradshaw index (HBI) method, endoscopy scoring method, or a combination thereof.

Another aspect of the invention provides a method for determining whether a subject having active IBD, such as moderate IBD, will be responsive to treatment with a TNFα inhibitor, comprising determining a level of one or more (e.g., 3 or more) biomarkers selected from the group consisting of IL-17A, IL-7, IL-5, IL-4 and IL-13, or a fragment thereof, in a sample obtained from the subject (e.g., ex vivo explant culture of a tissue biopsy), in the presence and absence of a TNFα inhibitor; wherein a decrease in a level of the one or more (e.g., 3 or more) biomarkers in the presence of the TNFα inhibitor as compared to a level of the one or more (e.g., 3 or more) biomarkers in the absence of the TNFα inhibitor indicates that the subject having active IBD, such as moderate IBD, is responsive to treatment with the TNFα inhibitor.

Another aspect of the invention provides a method for determining whether a subject having severe IBD will be responsive to treatment with a TNFα inhibitor, comprising determining a level of one or more (e.g., 3 or more) biomarkers selected from the group consisting of IL-17A, IL-7, IL-5, IL-4 and IL-13, or a fragment thereof, in a sample obtained from the subject (e.g., ex vivo explant culture of a tissue biopsy), in the presence and absence of a TNFα inhibitor; wherein a decrease in a level of the one or more (e.g., 3 or more) biomarkers in the presence of the TNFα inhibitor as compared to a level of the one or more (e.g., 3 or more) biomarkers in the absence of the TNFα inhibitor indicates that the subject having severe IBD is responsive to treatment with the TNFα inhibitor.

Another aspect of the invention provides a method for determining the severity of IBD in a subject having IBD, comprising determining a level of one or more (e.g., 3 or more) biomarkers selected from the group consisting of IL-17A, IL-7, IL-5, IL-4 and IL-13, or a fragment thereof, in a sample obtained from the subject (e.g., ex vivo explant culture of a tissue biopsy), and correlating the severity of the IBD with a high level of the one or more (e.g., 3 or more) biomarkers (e.g., level higher than a normal control or a reference value).

Another aspect of the invention provides a method for determining whether a subject having IBD will be responsive to treatment with a TNFα inhibitor, comprising determining a level of one or more (e.g., 3 or more) biomarkers selected from the group consisting of IL-17A, IL-7, IL-5, IL-4 and IL-13, or a fragment thereof and at least one cytokine/chemokine/inflammatory mediator selected from the group consisting of granulocyte macrophage colony-stimulating factor (GM-CSF), interferon gamma (IFNγ), interleukin 10 (IL-10), interleukin 12 70-kDa (IL-12p70), interleukin 12 40-kDa (IL-12p40), interleukin 1 beta (IL-1β), interleukin 2 (IL-2), interleukin 6 (IL-6), interleukin 8 (IL-8), monocyte chemoattractant protein-1 (MCP-1), and tumor necrosis factor alpha (TNFα), or a fragment thereof; wherein a decrease in a level of the one or more (e.g., 2 or more) biomarkers and one or more (e.g., 2 or more) cytokines/chemokines/inflammatory mediators in the presence of the TNFα inhibitor as compared to a level of the one or more (e.g., 2 or more) biomarkers and one or more (e.g., 2 or more) cytokines/chemokines/inflammatory mediators in the absence of the TNFα inhibitor indicates that the subject having IBD is responsive to treatment with the TNFα inhibitor.

In certain embodiments, a decrease in a level of at least one (e.g., 2 or more) biomarker selected from IL-17A, IL-7, IL-5, IL-4 and IL-13, or a fragment thereof, and decrease in a level of at least one (e.g., 2 or more) cytokine selected from GM-CSF, IFNγ, IL-10, IL-12p70, IL-12p40, IL-1β, IL-2, IL-8, MCP-1, and TNFα, or a fragment thereof, in the presence of the TNFα inhibitor as compared to a level of the one or more (e.g., 2 or more) biomarkers and one or more (e.g., 2 or more) cytokines/chemokines/inflammatory mediators in the absence of the TNFα inhibitor indicates that the subject having IBD is responsive to treatment with the TNFα inhibitor.

In certain embodiments, the cytokine/chemokine/inflammatory mediator levels are determined using an assay selected from the group consisting of enzyme-linked immuosorbent assay (ELISA), mass spectrometry (MS), immunoblotting (WB) and immunohistochemistry (IHC).

Another aspect of the invention provides a method for determining whether a subject having IBD will be responsive to treatment with a Janus kinase (JAK) inhibitor, comprising determining a level of one or more (e.g., 3 or more) biomarkers selected from the group consisting of interleukin 6 (IL-6), interleukin 8 (IL-8), MCP-1, TNFα, GM-CSF, IFNγ, IL-1β, or a fragment thereof, in a sample obtained from the subject (e.g., ex vivo explant culture of a tissue biopsy), in the presence and absence of a JAK inhibitor; wherein a decrease in a level of the one or more (e.g., 3 or more) biomarkers in the presence of the JAK inhibitor as compared to a level of the one or more (e.g., 3 or more) biomarkers in the absence of the JAK inhibitor indicates that the subject is responsive to treatment with the JAK inhibitor, thereby determining whether a subject having IBD is responsive to treatment with the JAK inhibitor.

In certain embodiments, the JAK inhibitor is ruxolitinib, tofacitinib (tasocitinib; CP-690550), upadacitinib (ABT-494), baricitinib (LY3009104, INCB28050), CYT387, Filgotinib (GLPG0634), lestaurtinib, pacritinib (SB1518), JSI-124, and CHZ868, or a combination thereof.

In certain embodiments, the JAK inhibitor is a compound selected from the group consisting of tofacitinib, and ruxolitinib, or a combination thereof.

Another aspect of the invention relates to methods for treating a subject having IBD comprising determining a level of one or more (e.g., 3 or more) biomarkers selected from the group consisting of IL-17A, IL-7, IL-5, IL-4 and IL-13, or a fragment thereof, in a sample obtained from the subject (e.g., ex vivo explant culture of a tissue biopsy), in the presence and absence of a tumor necrosis factor alpha (TNFα) inhibitor; and administering to the subject the TNFα inhibitor if the level of the one or more (e.g., 3 or more) biomarkers is lower in the presence of the TNFα inhibitor as compared to a level of the biomarker in the absence of the TNF-α inhibitor, thereby treating the subject having IBD.

In certain embodiments, the biomarkers are detected in an intestinal mucosal sample obtained from the subject.

In certain embodiments, the biomarkers are detected in a biopsy obtained from an affected area of an inflamed intestinal mucosa.

In certain embodiments, the biomarkers are detected in a blood sample, a stool sample, or an (intestinal) luminal wash obtained from the subject.

Another aspect of the invention relates to a method for treating a subject having IBD which is selected from the group consisting of ulcerative colitis (UC), Crohn's disease (CD), collagenous colitis and lymphocytic colitis with a TNFα inhibitor, comprising determining a level of one or more (e.g., 3 or more) biomarkers selected from the group consisting of IL-17A, IL-7, IL-5, IL-4 and IL-13, or a fragment thereof, in a sample obtained from the subject (e.g., ex vivo explant culture of a tissue biopsy), in the presence and absence of a TNFα inhibitor; and administering to the subject the TNFα inhibitor if the level of the one or more (e.g., 3 or more) biomarkers is lower in the presence of the TNFα inhibitor as compared to a level of the biomarker in the absence of the TNF-α inhibitor.

In a related therapeutic embodiment, the instant invention relates to a method for treating a subject having IBD with a TNFα inhibitor which is an anti-TNFα antibody, or antigen-binding fragment thereof, comprising determining a level of one or more (e.g., 3 or more) biomarkers selected from the group consisting of IL-17A, IL-7, IL-5, IL-4 and IL-13, or a fragment thereof, in a sample obtained from the subject (e.g., ex vivo explant culture of a tissue biopsy), in the presence and absence of an anti-TNFα antibody or antigen-binding fragment thereof; and administering to the subject the TNFα inhibitor if the level of the one or more (e.g., 3 or more) biomarkers is lower in the presence of the TNFα inhibitor as compared to a level of the biomarker in the absence of the TNF-α inhibitor.

In certain embodiments, the anti-TNFα antibody or antigen-binding fragment thereof is selected from the group consisting of infliximab, adalimumab, golimumab and certolizumab pegol, or antigen-binding fragment thereof, or a combination thereof.

In one embodiment, the anti-TNFα antibody, or antigen-binding fragment thereof, is infliximab, or an antigen-binding fragment thereof.

In one embodiment, the biomarker that is detected is a protein biomarker. Thus, under this embodiment, the detected biomarker is selected from the group consisting of IL-17A, IL-7, IL-5, IL-4 and IL-13, or a fragment thereof.

In one embodiment, the biomarker that is detected is a nucleic acid biomarker. Thus, under this embodiment, the detected nucleic acid biomarker is a nucleic acid which encodes IL-17A, IL-7, IL-5, IL-4 and IL-13, or a fragment thereof. The nucleic acid may be mRNA extracted from cells in the ex vivo explant culture of a tissue biopsy, or from exosomes released to the supernatant of such cultures.

Another aspect of the invention provides a method for treating a subject having IBD with a TNFα inhibitor, comprising determining a level of one or more (e.g., 3 or more) protein biomarkers selected from the group consisting of IL-17A, IL-7, IL-5, IL-4 and IL-13, or a fragment thereof, in a sample obtained from the subject (e.g., ex vivo explant culture of a tissue biopsy), with an assay selected from the group consisting of enzyme-linked immuosorbent assay (ELISA), mass spectrometry (MS), immunoblotting (WB) and immunohistochemistry (IHC); and administering to the subject the TNFα inhibitor if the level of the one or more (e.g., 3 or more) protein biomarkers is lower in the presence of the TNFα inhibitor as compared to a level of the biomarker in the absence of the TNF-α inhibitor.

Another aspect of the invention provides a method for treating a treatment-naïve subject having IBD with a TNFα inhibitor, comprising determining a level of one or more (e.g., 3 or more) biomarkers selected from the group consisting of IL-17A, IL-7, IL-5, IL-4 and IL-13, or a fragment thereof, in a sample obtained from the subject, in the presence and absence of a TNFα inhibitor; and administering to the subject the TNFα inhibitor if the level of the one or more (e.g., 3 or more) protein biomarkers is lower in the presence of the TNFα inhibitor as compared to a level of the biomarker in the absence of the TNF-α inhibitor.

In certain embodiments, the treatment-naïve subject is a subject who has not previously undergone therapy for IBD with a biological agent. In one embodiment, the biological agent is an anti-TNFα antibody selected from the group consisting of infliximab, adalimumab, golimumab and certolizumab pegol, or antigen-binding fragment thereof.

In certain embodiments, the biological agent is a TNFα-binding protein selected from the group consisting of etanercept.

In certain embodiments, the treatment-naïve subject is a subject who has previously undergone therapy for IBD with a steroid, an immunomodulator, or a combination thereof, but not with one or more of the aforementioned biological agents.

Another aspect of the invention provides a method for treating a subject having IBD who has previously undergone therapy with a TNFα inhibitor, comprising determining a level of one or more (e.g., 3 or more) biomarkers selected from the group consisting of IL-17A, IL-7, IL-5, IL-4 and IL-13, or a fragment thereof, in a sample obtained from the subject (e.g., ex vivo explant culture of a tissue biopsy), in the presence and absence of a TNFα inhibitor; and administering to the subject the TNFα inhibitor if the level of the one or more (e.g., 3 or more) protein biomarkers is lower in the presence of the TNFα inhibitor as compared to a level of the biomarker in the absence of the TNF-α inhibitor.

In certain embodiments, the subject has previously undergone therapy with an anti-TNFα antibody or antigen-binding fragment thereof, selected from the group consisting of infliximab, adalimumab, golimumab and certolizumab pegol, or antigen-binding fragment thereof.

In certain embodiments, the subject who has previously undergone therapy with an anti-TNFα antibody or antigen-binding fragment thereof is in remission from treatment with the anti-TNFα antibody or antigen-binding fragment thereof.

In certain embodiments, the subject who has previously undergone therapy with an anti-TNFα antibody or antigen-binding fragment thereof is refractory or non-responsive to the anti-TNFα antibody or antigen-binding fragment thereof.

In certain embodiments, the subject who is refractory or non-responsive to the anti-TNFα antibody or antigen-binding fragment thereof is a subject undergoing treatment with a second agent selected from the group consisting of vedolizumab, tofacitinib and ustekinumab, or a combination thereof.

Another aspect of the invention provides a method for treating a subject having IBD with a TNFα inhibitor, comprising determining a severity of the IBD in the subject; determining a level of one or more (e.g., 3 or more) biomarkers selected from the group consisting of IL-17A, IL-7, IL-5, IL-4 and IL-13, or a fragment thereof, in a sample obtained from the subject (e.g., ex vivo explant culture of a tissue biopsy), in the presence and absence of a TNFα inhibitor; and administering to the subject the TNFα inhibitor if the level of the one or more (e.g., 3 or more) protein biomarkers is lower in the presence of the TNFα inhibitor as compared to a level of the biomarker in the absence of the TNF-α inhibitor.

In certain embodiments, the disease severity may be determined via Harvey-Bradshaw index (HBI) method, endoscopy scoring method, or a combination thereof.

Another aspect of the invention provides a method for treating a subject having active IBD, such as moderate IBD, with a TNFα inhibitor, comprising determining a level of one or more (e.g., 3 or more) biomarkers selected from the group consisting of IL-17A, IL-7, IL-5, IL-4 and IL-13, or a fragment thereof, in a sample obtained from the subject (e.g., ex vivo explant culture of a tissue biopsy), in the presence and absence of a TNFα inhibitor; and administering to the subject having active IBD, such as moderate IBD, the TNFα inhibitor if the level of the one or more (e.g., 3 or more) biomarkers is lower in the presence of the TNFα inhibitor as compared to a level of the biomarker in the absence of the TNF-α inhibitor.

Another aspect of the invention provides a method for treating a subject having severe IBD with a TNFα inhibitor, comprising determining a level of one or more (e.g., 3 or more) biomarkers selected from the group consisting of IL-17A, IL-7, IL-5, IL-4 and IL-13, or a fragment thereof, in a sample obtained from the subject (e.g., ex vivo explant culture of a tissue biopsy), in the presence and absence of a TNFα inhibitor; and administering to the subject the TNFα inhibitor if the level of the one or more (e.g., 3 or more) protein biomarkers is lower in the presence of the TNFα inhibitor as compared to a level of the biomarker in the absence of the TNF-α inhibitor.

Another aspect of the invention provides a method for treating a subject having IBD with a TNFα inhibitor, comprising determining a level of one or more (e.g., 3 or more) biomarkers selected from the group consisting of IL-17A, IL-7, IL-5, IL-4 and IL-13, or a fragment thereof, in a sample obtained from the subject (e.g., ex vivo explant culture of a tissue biopsy), in the presence and absence of a TNFα inhibitor; determining a change in the level of the biomarker in the presence of the TNFα inhibitor versus in the absence of the TNFα inhibitor; administering to the subject the TNFα inhibitor if the level of the one or more (e.g., 3 or more) protein biomarkers is lower in the presence of the TNFα inhibitor as compared to a level of the biomarker in the absence of the TNF-α inhibitor; determining a severity of the IBD in the subject prior to and after administration of the TNF-α inhibitor; and correlating a change in the severity of IBD with a change in the biomarker level, wherein a positive correlation between the change in the severity of IBD and the change in the biomarker level indicates that the treatment with the TNFα inhibitor is effective.

Another aspect of the invention provides a method for treating a subject having IBD with a TNFα inhibitor, comprising determining a level of one or more (e.g., 2 or more) biomarkers selected from the group consisting of IL-17A, IL-7, IL-5, IL-4 and IL-13, or a fragment thereof and at least one (e.g., 2 or more) cytokine selected from the group consisting of GM-CSF, IFNγ, IL-10, IL-12p70, IL-12p40, IL-1β, IL-2, IL-6, IL-8, MCP-1, and TNFα, or a fragment thereof; and administering to the subject the TNFα inhibitor if the level of the one or more (e.g., 2 or more) protein biomarkers and one or more (e.g., 2 or more) cytokines is lower in the presence of the TNFα inhibitor as compared to a level of the biomarker and a level of the cytokine in the absence of the TNF-α inhibitor.

This therapeutic embodiment may further involve determining a decrease in the level of at least one (e.g., 2 or more) biomarker and a decrease in the level of at least one (e.g., 2 or more) cytokine after administration of the TNFα inhibitor, which indicates that the subject having IBD is responding to treatment with the TNFα inhibitor.

In certain embodiments, the cytokine levels are determined using an assay selected from the group consisting of enzyme-linked immuosorbent assay (ELISA), mass spectrometry (MS), immunoblotting (WB) and immunohistochemistry (IHC).

Another aspect of the invention provides a method for treating a subject having IBD with an agent selected from the group consisting of vedolizumab, tofacitinib and ustekinumab, or a combination thereof, comprising determining a level of one or more (e.g., 3 or more) biomarkers selected from the group consisting of GM-CSF, IFNγ, IL-10, IL-12p70, IL-12p40, IL-1β, IL-2, IL-4, IL-5, IL-6, IL-7, IL-8, IL-13, IL-17A, MCP-1, and TNFα, or a fragment thereof; and administering to the subject the agent if the level of the one or more (e.g., 3 or more) biomarkers is lower in the presence of the agent as compared to a level of the biomarker in the absence of the agent.

In certain embodiments, the biomarker is selected from the group consisting of IL-17A, IL-7, IL-5, IL-4 and IL-13, or a fragment thereof.

In certain embodiments, the IBD is ulcerative colitis or Crohn's disease.

Another aspect of the invention provides a method for treating a subject having inflammatory bowel disease (IBD) with a Janus kinase (JAK) inhibitor, comprising determining a level of one or more (e.g., 3 or more) biomarkers selected from the group consisting of interleukin 6 (IL-6), interleukin 8 (IL-8), MCP-1, TNFα, GM-CSF, IFNγ, IL-1β, or a fragment thereof, in a sample obtained from the subject (e.g., ex vivo explant culture of a tissue biopsy), in the presence and absence of a JAK inhibitor; and administering to the subject the JAK inhibitor if the level of the one or more (e.g., 3 or more) biomarkers is lower in the presence of the JAK inhibitor as compared to a level of the biomarker in the absence of the JAK inhibitor.

In certain embodiments, the JAK inhibitor is ruxolitinib, tofacitinib (tasocitinib; CP-690550), upadacitinib (ABT-494), baricitinib (LY3009104, INCB28050), CYT387, Filgotinib (GLPG0634), lestaurtinib, pacritinib (SB1518), JSI-124, and CHZ868, or a combination thereof.

In certain embodiments, the JAK inhibitor is a compound selected from the group consisting of tofacitinib, and ruxolitinib, or a combination thereof.

Another aspect of the invention provides a method for quantifying an outcome of treatment of IBD with an anti-TNFα antibody in a subject, comprising detecting and quantitating, in a sample obtained from the subject, at least one (e.g., 3 or more) biomarker selected from the group consisting of GM-CSF, IFNγ, IL-10, IL-12p70, IL-12p40, IL-1β, IL-2, IL-4, IL-5, IL-6, IL-7, IL-8, IL-13, IL-17A, MCP-1, and TNFα, or a fragment thereof; and comparing a level of expression of the biomarker in the subject's sample with a reference standard, wherein a differential level of expression of the biomarker in the sample compared to the level of expression of the biomarker in the reference standard is indicative of the outcome of treatment of IBD with the anti-TNFα antibody.

In certain embodiments, the biomarker is selected from the group consisting of IL-17A, IL-7, IL-5, IL-4 and IL-13, or a fragment thereof.

In certain embodiments, the IBD is ulcerative colitis or Crohn's disease.

Another aspect of the invention provides a method for quantifying an outcome of treatment of Crohn's disease (CD) with an anti-TNFα antibody in a subject, comprising detecting and quantitating, in a sample obtained from the subject (e.g., ex vivo explant culture of a tissue biopsy), at least one (e.g., 3 or more) biomarker selected from the group consisting of GM-CSF, IFNγ, IL-10, IL-12p70, IL-12p40, IL-1β, IL-2, IL-4, IL-5, IL-6, IL-7, IL-8, IL-13, IL-17A, MCP-1, and TNFα, or a fragment thereof; and comparing a level of expression of the biomarker in the subject's sample with a reference standard, wherein a reduction in the level of expression of the biomarker in the sample compared to the level of expression of the biomarker in the reference standard is indicative of the outcome of treatment of CD with the anti-TNFα antibody.

In certain embodiments, the reference standard comprises about 3.5 pg/ml IL-5, about 8.2 pg/ml IL-7, about 9.0 pg/ml IL-13, about 11.0 pg/ml IL-2, about 20.0 pg/ml TNF-α, about 22.0 pg/ml IL-17A, about 28.0 pg/ml IFN, about 29.0 pg/ml IL-12p70, about 20.0 pg/ml IL-1B, about 29.0 pg/ml IL-4, about 44.0 pg/ml IL-10, about 55.0 pg/ml GM-CSF, about 55.0 pg/ml IL-12p40, about 700 pg/ml IL-6, about 900 pg/ml MCP-1 and about 6000 pg/ml IL-8.

Another aspect of the invention provides a method for quantifying an outcome of treatment of ulcerative colitis (UC) with an anti-TNFα antibody in a subject, comprising detecting and quantitating, in a sample obtained from the subject (e.g., ex vivo explant culture of a tissue biopsy), at least one (e.g., 3 or more) biomarker selected from the group consisting of GM-CSF, IFNγ, IL-10, IL-12p70, IL-12p40, IL-1β, IL-2, IL-4, IL-5, IL-6, IL-7, IL-8, IL-13, IL-17A, MCP-1, and TNFα, or a fragment thereof; and comparing a level of expression of the biomarker in the subject's sample with a reference standard, wherein a reduction in the level of expression of the biomarker in the sample compared to the level of expression of the biomarker in the reference standard is indicative of the outcome of treatment of UC with the anti-TNFα antibody.

In certain embodiments, the reference standard comprises about 2.1 pg/ml IL-5, about 2.8 pg/ml IL-7, about 5.0 pg/ml IL-13, about 6.0 pg/ml IL-2, about 5.8 pg/ml TNF-α, about 20.0 pg/ml IL-17A, about 9.8 pg/ml IFN, about 29.0 pg/ml IL-12p70, about 4.6 pg/ml IL-1B, about 14.0 pg/ml IL-4, about 12.0 pg/ml IL-10, about 19.0 pg/ml GM-CSF, about 34.0 pg/ml IL-12p40, about 125 pg/ml IL-6, about 425 pg/ml MCP-1 and about 3000 pg/ml IL-8.

Another aspect of the invention relates to a method for monitoring an effectiveness of an anti-tumor necrosis factor alpha (TNFα) antibody, or antigen-binding fragment thereof, treatment of a subject having IBD method comprising determining a level of one or more (e.g., 3 or more) biomarkers selected from the group consisting of interleukin 17A (IL-17A), interleukin 7 (IL-7), interleukin 5 (IL-5), interleukin 4 (IL-4) and interleukin 13 (IL-13), or a fragment thereof, in a sample obtained from the subject prior to the initiation of the treatment; determining the level of the one or more (e.g., 3 or more) biomarkers in a second sample(s) from the subject after at least a portion of the treatment has been administered; comparing the level of the one or more (e.g., 3 or more) biomarkers in the first sample(s) with a level of the one or more (e.g., 3 or more) biomarkers in the second sample(s), wherein a difference in the level of the one or more (e.g., 3 or more) markers in the first sample(s) as compared to the level of the one or more (e.g., 3 or more) markers in the second sample(s) indicates that the subject is responding to the treatment.

In certain embodiments, in one instance, the response indicates remission of the IBD. In another instance, the response indicates stabilization of the IBD.

Another aspect of the invention relates to a method for screening for an agent capable of influencing the outcome of a patient suffering from inflammatory bowel disease (IBD), comprising contacting a sample obtained from the patient (e.g., ex vivo explant culture of a tissue biopsy) with a test agent; and detecting the expression level of one or more (e.g., 3 or more) biomarkers selected from the group consisting of GM-CSF, IFNγ, IL-10, IL-12p70, IL-12p40, IL-1β, IL-2, IL-4, IL-5, IL-6, IL-7, IL-8, IL-13, IL-17A, MCP-1, and TNFα, or a fragment thereof, in a sample before and after contacting with the test agent; wherein an attenuation in the levels of the (e.g., 3 or more) biomarker after contacting with the test agent compared to the levels of the biomarker before contacting with the test agent indicates that the test agent is capable of influencing the outcome of the patient suffering from IBD.

In one embodiment, the biomarker is selected from the group consisting of interleukin 17A (IL-17A), interleukin 7 (IL-7), interleukin 5 (IL-5), interleukin 4 (IL-4) and interleukin 13 (IL-13), or a fragment thereof.

It should be noted that any one embodiment described herein, including those only described under one aspect of the invention, and those only described in the examples, is contemplated to be able to combine with any other embodiment(s), unless explicitly disclaimed or otherwise would have been improper.

Other features and advantages of the invention will be apparent from the following description of the preferred embodiments thereof, and from the claims. References cited are hereby incorporated by reference.

BRIEF DESCRIPTION OF THE DRAWINGS

Various features and advantages of the embodiments herein described can be fully appreciated as the same becomes better understood when considered in light of the accompanying drawings:

FIG. 3A shows a plot of number of cytokines that are down-regulated by infliximab treatment ex vivo per patient, with each dot representing one patient. The median value and first and third quartiles are shown in the box-plot.

FIG. 3B shows ex vivo response rates to infliximab treatment in anti-TNFα naïve patients (N=21, clear bar) and patients previously exposed to anti-TNFα treatment (N=25, dark bar). Responders were patients exhibiting down-regulation of >2 (three or more) cytokines in the infliximab-treated cultures.

FIG. 4A shows assessment of the number of cytokines per patient inhibited by infliximab treatment as evaluated ex vivo in patients with IBD (N=28) who responded or not to infliximab therapy. Clinical responders had a significantly higher number of cytokines inhibited in the ex vivo testing compared to patients lacking clinical therapeutic responses to infliximab. Data are expressed as mean±SEM. (*p=0.0009 by a non-parametric test).

FIG. 4B shows clinical response rates to infliximab therapy in all patients and according to their responses to the ex vivo testing. Patients positive in the ex vivo treatment had a significantly higher clinical response rate (83%) to infliximab treatment, compared to that (6%) of the non-responders with negative ex vivo results (*p=0.015 when comparing the clinical response rate for patients with positive ex vivo response, with that of all patients, by Fisher's exact test; and *p=0.0001 when comparing the clinical response rates for patients with positive vs. negative ex vivo responses).

FIGS. 5A-5H show bar charts displaying cytokine profiles of patients in response to treatment with various agents.

FIG. 5A shows changes in cytokine profiles of patients treated with 0.5 mg/ml infliximab (an anti-TNFα antibody).

FIG. 5B shows changes in cytokine profiles of patients treated with 100 μM tofacitinib (a Janus Kinase (JAK) inhibitor).

FIG. 5C shows changes in cytokine profiles of patients treated with 10 μM concentration of an experimental drug.

FIG. 5D shows changes in cytokine profiles of a patient (ID 13-284) treated with anti-TNFα antibody infliximab. The patient is an ex vivo responder with three cytokine expression down-regulation in addition to the direct target of infliximab—TNFα.

FIG. 5E shows changes in cytokine profiles of a patient (ID 13-394) treated with JAK inhibitor tofacitinib. The patient is an ex vivo responder with three cytokine expression down-regulation.

FIG. 5F shows changes in cytokine profiles of a patient (ID 13-562) treated with anti-integrin antibody vedolizumab. The patient is an ex vivo non-responder with only one cytokine expression down-regulation and four cytokine expression up-regulation.

FIG. 5G shows changes in cytokine profiles of a patient (ID 13-426) treated with an experimental drug A, which is a small molecule G-protein coupled receptor (GPCR) antagonist. The patient is an ex vivo non-responder with one cytokine expression up-regulation.

FIG. 5H shows changes in cytokine profiles of a patient (ID 13-445) treated with an experimental drug B, which is a small molecule protease inhibitor. The patient is an ex vivo non-responder with only two cytokine expression down-regulation.

DETAILED DESCRIPTION OF THE INVENTION

Figure 1:
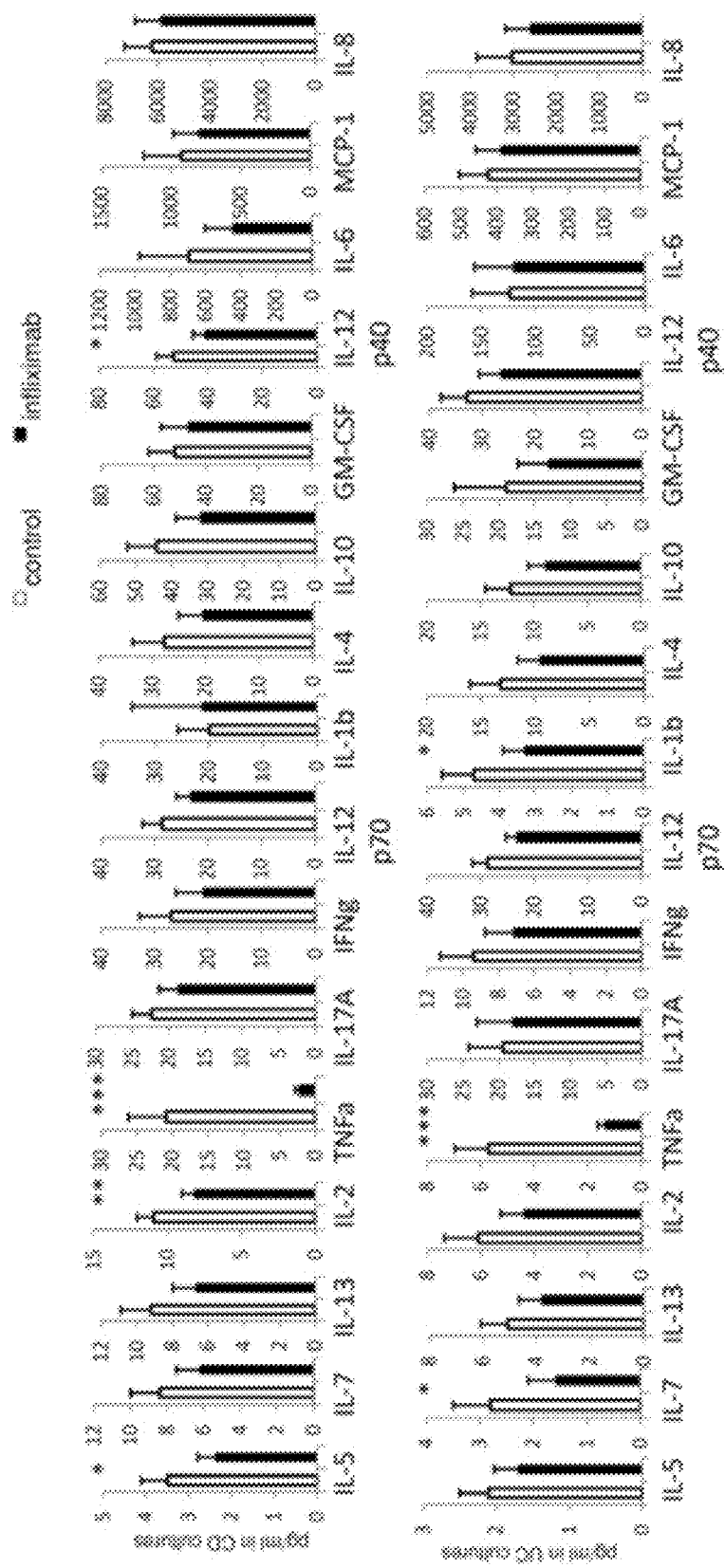
FIG. 1 shows a bar chart displaying changes in cytokine secretion by mucosal explants treated with infliximab. Mucosal biopsies from 29 patients with Crohn's disease (upper panel) and 16 patients with ulcerative colitis (lower panel) were cultured in the presence (dark bars) or absence (clear bars) of infliximab, and the levels of various cytokines in culture supernatant were measured by multiplex ELISA. Each bar represents group mean±SE. *p<0.05; p<0.001, *p<0.0001.

The present invention provides a robust, replicable, and quantitative method for determining response of subjects with IBD to TNFα inhibitors. In contrast to prior approaches based purely on qualitative analysis (of a list of cytokines), the methods of the instant invention takes into consideration inter-patient variability in the predictors themselves by introducing a quantitative component.

While not wishing to be bound by any particular theory, the methods of the invention are partly based on the notion that IBD is a heterogeneous disease in terms of its etiology and mechanisms of pathogenesis, and thus not all IBD patients are characterized by TNF-driven disease. The strength of the methods described herein is that it can distinguish such patients and can identify individuals in whom even successful neutralization of TNF activity does not have broader effects in heterologous cytokine networks that are responsible for sustaining a chronic inflammatory state in IBD.

Also, compared to previous studies using isolated cell populations, embodiments described herein utilize tissue explants, which retain functional interactions between the different cell types of the intestinal mucosa including various immune cells. Accordingly, the assay methods of the instant invention have uncovered new biomarkers that offer mechanistic cues to therapy of IBD, which is mediated via potential IBD therapeutic agents such as antagonistic anti-TNFα antibodies.

The instant methods offers significant improvements over existing methods. For instance, the assay methods described herein allow for accommodation of both subjects with Crohn's disease and ulcerative colitis, which was hitherto unrecognized in the field of IBD diagnostics. The methods of the instant invention work equally well with biopsies obtained from ileum and colon. Furthermore, the results obtained with treatment-naïve subjects was comparable with subjects previously or currently undergoing anti-TNFα therapy, thus suggesting that the test can be applied so as to further guide medical decisions about increasing the dose or frequency of the medication, switching to another anti-TNFα drug or even proceed to surgery.

The ex vivo testing methods described herein can also be used in patient selection for clinical trials. In fact, inclusion of one or more (e.g., 3 or more) of the biomarkers in the follow-up therapy improved clinical response from 39% to 83%, which was in line with the findings of Atreya et al. (2014). The assay techniques can also be tied to existing methods so as to improve the accuracy and/or reliability of diagnostic methods.

Additionally, the instant invention provides for diagnosis and/or therapy of IBD at low cost. The assay methods of the instant invention do not require sophisticated machinery and/or reagents and can be administered easily at hospitals and clinical laboratories. The exemplified embodiments using biopsy samples may be adapted for use with other samples, such as blood sample, stool sample, or (intestinal) luminal wash.

Furthermore, embodiments described herein provide new biomarkers that are useful in prognosticating and further determining the clinical response of IBD patients to the therapy with anti-TNFα antibodies (or JAK inhibitors). The biomarkers of the instant application are also clinically significant because they are components of pathways that are globally regulated by TNFα (or JAK-STAT pathway) in the context of IBD. The biomarkers and the methods described in the instant application are further useful in the context of screening for new lead compounds and therapeutic agents that are clinically useful in the therapy of IBD. The latter application is useful in a least two critical phases of drug development: in pre-clinical evaluation of drug effectiveness, and in early phase clinical trials seeking to gather evidence of drug efficacy.

Thus in one aspect, the invention provides a method of determining the number of cytokines exhibiting statistically significant down-regulation, after contacting a candidate compound with a mucosal explant culture of a biopsy from a diseased area of an inflamed intestinal mucosa from a subject having inflammatory bowel disease (IBD), the method comprising: (a) obtaining a biopsy from a macroscopically diseased area of an inflamed intestinal mucosa from a subject having inflammatory bowel disease (IBD); (b) producing a first mucosal explant culture of the biopsy in the absence of a candidate compound, and a second mucosal explant culture of the biopsy in the presence of the candidate compound; (c) comparing the expression levels of a panel of cytokines, chemokines, and inflammatory mediators relating to IBD or treatment thereof (e.g., mediators of inflammation in IBD), in the supernatant of said first mucosal explant culture and the supernatant of said second mucosal explant culture; and, (d) determining the number of said cytokines, chemokines and inflammatory mediators, from said panel of cytokines, that exhibit statistically significant down-regulation after contacting the candidate compound with the second mucosal explant culture.

As used herein, the term "cytokine" may sometimes be used to collectively refer to "cytokine/chemokine/inflammatory mediator."

The method described above ("the base method") can be used as the basis for other methods of the invention. For example, the number of cytokines exhibiting statistically significant down-regulation may be used to assess whether the candidate compound is (when the number is 3 or more, including the direct target of the candidate compound such as TNFα as the direct target of an anti-TNFα antibody as the candidate compound; or when the number is 2 or more, in addition to the direct target of the candidate compound), or is not (when the number is 2 or less, including the direct target of the candidate compound; or when the number is 1 or less, in addition to the direct target of the candidate compound) suitable for treating the subject from which the mucosal explant culture is established. The base method can also be used to evaluate drug or candidate drug efficacy.

Thus another aspect of the invention provides a method of selecting two or more test compounds for combination therapy for inflammatory bowel disease (IBD) treatment, the method comprising: (a) using the base method, identifying a first candidate compound resulting in statistically significant down-regulation of a first subset of three or more of said cytokines, chemokines and inflammatory mediators; (b) using the base method, identifying a second candidate compound resulting in statistically significant down-regulation of a second subset of three or more of said cytokines, chemokines and inflammatory mediators; (c) administering an effective amount of the first candidate compound and an effective amount of the second candidate compound to the subject for combination therapy, when said first subset and said second subset of three or more of said cytokines, chemokines and inflammatory mediators are different (e.g., completely different, or with no more than 1 or 2 overlap).

According to this aspect of the invention, two (or more) candidate compounds leading to completely different or large different cytokine down-regulation patterns likely work through different or complementary inhibitory pathways, and thus combining these two or more candidate compounds in a combination therapy will likely lead to synergistic response in the patient treated by the combination therapy.

Conversely, if two (or more) candidate compounds leading to substantially the same or very similar cytokine down-regulation patterns likely work through identical or closely related inhibitory pathways, and thus combining these two or more candidate compounds in a combination therapy may not lead to responses that are merely additive. Thus the method of the invention can uncover mechanisms of action of established or emerging IBD therapeutics, and thus point to more efficient treatment combinations, while avoiding unproductive combinations.

Here, "cytokine down-regulation pattern" is defined more by the identity of the specific cytokines in the tested cytokine panel that exhibit statistically significant down-regulation, than by the magnitude of down-regulation in those specific cytokines, although the magnitude of changes may also contribute to the cytokine down-regulation pattern.

Another aspect of the invention provides a method of identifying a test compounds suitable for inflammatory bowel disease (IBD) treatment, the method comprising: using the base method, identifying, from a library of test compounds, a test compound that results in statistically significant down-regulation of three or more of said cytokines, chemokines and inflammatory mediators, thereby identifying a test compounds suitable for inflammatory bowel disease (IBD) treatment.

There is a high rate of drug attrition as candidates move forward to clinical trials, making it critical to identify early on the ones that are likely to success or fail. According to a report from the Centre for Medicines Research, the phase II success rate for new molecular entities is less than 20%, and only 1 in 10,000 molecules developed reaches the market, with an estimated cost of $2 billion. Part of the problem, and specifically for diseases like IBD, obesity and cancer, is that efficacy data gathered from testing in animal models do not necessarily translate to new therapies. On the other hand, cases have been described in which drugs had shown little or no efficacy in animal models of IBD, but turned out to be successful for the treatment of human disease. Thus proof-of-concept studies using patient biopsies in predictive assays like the methods described herein are pivotal in minimizing the risk of drug failure.

This aspect of the invention provides an effective way to identify lead compound likely to be effective in subsequent pre-clinical or early stage clinical trials. Optionally, the method further comprises administering the test compound to a test subject to determine safety, efficacy, and/or adverse event of the test compound.

Another aspect of the invention provides a method of diagnosing and treating inflammatory bowel disease (IBD) in a subject, the method comprising: (a) obtaining a biopsy from a macroscopically diseased area of an inflamed intestinal mucosa from the subject; (b) producing a first mucosal explant culture of the biopsy in the absence of a candidate compound, and a second mucosal explant culture of the biopsy in the presence of the candidate compound; (c) comparing the expression levels of a panel of cytokines, chemokines, and inflammatory mediators relating to IBD or treatment thereof (e.g., mediators of inflammation in IBD), in the supernatant of said first mucosal explant culture and the supernatant of said second mucosal explant culture; (d) diagnosing the subject as being suitable for IBD treatment using the candidate compound, when three or more said cytokines, chemokines, and inflammatory mediators (or two or more cytokines, chemokines, and inflammatory mediators that are not direct target of the candidate compound), from said panel of cytokines, chemokines, and inflammatory mediators, exhibit statistically significant down-regulation after contacting the candidate compound with the second mucosal explant culture, and, (e) administering an effective amount of the candidate compound to the subject diagnosed in step (d) as being suitable for IBD treatment using the candidate compound, thereby diagnosing and treating IBD in said subject.

Another aspect of the invention provides a method of selecting a patient population sensitive to inflammatory bowel disease (IBD) treatment using a compound, the method comprising: (a) obtaining a biopsy from a macroscopically diseased area of an inflamed intestinal mucosa from a subject, from a plurality of patients that are candidates for IBD treatment; (b) producing a first mucosal explant culture of the biopsy in the absence of a compound, and a second mucosal explant culture of the biopsy in the presence of the compound; (c) comparing the expression levels of a panel of cytokines, chemokines, and inflammatory mediators relating to IBD or treatment thereof (e.g., mediators of inflammation in IBD), in the supernatant of said first mucosal explant culture and the supernatant of said second mucosal explant culture; (d) selecting the subject as being suitable for IBD treatment using the compound, when three or more said cytokines, chemokines, and inflammatory mediators (or two or more said cytokines, chemokines, and inflammatory mediators that are not direct target of the candidate compound), from said panel of cytokines, chemokines, and inflammatory mediators, exhibit statistically significant down-regulation after contacting the compound with the second mucosal explant culture; and, (e) repeating steps (a)-(d) for a different subject from said plurality of patients, until a pre-determined number of subjects are selected as being suitable for IBD treatment using the compound.

By employing screening approaches, like the methods of the invention, to select patients for early phase clinical trials, a substantially smaller number of patients need to be included to demonstrate drug efficacy due to higher response rates. This substantially reduces the cost and the time to complete the clinical drug testing, and the sensitized patient population with hightened response rate might also reveal positive results for a drug which otherwise could have been missed.

In certain embodiments, the supernatant can be isolated from the ex vivo explant culture by filtration and/or centrifugation, and can be used immediately, or thawed from storage at −80° C.

In certain embodiments, the IBD is selected from the group consisting of: ulcerative colitis (UC), Crohn's disease (CD), collagenous colitis, and lymphocytic colitis. In certain embodiments, the CD is moderately to severely active Crohn's disease.

In certain embodiments, the panel of cytokines, chemokines, and inflammatory mediators comprise, consist essentially of, or consist of: interleukin 17A (IL-17A), interleukin 7 (IL-7), interleukin 5 (IL-5), interleukin 4 (IL-4) and interleukin 13 (IL-13), granulocyte macrophage colony-stimulating factor (GM-CSF), interferon gamma (IFNγ), interleukin 10 (IL-10), interleukin 12 70-kDa (IL-12p70), interleukin 12 40-kDa (IL-12p40), interleukin 1 beta (IL-1β), interleukin 2 (IL-2), interleukin 6 (IL-6), interleukin 8 (IL-8), monocyte chemoattractant protein-1 (MCP-1), and tumor necrosis factor alpha (TNFα).

In certain embodiments, the panel of cytokines, chemokines, and inflammatory mediators optionally further comprises, consists essentially of, or consists of one or more of: IL-3, IL-9, IL-22, IL-23, IL-25, IL-35, IL-36, IL-37, TL1A, LIGHT and TGF-beta.

In certain embodiments, the three or more cytokines, chemokines, and inflammatory mediators are at least 5, 6, or 7 cytokines. In those embodiments of the invention, statistically significant down-regulation in 5, 6, 7, 8, 9 or more cytokines/chemokines/inflammatory mediators signifies that the candidate compound is effective to treat IBD in the patient from which the ex vivo explant culture is derived.

In certain embodiments, the compound is a nucleic acid (such as an antisense-RNA; miRNA inhibitor or mimetic); a bioactive lipid; a metabolite; a natural product; a bacteria (probiotics, or engineered) or bacterial product.

In certain embodiments, the compound is a medication that has been found to be successful in treating other autoimmune conditions such as rheumatoid arthritis, psoriasis, psoriatic arthritis, ankylosing spondilitis, HS, JRA, multiple sclerosis, SLE, etc., but has not yet been tested in CD or UC. Such discovery of new therapeutic uses for existing molecules, also known as drug repurposing, is not only cost-effective but also reduces by about 10 years the time to develop a new treatment.

In certain embodiments, the compound is a JAK family kinase (JAK1, JAK2, JAK3, etc.) inhibitor, such as tofacitinib, and said three or more cytokines, chemokines, and inflammatory mediators are IL-6, IL-8, MCP-1, and TNFα.

In certain embodiments, the compound is a JAK inhibitor.

In certain embodiments, the JAK inhibitor is ruxolitinib, tofacitinib (tasocitinib; CP-690550), upadacitinib (ABT-494), baricitinib (LY3009104, INCB28050), CYT387, Filgotinib (GLPG0634), lestaurtinib, pacritinib (SB1518), JSI-124, and CHZ868, or a combination thereof.

In certain embodiments, the compound is a TNFα inhibitor.

In certain embodiments, the TNFα inhibitor is an anti-TNFα antibody or an antigen-binding fragment thereof, a small molecule antagonist, anti-sense TNFα, or siRNA or miRNA targeting TNFα.

In certain embodiments, the anti-TNFα antibody comprises infliximab, adalimumab, golimumab, certolizumab pegol, a biosimilar thereof, or a combination thereof.

In certain embodiments, the compound antagonizes TNFα activity by binding to and sequestering TNFα (for example, the compound may be an anti-TNFα antibody such as infliximab, or a biosimilar thereof, or a chimeric molecule having a TNFα binding activity, such as etanercept), and the three or more cytokines, chemokines, and inflammatory mediators are IL-17A, IL-7, IL-5, IL-4 and IL-13.

In certain embodiments, expression levels of the panel of cytokines, chemokines, and inflammatory mediators are determined using an assay selected from the group consisting of: enzyme-linked immuosorbent assay (ELISA), mass spectrometry (MS), immunoblotting (WB), and immunohistochemistry (IHC).

In certain embodiments, the subject is a treatment-naïve subject who has not previously undergone therapy for IBD with a biological agent.

In certain embodiments, the subject is a treatment-naïve subject who has previously undergone therapy for IBD with a steroid, an immunomodulator, or a combination thereof.

In certain embodiments, the subject has previously undergone therapy for IBD.

In certain embodiments, the subject has previously undergone therapy with an anti-TNFα antibody or antigen-binding fragment thereof, selected from the group consisting of infliximab, adalimumab, golimumab, certolizumab pegol, or an antigen-binding fragment thereof.

In certain embodiments, the subject is in remission from treatment with the anti-TNFα antibody or antigen-binding fragment thereof; or is refractory or non-responsive to the anti-TNFα antibody or antigen-binding fragment thereof.

In certain embodiments, the biopsy is obtained through an endoscopic procedure (e.g., colonoscopy or sigmoidoscopy).

In certain embodiments, the biopsy is used in said explant culture within 30 minutes of excision. Preferably, the excised biopsy is kept at a temperature of between 0-4° C., preferably in a pre-cooled tissue culture media that is substantially the same as (or identical to) the tissue culture media for subsequent ex vivo explant culture.

In certain embodiments, the biopsy is obtained from the macroscopically most diseased area(s) of the inflamed intestinal mucosa.

In certain embodiments, the biopsy is obtained from terminal ileum, ileocolonic region, or colon of the subject.

In certain embodiments, the biopsy and the explant culture thereof comprise a mixture of different intestinal cell types including epithelial cells, immune cells, and stroma cells.

While not wishing to be bound by any particular theory, it is believed that the use of mucosal biopsies in the methods of the invention recapitulates, at least in part, the interactions between different cell types in the intestine, including epithelial cells, various types of immune cells and stroma cells.

In certain embodiments, the biopsy and the explant culture thereof are not stimulated or activated with an exogenous factor to promote cytokine secretion.

Again, while not wishing to be bound by any particular theory, it is believed that cytokine secretion in the methods of the invention is spontaneous and requires no additional stimulation. This is a fundamental difference from cultures of peripheral blood cells that have been used in previous studies that required exogenous stimulation for activation and cytokine secretion. Exogenous stimulation may introduce biases to the responses, as a high degree of variability in immune responses is well recognized among individuals and is often stimulus-dependent.

In certain embodiments, the first and second explant cultures are maintained at about 37° C. for about 18 hrs (e.g., about 6 hrs, 8 hrs, 10 hrs, 12 hrs, 14 hrs, 16 hrs, 18 hrs, 20 hrs, 22 hrs, or about 24 hrs) in a humidified chamber with 95% $O_2$/5% $CO_2$.

In certain embodiments, the first and second explant cultures each comprises 2, 3, 4, 5, or 6 replicas. The replicas may be derived from the same biopsy, or from different biopsies of the same patient.

In certain embodiments, statistical significance (e.g., $p<0.05$, or $p<0.01$) is established based on Mann-Whitney test.

Other aspects and embodiments of the invention are described in the Summary of the Invention section, all incorporated herein by reference.

For purposes of interpreting this specification, the following definitions will apply and whenever appropriate, terms used in the singular will also include the plural and vice versa. In the event that any definition set forth below conflicts with any document incorporated herein by reference, the definition set forth below shall control.

As used in this specification and the appended claims, the singular forms "a," "an" and "the" include plural referents unless the context clearly dictates otherwise. Thus, for example, reference to "a protein" includes a plurality of proteins; reference to "a cell" includes mixtures of cells, and the like.

Ranges provided in the specification and appended claims include both end points and all points between the end points. Thus, for example, a range of 2.0 to 3.0 includes 2.0, 3.0, and all points between 2.0 and 3.0. In addition, new ranges based on different end points of explicitly disclosed ranges are also contemplated (e.g., a new range of 2-40 is implicitly contemplated based on the explicitly disclosed ranges 2-31 and 31-40).

The invention is further described in more detail in the subsections below.

I. Methods of Treatment

In one aspect, the instant invention relates to methods for (diagnosing and) treating a subject having inflammatory diseases. Examples of such inflammatory diseases include, those mediated by TNFα, such as, inflammatory bowel disease (IBD), rheumatoid arthritis (RA) and psoriasis. Preferably, the diseases are characterized by presence of one or more disease markers, e.g., inflammatory cytokines, often in inflamed cells and/or tissues, e.g., biopsied material and the like. In certain embodiments, the compositions and methods of the instant invention relate to treatment of IBD.

Accordingly, in one embodiment, the instant invention relates to methods for treating a subject having inflammatory bowel disease (IBD), comprising determining a level of one or more (e.g., 3 or more) biomarkers selected from the group consisting of GM-CSF, IFNγ, IL-10, IL-12p70, IL-12p40, IL-1β, IL-2, IL-4, IL-5, IL-6, IL-7, IL-8, IL-13, IL-17A, MCP-1, and TNFα, or a fragment thereof, in a sample obtained from the subject (e.g., ex vivo explant culture of a tissue biopsy), in the presence and absence of test compound, such as a tumor necrosis factor alpha (TNFα) inhibitor (or Janus Kinase (JAK) inhibitor); and administering to the subject the test compounds, such as TNFα inhibitor (or JAK inhibitor) if the level of the one or more (e.g., 3 or more) biomarkers is lower in the presence of the test compound, e.g., TNFα inhibitor (or JAK inhibitor), as compared to a level of the biomarker in the absence of the test compounds, e.g., TNF-α inhibitor (or JAK inhibitor), thereby treating the subject having IBD.

In one embodiment, the method comprises determining a level of one or more (e.g., 3 or more) biomarkers selected from the group consisting of IL-17A, IL-7, IL-5, IL-4 and IL-13, or a fragment thereof. In another embodiment, the method comprises determining a level of one or more biomarkers selected from the group consisting of IL-6 and IL-8, or a combination thereof.

The aforementioned biomarkers which are determined in practicing the aforementioned therapeutic embodiment(s) are preferably protein biomarkers, although, nucleic acid biomarkers may also be employed alternately or additionally to the protein biomarkers.

"Treatment," "treating," and grammatical variations thereof refer to clinical intervention in an attempt to alter the natural course of the individual or cell being treated, and can be performed either for prophylaxis or during the course of clinical pathology. Desirable effects of treatment include preventing occurrence or recurrence of disease, alleviation of symptoms, diminishment of any direct or indirect pathological consequences of the disease (e.g., promoting mucosal healing in IBD subjects), decreasing the rate of disease progression, amelioration or palliation of the disease state, and remission or improved prognosis. In certain embodiments, treatment refers to treating a subject having s symptom of a target disease, such as IBD, or is medically required to be treated to control or alleviate a symptom of the disease/IBD.

"Treatment regimen" refers to a combination of dosage, frequency of administration, or duration of treatment, with or without addition of a second medication.

"Effective treatment regimen" refers to a treatment regimen that will offer beneficial response to a patient receiving the treatment.

"Patient response" or "patient responsiveness" can be assessed using any endpoint indicating a benefit to the patient, including, without limitation, (1) inhibition, to some extent, of disease progression, including slowing down and complete arrest; (2) reduction in the number of disease episodes and/or symptoms; (3) reduction in lesional size; (4) inhibition (i.e., reduction, slowing down or complete stopping) of disease cell infiltration into adjacent peripheral organs and/or tissues; (5) inhibition (i.e., reduction, slowing down or complete stopping) of disease spread; (6) decrease of auto-immune response, which may, but does not have to, result in the regression or ablation of the disease lesion; (7) relief, to some extent, of one or more symptoms associated with the disorder; (8) increase in the length of disease-free presentation following treatment; and/or (9) decreased mortality at a given point of time following treatment. The term "responsiveness" refers to a measurable response, including complete response (CR) and partial response (PR).

For example, to evaluation whether a patient is responding to treatment of Crohn's disease (CD), clinical indicators such as CDAI (Crohn's Disease Activity Index), disease-specific IBD questionnaire (IBDQ), and general health-related quality of life questionnaire (SF-36) may be used to evaluate clinical efficacy.

Similarly, to evaluation whether a patient is responding to treatment of Ulcerative Colitis (UC), clinical indicators such as Mayo Score, endoscopy subscore, or rectal bleeding subscore, etc. may be used to evaluate clinical efficacy. In certain embodiments, mucosal healing can be used as the primary outcome in patients with UC evaluated by flexible sigmoidoscopy. Mucosal healing (MH) is an evolving treatment goal as it has been associated with sustained clinical benefit in terms of clinical relapse rates, hospitalizations and surgeries.

As used herein, "complete response" or "CR" may generally means the disappearance of all signs of inflammation or remission in response to treatment. This does not necessarily mean the disease has been cured. In certain embodiment, CR has the same clinical definition for CD and UC, as specified in the infliximab label (incorporated herein by reference), in the respective sections in which clinical trial results were described for treating CD and UC with infliximab (REMICADE®).

"Partial response" or "PR" generally refers to a decrease of at least 50% in the severity of inflammation, in response to treatment. In certain embodiment, PR has the same clinical definition for CD and UC, as specified in the infliximab label (incorporated herein by reference), in the respective sections in which clinical trial results were described for treating CD and UC with infliximab (REMICADE®).

A "beneficial response" of a patient to treatment with a TNFα inhibitor and similar wording refers to the clinical or therapeutic benefit imparted to a patient at risk for or suffering from a gastrointestinal inflammatory disorder from or as a result of the treatment with the antagonist, such as an anti-TNFα antibody. Such benefit includes cellular or biological responses, a complete response, a partial response, a stable disease (without progression or relapse), or a response with a later relapse of the patient from or as a result of the treatment with the antagonist.

As used herein, "non-response" or "lack of response" or similar wording means an absence of a complete response, a partial response, or a beneficial response to treatment with a TNFα inhibitor.

"A patient maintains responsiveness to a treatment" when the patient' responsiveness does not decrease with time during the course of a treatment.

The term "sample," or "test sample" as used herein, refers to a composition that is obtained or derived from a subject of interest that contains a cellular and/or other molecular entity that is to be characterized and/or identified, for example based on physical, biochemical, chemical and/or physiological characteristics. In one embodiment, the definition encompasses blood and other liquid samples of biological origin and tissue samples such as a biopsy specimen or tissue cultures or cells derived therefrom. The source of the tissue sample may be solid tissue as from a fresh, frozen and/or preserved organ or tissue sample or biopsy or aspirate; blood or any blood constituents; bodily fluids; stool samples; (intestinal) luminal washes; and cells from any time in gestation or development of the subject or plasma.

In a specific embodiment, sample refers to puncture tissue biopsy or ex vivo explant culture thereof, said biopsy being obtained from a diseased area of an inflamed intestinal mucosa from a subject having inflammatory bowel disease (IBD). The diseased area may be a macroscopically most diseased area(s) of the inflamed intestinal mucosa. The diseased area may be from terminal ileum, ileocolonic region, or colon of the subject. The biopsy may be obtained through an endoscopic procedure (e.g., colonoscopy or sigmoidoscopy).

The term "sample," or "test sample" includes biological samples that have been manipulated in any way after their procurement, such as by chopping/slicing/cutting, treatment with reagents, solubilization, culturing, or enrichment for certain components, such as proteins or polynucleotides, or embedding in a semi-solid or solid matrix for sectioning purposes. For the purposes herein a "section" of a tissue sample is meant a single part or piece of a tissue sample, e.g., a thin slice of tissue or cells cut from a tissue sample. Samples include, but are not limited to, whole blood, blood-derived cells, serum, plasma, lymph fluid, synovial fluid, cellular extracts, and combinations thereof. In one embodiment, the sample is a clinical sample, such as a puncture biopsy obtained via an endoscopy procedure from a diseased area of the terminal ileum, ileocolonic region, or colon of the subject having IBD. The sample may also be a supernatant of an ex vivo explant culture of the biopsy or sections thereof. In another embodiment, the sample is used in a diagnostic assay.

A "reference sample," as used herein, refers to any sample, standard, or level that is used for comparison purposes. In certain embodiments, a reference sample is treated with a vehicle as opposed to a test compound, but otherwise identical to a test sample. In certain embodiments, a reference sample is obtained from a healthy and/or non-diseased part of the body (e.g., tissue or cells) of the same subject or patient. In another embodiment, a reference sample is obtained from an untreated tissue and/or cell of the body of the same subject or patient. In yet another embodiment, a reference sample is obtained from a healthy and/or non-diseased part of the body (e.g., tissues or cells) of an individual who is not the subject or patient. In even another embodiment, a reference sample is obtained from an untreated tissue and/or cell part of the body of an individual who is not the subject or patient.

"A TNFα inhibitor" or "a TNFα antagonist" refers to any molecule that inhibits one or more biological activities or blocking binding of TNFα with one or more of its associated molecules (e.g., TNFα receptor I (TNF-RI) or TNFα receptor II (TNF-RII)). Inhibitors of the invention can be used to modulate one or more aspects of TNFα associated effects, including but not limited to, for example, ligation with TNF-RI, followed by NF-κB activation, cytotoxicity, and induction of proinflammatory cytokines and chemokines as well as antiapoptotic peptides; ligation with TNF-RII inducing a costimulatory signal to TCR-mediated T cell activation, thereby increasing T cell proliferation, expression of T cell activation markers (CD25, human leukocyte antigen-DR, and TNF-RII), and secretion of inflammatory cytokines including IFNγ and TNFα; activation and expansion of protective CD4(+)FoxP3(+) regulatory T cells (Tregs), etc. These effects can be modulated by any biologically relevant mechanism, including disruption of binding to TNF-RI and/or TNF-RII, and/or by disrupting association between the ligand-receptor complex with other effector molecules. In certain embodiments, the TNFα inhibitor is a small molecule antagonist of TNFα, anti-sense TNFα, or siRNA or miRNA targeting TNFα. In certain embodiments, the TNFα inhibitor is an anti-TNFα antibody (or an antigen binding fragment thereof). In one embodiment, the anti-TNFα antibody is a humanized anti-TNFα antibody or an antigen binding fragment thereof. More specifically, the antibody is a recombinant humanized monoclonal anti-TNFα antibody (or rhuMAbTNFα). In some embodiments, the anti-TNFα antibodies of the present invention are anti-TNFα antagonistic antibodies that inhibit or block the binding of TNFα with TNF-RI and/or TNF-RII. Alternately and additionally, the TNFα inhibitors may include other TNFα-binding molecules, e.g., etanercept, including TNFα-binding fragments thereof.

In some embodiments, the TNFα inhibitor is an antibody selected from the group consisting of infliximab, adalimumab, golimumab and certolizumab pegol, or an antigen-binding fragment thereof.

Infliximab is a chimeric anti-TNF monoclonal antibody composed of human constant and murine variable regions. Adalimumab is a fully human monoclonal IgG1 anti-TNF antibody. Both have been clinically noted for their efficacy in controlling disease etiology and inducing clinical remission and mucosal healing in luminal CD and UC associated with both children and adult patients (Danese et al., *Alimentary Pharmacology & Therapeutics*, vol. 37, no. 9, pp. 855-866, 2013). Moreover several studies established the use of infliximab and adalimumab in active fistulizing CD in adult patients (Sands et al., *Clinical Gastroenterology and Hepatology*, vol. 2, no. 10, pp. 912-920, 2004; Colombel et al., *Gastroenterology*, vol. 132, no. 1, pp. 52-65, 2007). Certolizumab is a polyethylene-glycolated Fab' fragment of anti-TNF antibody, also produced significant clinical benefit and mucosal healing in adult patients with CD (Schreiber et al., *Gastroenterology*, vol. 129, pp. 807-818, 2005). Golimumab is a fully human monoclonal antibody to TNFα, was shown to induce and maintain clinical response in patients with active moderate-to-severe UC (Sandborn et al., *Gastroenterology*, vol. 146, no. 1, pp. 85-95, 2014).

Janus kinase inhibitors, also known as JAK inhibitors or jakinibs, are a type of medication that functions by inhibiting the activity of one or more of the Janus kinase family of enzymes (JAK1, JAK2, JAK3, TYK2), thereby interfering with the JAK-STAT signaling pathway. These inhibitors have therapeutic application in the treatment of cancer and inflammatory diseases such as rheumatoid arthritis.

In some embodiments, the JAK inhibitor is selected from ruxolitinib, tofacitinib (tasocitinib; CP-690550), upadacitinib (ABT-494), baricitinib (LY3009104, INCB28050), CYT387, Filgotinib (GLPG0634), lestaurtinib, pacritinib (SB1518), JSI-124, and CHZ868, or a combination thereof.

In one embodiment, the biomarkers (e.g., cytokines/chemokines/inflammatory mediators related to IBD or treatment thereof) are detected in an intestinal mucosal sample obtained from the subject. In another embodiment, the biomarkers are detected in a biopsy obtained from an affected area of an inflamed intestinal mucosa.

Yet in another embodiment, the biomarkers are detected in a blood sample, a stool sample, or an (intestinal) luminal wash obtained from the subject.

"Gastrointestinal inflammatory disorders" are a group of chronic disorders that cause inflammation and/or ulceration in the mucous membrane. These disorders include, for example, inflammatory bowel disease (e.g., Crohn's disease, ulcerative colitis, indeterminate colitis and infectious colitis), mucositis (e.g., oral mucositis, gastrointestinal mucositis, nasal mucositis and proctitis), necrotizing enterocolitis and esophagitis.

"Inflammatory Bowel Disease" or "IBD" is used interchangeably herein to refer to diseases of the bowel that cause inflammation and/or ulceration and includes without limitation Crohn's disease and ulcerative colitis.

"Crohn's disease (CD)" and "ulcerative colitis (UC)" are chronic inflammatory bowel diseases of unknown etiology. Crohn's disease, unlike ulcerative colitis, can affect any part of the bowel. The most prominent feature Crohn's disease is the granular, reddish-purple edematous thickening of the bowel wall. With the development of inflammation, these granulomas often lose their circumscribed borders and integrate with the surrounding tissue. Diarrhea and obstruction of the bowel are the predominant clinical features. As with ulcerative colitis, the course of Crohn's disease may be continuous or relapsing, mild or severe, but unlike ulcerative colitis, Crohn's disease is not curable by resection of the involved segment of bowel. Most patients with Crohn's disease require surgery at some point, but subsequent relapse is common and continuous medical treatment is usual.

Crohn's disease may involve any part of the alimentary tract from the mouth to the anus, although typically it appears in the ileocolic, small-intestinal or colonic-anorectal regions. Histopathologically, the disease manifests by discontinuous granulomatomas, crypt abscesses, fissures and aphthous ulcers. The inflammatory infiltrate is mixed, consisting of lymphocytes (both T and B cells), plasma cells, macrophages, and neutrophils. There is a disproportionate increase in IgM- and IgG-secreting plasma cells, macrophages and neutrophils.

The aforementioned therapeutic embodiments may be performed in instances wherein the TNFα inhibitor is used in combination with a second therapeutic molecule for the treatment of IBD. Representative examples of such secondary agents include, for example, anti-inflammatory drugs sulfasalazine and 5-aminosalisylic acid (5-ASA), which are used for treating mildly active colonic Crohn's disease and are commonly prescribed in an attempt to maintain remission of the disease. Metronidazole and ciprofloxacin are similar in efficacy to sulfasalazine and are particularly prescribed for treating perianal disease. In more severe cases, corticosteroids are prescribed to treat active exacerbations and can sometimes maintain remission. Azathioprine and 6-mercaptopurine have also been used in patients who require chronic administration of corticosteroids. It has been suggested that these drugs may play a role in the long-term prophylaxis. Other examples of secondary therapeutic agents include, for example, antidiarrheal drugs. The secondary agents may include nutritional therapy or elemental diet, optionally together with antibiotics for treating secondary small bowel bacterial overgrowth and/or pyogenic complications.

"Ulcerative colitis (UC)" afflicts the large intestine. The course of the disease may be continuous or relapsing, mild or severe. The earliest lesion is an inflammatory infiltration with abscess formation at the base of the crypts of Lieberkuhn. Coalescence of these distended and ruptured crypts tends to separate the overlying mucosa from its blood supply, leading to ulceration. Symptoms of the disease include cramping, lower abdominal pain, rectal bleeding, and frequent, loose discharges consisting mainly of blood, pus and mucus with scanty fecal particles. A total colectomy may be required for acute, severe or chronic, unremitting ulcerative colitis.

The clinical features of UC are highly variable, and the onset may be insidious or abrupt, and may include diarrhea, tenesmus and relapsing rectal bleeding. With fulminant involvement of the entire colon, toxic megacolon, a life-threatening emergency, may occur. Extra-intestinal manifestations include arthritis, pyoderma gangrenoum, uveitis, and erythema nodosum.

Treatment for UC includes sulfasalazine and related salicylate-containing drugs for mild cases and corticosteroid drugs in severe cases. Topical administration of either salicylates or corticosteroids is sometimes effective, particularly when the disease is limited to the distal bowel, and is associated with decreased side effects compared with systemic use. Supportive measures such as administration of iron and antidiarrheal agents are sometimes indicated. Azathioprine, 6-mercaptopurine and methotrexate are sometimes also prescribed for use in refractory corticosteroid-dependent cases.

An "effective dosage" refers to an amount effective, at dosages and for periods of time necessary, to achieve the desired therapeutic or prophylactic result.

As used herein, the term "subject" or "patient" refers to any single subject for which treatment is desired. A "subject" herein is typically a human subject. In certain embodiments, a subject is a non-human mammal. Exemplary non-human mammals include laboratory, domestic, pet, sport, and stock animals, e.g., mice, cats, dogs, horses, and cows. In other embodiments, the subject is a fowl, e.g., chicken. Typically, the subject is eligible for treatment, e.g., treatment of a gastrointestinal inflammatory disorder.

For the purposes herein, "tumor necrosis factor-alpha (TNF-alpha)" refers to a human TNF-alpha molecule comprising the amino acid sequence as known in the art, such as Pennica et al., Nature, 312:721 (1984) or Aggarwal et al., JBC, 260:2345 (1985).

A "TNF-α inhibitor" herein is an agent that inhibits, to some extent, a biological function of TNFα, generally through binding to TNFα and neutralizing its activity. Examples of TNF inhibitors specifically contemplated herein are etanercept (ENBREL®), infliximab (REMICADE®), adalimumab (HUMIRA®), golimumab (SIMPONI™), and certolizumab pegol (CIMZIA®), including biosimilars thereof. Preferably, the TNF-α inhibitor is an antibody which binds with specificity to TNF-α and prevents interaction of the TNF-α to its receptor(s) and/or other effector(s).

The terms "antibody" and "immunoglobulin" are used interchangeably in the broadest sense and include monoclonal antibodies (for example, full length or intact monoclonal antibodies), polyclonal antibodies, multivalent antibodies, multispecific antibodies (e.g., bispecific antibodies so long as they exhibit the desired biological activity) and may also include certain antibody fragments (as described in greater detail herein). An antibody can be human, humanized and/or affinity matured.

"Antibody fragments" comprise only a portion of an intact antibody, wherein the portion preferably retains at least one, and typically most or all, of the functions normally associated with that portion when present in an intact antibody. In one embodiment, an antibody fragment comprises an antigen binding site of the intact antibody and thus retains the ability to bind antigen. In another embodiment, an antibody fragment, for example one that comprises the Fc region, retains at least one of the biological functions normally associated with the Fc region when present in an intact antibody, such as FcRn binding, antibody half-life modulation, ADCC function and complement binding. In one embodiment, an antibody fragment is a monovalent antibody that has an in vivo half-life substantially similar to an intact antibody. For example, such an antibody fragment may comprise on antigen binding arm linked to an Fc sequence capable of conferring in vivo stability to the fragment.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigen. Furthermore, in contrast to polyclonal antibody preparations that typically include different antibodies directed against different determinants (epitopes), each monoclonal antibody is directed against a single determinant on the antigen.

The monoclonal antibodies herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; and Morrison et al., Proc. Natl. Acad. Sci. USA 81:6851-6855 (1984)).

"Humanized" forms of non-human (e.g., murine) antibodies are chimeric antibodies that contain minimal sequence derived from non-human immunoglobulin. For the most part, humanized antibodies are human immunoglobulins (recipient antibody) in which residues from a hypervariable region of the recipient are replaced by residues from a hypervariable region of a non-human species (donor antibody) such as mouse, rat, rabbit or nonhuman primate having the desired specificity, affinity, and capacity. In some instances, framework region (FR) residues of the human immunoglobulin are replaced by corresponding non-human residues. Furthermore, humanized antibodies may comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FRs are those of a human immunoglobulin lo sequence. The humanized antibody optionally will also comprise at least a portion of an immunoglobulin constant region (Fc), typically that of a human immunoglobulin. For further details, see Jones et al., Nature 321:522-525 (1986); Riechmann et al., Nature 332:323-329 (1988); and Vaswani and Hamilton, Ann. Allergy, Asthma & Immunol. 1: 105-115 (1998) and Hurle et al., Curr. Op. Biotech. 5:428-433 (1994).

A "human antibody" is one which comprises an amino acid sequence corresponding to that of an antibody produced by a human and/or has been made using any of the techniques for making human antibodies as disclosed herein. Such techniques include screening human-derived combinatorial libraries, such as phage display libraries (see, e.g., Marks et al., J. Mol. Biol., 222: 581-597 (1991) and Hoogenboom et al., Nucl. Acids Res., 19: 4133-4137 (1991)); using human myeloma and mouse-human heteromyeloma cell lines for the production of human monoclonal antibodies (see, e.g., Kozbor J. Immunol., 133: 3001 (1984); Brodeur et al., Monoclonal Antibody Production Techniques and Applications, pp. 55-93 (Marcel Dekker, Inc., New York, 1987); and Boerner et al., J. Immunol., 147:86 (1991)); and generating monoclonal antibodies in transgenic animals (e.g., mice) that are capable of producing a full repertoire of human antibodies in the absence of endogenous immunoglobulin production (see, e.g., Jakobovits et al., Proc. Natl. Acad. Sci USA, 90:2551 (1993); Jakobovits et al., Nature, 362:255 (1993); Bruggermann et al., Year in Immunol., 7: 33 (1993)). This definition of a human antibody specifically excludes a humanized antibody comprising antigen-binding residues from a non-human animal.

An "isolated" and/or "purified" antibody is one which has been identified and separated and/or recovered from a component of its natural environment. Contaminant components of its natural environment are materials which would interfere with diagnostic or therapeutic uses for the antibody, and may include enzymes, hormones, and other proteinaceous or nonproteinaceous solutes. In certain embodiments, the antibody will be purified (1) to greater than 95% by weight of antibody as determined by the Lowry method, and often more than 99% by weight, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie blue or silver stain. Isolated antibody includes the antibody in situ within recombinant cells since at least one component of the antibody's natural environment will not be present. Ordinarily, however, isolated antibody will be prepared by at least one purification step. The purified antibodies have a purity of at least 50%, at least 60%, at least 70%, at least 80%, at least 90%, at least 95%, or more. Methods for determining purity are known in the art.

An "affinity matured" antibody is one with one or more alterations in one or more CDRs thereof which result in an improvement in the affinity of the antibody for antigen, compared to a parent antibody which does not possess those alteration(s). In certain embodiments, affinity matured antibodies will have nanomolar or even picomolar affinities for the target antigen. Affinity matured antibodies are produced by procedures known in the art. Marks et al. Bio/Technology 10:779-783 (1992) describes affinity maturation by VH and VL domain shuffling. Random mutagenesis of CDR and/or framework residues is described by: Barbas et al. Proc Nat. Acad. Sci, USA 91:3809-3813 (1994); Schier et al. Gene 169:147-155 (1996); Yelton et al. J. Immunol. 155:1994-2004 (1995); Jackson et al., J. Immunol. 154(7):3310-9 (1995); and Hawkins et al. J. Mol. Biol. 226:889-896 (1992).

"Binding affinity" generally refers to the strength of the sum total of noncovalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant (Kd). Affinity can be measured by common methods known in the art, including those described herein. Low-affinity antibodies generally bind antigen slowly and tend to dissociate readily, whereas high-affinity antibodies generally bind antigen faster and tend to remain bound longer. A variety of methods of measuring binding affinity are known in the art, any of which can be used for purposes of the present invention.

Further embodiments relate to use of antigen-binding antibody fragments. Methods for generating such fragments starting from, for example, full-length immunoglobulins are known in the art. The terms "full-length antibody," "intact antibody," and "whole antibody" are used herein interchangeably to refer to an antibody in its substantially intact form, not antibody fragments as defined below. The terms particularly refer to an antibody with heavy chains that contain an Fc region.

A "naked antibody" for the purposes herein is an antibody that is not conjugated to a cytotoxic moiety or radiolabel.

Antibody fragments may be generated using enzymatic digestion, e.g., with pepsin and/or papain. For instance, the Fab fragment containing the constant domain of the light chain and the first constant domain (CH1) of the heavy chain may be generated using this method. Fab' fragments differ from Fab fragments by the addition of a few residues at the carboxy terminus of the heavy chain CH1 domain including one or more cysteines from the antibody hinge region. Fab'-SH is the designation herein for Fab' in which the cysteine residue(s) of the constant domains bear at least one free thiol group. F(ab')2 antibody fragments originally were produced as pairs of Fab' fragments which have hinge cysteines between them. Other chemical couplings of antibody fragments are also known. "Single-chain Fv" or "scFv" antibody fragments comprise the VH and VL domains of antibody, wherein these domains are present in a single polypeptide chain. In certain embodiments, the Fv polypeptide further comprises a polypeptide linker between the VH and VL domains which enables the scFv to form the desired structure for antigen binding. For a review of scFv see Plückthun in The Pharmacology of Monoclonal Antibodies, vol. 113, Rosenburg and Moore eds., Springer-Verlag, New York, pp. 269-315 (1994). HER2 antibody scFv fragments are described in WO93/16185; U.S. Pat. Nos. 5,571,894; and 5,587,458.

The term "Fc region" herein is used to define a C-terminal region of an immunoglobulin heavy chain, including native sequence Fc regions and variant Fc regions. Although the boundaries of the Fc region of an immunoglobulin heavy chain might vary, the human IgG heavy chain Fc region is usually defined to stretch from an amino acid residue at position Cys226, or from Pro230, to the carboxyl-terminus thereof. The C-terminal lysine (residue 447 according to the EU numbering system) of the Fc region may be removed, for example, during production or purification of the antibody, or by recombinantly engineering the nucleic acid encoding a heavy chain of the antibody. Accordingly, a composition of intact antibodies may comprise antibody populations with all K447 residues removed, antibody populations with no K447 residues removed, and antibody populations having a mixture of antibodies with and without the K447 residue.

Unless indicated otherwise, herein the numbering of the residues in an immunoglobulin heavy chain is that of the EU index as in Kabat et al., Sequences of Proteins of Immunological Interest, 5th Ed. Public Health Service, National Institutes of Health, Bethesda, Md. (1991), incorporated herein by reference. The "EU index as in Kabat" refers to the residue numbering of the human IgG1 EU antibody.

A "functional Fc region" possesses an "effector function" of a native sequence Fc region. Exemplary "effector functions" include C1q binding; complement dependent cytotoxicity; Fc receptor binding; antibody-dependent cell-mediated cytotoxicity (ADCC); phagocytosis; down regulation of cell surface receptors (e.g., B cell receptor; BCR), etc. Such effector functions generally require the Fc region to be combined with a binding domain (e.g., an antibody variable domain) and can be assessed using various assays as herein disclosed, for example.

A "native sequence Fc region" comprises an amino acid sequence identical to the amino acid sequence of an Fc region found in nature. Native sequence human Fc regions include a native sequence human IgG1 Fc region (non-A and A allotypes); native sequence human IgG2 Fc region; native sequence human IgG3 Fc region; and native sequence human IgG4 Fc region as well as naturally occurring variants thereof.

A "variant Fc region" comprises an amino acid sequence which differs from that of a native sequence Fc region by virtue of at least one amino acid modification. In certain embodiments, the variant Fc region has at least one amino acid substitution compared to a native sequence Fc region or to the Fc region of a parent polypeptide, e.g., from about one to about ten amino acid substitutions, and in certain embodiments from about one to about five amino acid substitutions in a native sequence Fc region or in the Fc region of the parent polypeptide. In certain embodiments, the variant Fc region herein will possess at least about 80% homology with a native sequence Fc region and/or with an Fc region of a parent polypeptide, or at least about 90% homology therewith, or at least about 95% homology therewith.

"Antibody-dependent cell-mediated cytotoxicity" and "ADCC" refer to a cell-mediated reaction in which nonspecific cytotoxic cells that express Fc receptors (FcRs) (e.g. Natural Killer (NK) cells, neutrophils, and macrophages) recognize bound antibody on a target cell and subsequently cause lysis of the target cell. The primary cells for mediating ADCC, NK cells, express FcγRIII only, whereas monocytes express FcγRI, FcγRII and FcγRIII FcR expression on hematopoietic cells in summarized is Table 3 on page 464 of Ravetch and Kinet, Annu. Rev. Immunol 9:457-92 (1991). To assess ADCC activity of a molecule of interest, an in vitro ADCC assay, such as that described in U.S. Pat. No. 5,500,362 or 5,821,337 may be performed. Useful effector cells for such assays include peripheral blood mononuclear cells (PBMC) and Natural Killer (NK) cells. Alternatively, or additionally, ADCC activity of the molecule of interest may be assessed in vivo, e.g., in an animal model such as that disclosed in Clynes et al. PNAS (USA) 95:652-656 (1998).

The terms "Fc receptor" or "FcR" are used to describe a receptor that binds to the Fc region of an antibody. In certain embodiments, FcR is a native sequence human FcR. Moreover, FcR is one which binds an IgG antibody (a gamma receptor) and includes receptors of the FcγRI, FcγRII, and FcγRIII subclasses, including allelic variants and alternatively spliced forms of these receptors. FcγRII receptors include FcγRIIA (an "activating receptor") and FcγRIIB (an "inhibiting receptor"), which have similar amino acid sequences that differ primarily in the cytoplasmic domains thereof. Activating receptor FcγRIIA contains an immunoreceptor tyrosine-based activation motif (ITAM) in its cytoplasmic domain. Inhibiting receptor FcγRIIB contains an immunoreceptor tyrosine-based inhibition motif (ITIM) in its cytoplasmic domain (see review in Daeron, Annu. Rev. Immunol. 15:203-234 (1997) and de Haas et al., J. Lab. Clin. Med. 126:330-41 (1995)). Other FcRs, including the neonatal receptor, FcRn, which is responsible for the transfer of maternal IgGs to the fetus (Kim et al., J. Immunol. 24:249 (1994)) are also included. Antibodies with improved binding to the Fc receptor (FcRn), and increased half-lives, are described in WO00/42072 and US2005/0014934.

The term antibody further includes diabodies, triabodies, tetrabodies and the like. The term "diabodies" refers to small antibody fragments with two antigen-binding sites, which fragments comprise a variable heavy domain (VH) connected to a variable light domain (VL) in the same polypeptide chain (VH-VL). By using a linker that is too short to allow pairing between the two domains on the same chain, the domains are forced to pair with the complementary domains of another chain and create two antigen-binding sites. Diabodies are described more fully in, for example, EP 404,097; WO 93/11161; and Hollinger et al., Proc. Natl. Acad. Sci. USA, 90:6444-6448 (1993). Triabodies, tetrabodies, and pentabodies, etc. which respectively include three, four, or five, or more antigen-binding sites, may be similarly generated.

The term antibody may further include variant antibodies. An "amino acid sequence variant" antibody herein is an antibody with an amino acid sequence which differs from a main species antibody. In certain embodiments, amino acid sequence variants will possess at least about 70% homology with the main species antibody, or they will be at least about 80%, or at least about 90% or more than 90% homologous with the main species antibody. The amino acid sequence variants possess substitutions, deletions, and/or additions at certain positions within or adjacent to the amino acid sequence of the main species antibody. Examples of amino acid sequence variants herein include an acidic variant (e.g., deamidated antibody variant), a basic variant, an antibody with an amino-terminal leader extension (e.g. VHS-) on one or two light chains thereof, an antibody with a C-terminal lysine residue on one or two heavy chains thereof, etc., and includes combinations of variations to the amino acid sequences of heavy and/or light chains. The antibody variant of particular interest herein is the antibody comprising an amino-terminal leader extension on one or two light chains thereof, optionally further comprising other amino acid sequence and/or glycosylation differences relative to the main species antibody.

A "glycosylation variant" antibody herein is an antibody with one or more carbohydrate moieties attached thereto which differ from one or more carbohydrate moieties attached to a main species antibody. Examples of glycosylation variants herein include antibody with a G1 or G2 oligosaccharide structure, instead a G0 oligosaccharide structure, attached to an Fc region thereof, antibody with one or two carbohydrate moieties attached to one or two light chains thereof, antibody with no carbohydrate attached to one or two heavy chains of the antibody, etc, and combinations of glycosylation alterations. Where the antibody has an Fc region, an oligosaccharide structure may be attached to one or two heavy chains of the antibody, e.g., at residue 299 (298 per EU numbering).

Any sample may be employed in the detection of the biomarker. The sample may be a sample which is derived from a patient. Such samples include, but are not limited to, sputum, blood, blood cells (e.g., white blood cells), tissue or biopsy samples (e.g., intestinal biopsy) or cultures thereof or supernatant of a culture thereof, urine, peritoneal fluid, and pleural fluid, or cells therefrom. Biological samples may also include sections of tissues such as frozen sections taken for histological purposes.

In one embodiment, the biomarkers are detected in an intestinal mucosal sample obtained from the subject. In another embodiment, the biomarkers are detected in a biopsy obtained from an affected area of an inflamed intestinal mucosa. Yet in another embodiment, the biomarkers are detected in a blood sample, a stool sample, or an (intestinal) luminal wash obtained from the subject.

The term "serum sample" refers to any serum sample obtained from an individual. Methods for obtaining sera from mammals are well known in the art. The term "whole blood" refers to any whole blood sample obtained from an individual. Typically, whole blood contains all of the blood components, e.g., cellular components and plasma. Methods for obtaining whole blood from mammals are well known in the art.

Subjects

Embodiments of the instant invention relate to the treatment of a variety of subjects. In one embodiment, the instant invention provides a method for treating a treatment-naïve subject having IBD with a TNFα inhibitor (or JAK inhibitor). In these embodiments, the treatment-naïve subject is a subject who has never undergone any form of therapy for the IBD. In another embodiment, the treatment naïve subject is a subject who has not previously undergone therapy for IBD with a biological agent. Representative examples of biological agents include, for example, etanercept, infliximab, adalimumab, golimumab, and certolizumab pegol, or a combination thereof.

In one embodiment, the biological agent is an anti-TNFα antibody selected from the group consisting of infliximab, adalimumab, golimumab and certolizumab pegol, or antigen-binding fragment thereof. In another embodiment, the biological agent is a TNFα-binding protein selected from the group consisting of etanercept. In another embodiment, the treatment-naïve subject is a subject who has previously undergone therapy for IBD with a steroid, an immunomodulator, or a combination thereof, but not with one or more of the aforementioned biological agents.

In another embodiment, the biological agent is a JAK inhibitor, which inhibits one or more of the Janus kinase family of enzymes (JAK1, JAK2, JAK3, TYK2), thereby interfering with the JAK-STAT signaling pathway. Representative examples of JAK inhibitors include, e.g., ruxolitinib, tofacitinib (tasocitinib; CP-690550), upadacitinib (ABT494), baricitinib (LY3009104, INCB28050), CYT387, filgotinib (GLPG0634), lestaurtinib, pacritinib (SB1518), JSI-124, and CHZ868, or a combination thereof.

The term "steroid" includes any organic molecule comprising four fused rings that assumes a three-dimensional shape. The term preferably includes corticosteroids, and synthetic derivatives thereof.

"Immunomodulators," as used herein are chemical agents that modify the immune response or the functioning of the immune system (as by the stimulation of antibody formation or the inhibition of white blood cell activity). Representative examples include as methotrexate or azathioprine.

In another embodiment, the instant invention provides a method for treating a subject having IBD who has previously undergone therapy with a TNFα inhibitor. In one embodiment, the subject has previously undergone therapy with an anti-TNFα antibody or antigen-binding fragment thereof, selected from the group consisting of infliximab, adalimumab, golimumab and certolizumab pegol, or antigen-binding fragment thereof. In other embodiments, the subject has previously undergone therapy with a cytotoxic agent or a cytostatic agent.

In one embodiment, the instant invention provides a method for treating a subject having IBD who has previously undergone therapy with an anti-TNFα antibody or antigen-binding fragment thereof and who is in remission from treatment with the anti-TNFα antibody or antigen-binding fragment thereof. In a related embodiment, the instant invention provides a method for treating a subject having IBD who has previously undergone therapy with an anti-TNFα antibody or antigen-binding fragment thereof and who is refractory or non-responsive to the anti-TNFα antibody or antigen-binding fragment thereof.

In yet another embodiment, the instant invention provides a method for treating a subject having IBD who has previously undergone therapy with an anti-TNFα antibody or antigen-binding fragment thereof and who is in remission from treatment with the anti-TNFα antibody or antigen-binding fragment thereof and who is undergoing or has undergone treatment with a second agent selected from the group consisting of vedolizumab, tofacitinib and ustekinumab, or a combination thereof.

The term "cytotoxic agent" as used herein refers to a substance that inhibits or prevents the function of cells and/or causes destruction of cells. The term is intended to include radioactive isotopes (e.g. At211, I131, I125, Y90, Re186, Sm153, Bi212, P32 and radioactive isotopes of Lu), chemotherapeutic agents, and toxins such as small molecule toxins or enzymatically active toxins of bacterial, fungal, plant or animal origin, including fragments and/or variants thereof.

Additional Indicators

In yet another embodiment, the instant invention provides a method for treating a subject having IBD with a TNFα inhibitor, comprising determining a severity of the IBD in the subject; determining a level of one or more (e.g., 3 or more) biomarkers selected from the group consisting of GM-CSF, IFNγ, IL-10, IL-12p70, IL-12p40, IL-1β, IL-2, IL-4, IL-5, IL-6, IL-7, IL-8, IL-13, IL-17A, MCP-1, and TNFα, or a fragment thereof, in a sample obtained from the subject (e.g., ex vivo explant culture of a tissue biopsy), in the presence and absence of a TNFα inhibitor; and administering to the subject the TNFα inhibitor if the level of the one or more (e.g., 3 or more) protein biomarkers is lower in the presence of the TNFα inhibitor as compared to a level of the biomarker in the absence of the TNF-α inhibitor. In certain embodiments, the biomarker is selected from a group consisting of IL-17A, IL-7, IL-5, IL-4 and IL-13, or a fragment thereof. In certain embodiments, the biomarkers determined to have cytokine down-regulation is one or more (e.g., 3 or more or all of) IL-17A, IL-7, IL-5, IL-4 and IL-13. In these embodiments, the disease severity may be determined via Harvey-Bradshaw index (HBI) method, endoscopy scoring method, or a combination thereof.

In some embodiments, the HBI is scored on a scale of 0-10, wherein an HBI score<5 indicates clinical remission (e.g., an HBI score of 0, 1, 2, 3, or 4). In these embodiments, an HBI score between 5-7 indicates mild disease (e.g., an HBI score of 5, 6, or 7). Similarly, in some embodiments, an HBI score>7 indicates severe disease (e.g., an HBI score of 8, 9, or 10).

In yet another embodiment, the endoscopy scoring is scored on a scale of 0-3, wherein, a score of 0 indicates no disease or remission, a score of 1 indicates mild disease with evidence of mild friability, reduced vascular pattern, and mucosal erythema; a score of 2 indicates moderate disease with friability, erosions, complete loss of vascular pattern, and significant erythema, and a score of 3 indicates severe disease with ulceration and spontaneous bleeding. Alternately, the other forms of endoscopy scoring, e.g., a scale of 0-5 or 0-10, may be used.

A combination of the HBI index and the endoscopy scoring may also be used.

Based on the HBI index and/or endoscopy scoring, the subject may be identified as having severe IBD, moderate IBD or mild IBD. In one embodiment, the invention relates to therapy of subjects with severe IBD. In another embodiment, the invention relates to therapy of subjects with moderate IBD. The HBI index and endoscopy scores may be incorporated into the instant methods using conventional approaches.

Another aspect of the invention provides a method for treating a subject having IBD with a TNFα inhibitor, comprising determining a level of one or more (e.g., 3 or more) biomarkers selected from the group consisting of IL-17A, IL-7, IL-5, IL-4 and IL-13, or a fragment thereof, in a sample obtained from the subject (e.g., ex vivo explant culture of a tissue biopsy), in the presence and absence of a TNFα inhibitor; determining a change in the level of the biomarker in the presence of the TNFα inhibitor versus in the absence of the TNFα inhibitor; administering to the subject the TNFα inhibitor if the level of the one or more (e.g., 3 or more) protein biomarkers is lower in the presence of the TNFα inhibitor as compared to a level of the biomarker in the absence of the TNF-α inhibitor; determining a severity of the IBD in the subject prior to and after administration of the TNF-α inhibitor; and correlating a change in the severity of IBD with a change in the biomarker level, wherein a positive correlation between the change in the severity of IBD and the change in the biomarker level indicates that the treatment with the TNFα inhibitor is effective.

In another embodiment, the method(s) further comprises performing a Receiver Operating Characteristic (ROC) analysis to evaluate the number of cytokines downregulated per patient ex vivo. The ROC analysis may be used as a predictor of clinical responses to anti-TNFα therapy (or anti-JAK therapy). The area under the curve (AUC) is measured and a cut-off value is used to compute optimal sensitivity and specificity.

Embodiments of the invention further relate to methods for the treatment of IBD comprising determining at least one or more of the aforementioned biomarkers together with another cytokine.

The term "cytokine" is a generic term for proteins released by one cell population which act on another cell as intercellular mediators. Examples of such cytokines are lymphokines, monokines, and traditional polypeptide hormones. Included among the cytokines are growth hormone such as human growth hormone, N-methionyl human growth hormone, and bovine growth hormone; parathyroid hormone; thyroxine; insulin; proinsulin; relaxin; prorelaxin; glycoprotein hormones such as follicle stimulating hormone (FSH), thyroid stimulating hormone (TSH), and luteinizing hormone (LH); hepatic growth factor; fibroblast growth factor; prolactin; placental lactogen; tumor necrosis factor-α and -β; mullerian-inhibiting substance; mouse gonadotropin-associated peptide; inhibin; activin; vascular endothelial growth factor; integrin; thrombopoietin (TPO); nerve growth factors such as NGF-β; platelet-growth factor; transforming growth factors (TGFs) such as TGF-α and TGF-β; insulin-like growth factor-I and -II; erythropoietin (EPO); osteoinductive factors; interferons such as interferon-α, -β, and -γ; colony stimulating factors (CSFs) such as macrophage-CSF (M-CSF); granulocyte-macrophage-CSF (GM-CSF); and granulocyte-CSF (G-CSF); interleukins (ILs) such as IL-1, IL-1α, IL-2, IL-3, IL-4, IL-5, IL-6, IL-7, IL-8, IL-9, IL-10, IL-11, IL-12; a tumor necrosis factor such as TNF-α or TNF-β; and other polypeptide factors including LIF and kit ligand (KL). As used herein, the term cytokine includes proteins from natural sources or from recombinant cell culture and biologically active equivalents of the native sequence cytokines. The term includes fragments and variants of any of the aforementioned cytokines.

Preferably, the cytokine that may be used in the methods of the invention is selected from the group consisting of granulocyte macrophage colony-stimulating factor (GM-CSF), interferon gamma (IFNγ), interleukin 10 (IL-10), interleukin 12 70-kDa (IL-12p70), interleukin 12 40-kDa (IL-12p40), interleukin 1 beta (IL-1β), interleukin 2 (IL-2), interleukin 4 (IL-4), interleukin 5 (IL-5), interleukin 6 (IL-6), interleukin 7 (IL-7), interleukin 8 (IL-8), interleukin 13 (IL-13), interleukin 17 (IL-17), monocyte chemoattractant protein-1 (MCP-1), and tumor necrosis factor alpha (TNFα), including a fragment thereof.

The instant invention further relates to methods for treating a subject having IBD comprising determining a level of one or more (e.g., 3 or more) biomarkers selected from the group consisting of IL-17A, IL-7, IL-5, IL-4 and IL-13, or a fragment thereof, in a sample obtained from the subject (e.g., ex vivo explant culture of a tissue biopsy), in the presence and absence of a tumor necrosis factor alpha (TNFα) inhibitor; and administering to the subject a composition comprising the TNFα inhibitor and a secondary agent if the level of the one or more (e.g., 3 or more) biomarkers is lower in the presence of the TNFα inhibitor as compared to a level of the biomarker in the absence of the TNF-α inhibitor, thereby treating the subject having IBD. In certain embodiments, the secondary agent is an immunosuppressive agent, a corticosteroid, a TNF antagonist, a cytostatic agent, a cytotoxic agent, or a combination thereof.

The term "immunosuppressive agent" as used herein for adjunct therapy refers to substances that act to suppress or mask the immune system of the subject being treated herein. This would include substances that suppress cytokine production, down-regulate or suppress self-antigen expression, or mask the MHC antigens. Examples of such agents include 2-amino-6-aryl-5-substituted pyrimidines (see U.S. Pat. No. 4,665,077); non-steroidal anti-inflammatory drugs (NSAIDs); ganciclovir; tacrolimus; glucocorticoids such as cortisol or aldosterone; anti-inflammatory agents such as a cyclooxygenase inhibitor; a 5-lipoxygenase inhibitor; or a leukotriene receptor antagonist; purine antagonists such as azathioprine or mycophenolate mofetil (MMF); alkylating agents such as cyclophosphamide; bromocryptine; danazol; dapsone; glutaraldehyde (which masks the MHC antigens, as described in U.S. Pat. No. 4,120,649); anti-idiotypic antibodies for MHC antigens and MHC fragments; cyclosporine; 6 mercaptopurine; steroids such as corticosteroids or glucocorticosteroids or glucocorticoid analogs, e.g., prednisone, methylprednisolone, including SOLU-MEDROL® methylprednisolone sodium succinate, and dexamethasone; dihydrofolate reductase inhibitors such as methotrexate (oral or subcutaneous); anti-malarial agents such as chloroquine and hydroxychloroquine; sulfasalazine; leflunomide; cytokine or cytokine receptor antibodies or antagonists including anti-interferon-alpha, -beta, or -gamma antibodies, anti-tumor necrosis factor(TNF)-alpha antibodies (infliximab (REMICADE®) or adalimumab), anti-TNF-alpha immunoadhesin (etanercept), anti-TNF-beta antibodies, anti-interleukin-2 (IL-2) antibodies and anti-IL-2 receptor antibodies, and anti-interleukin-6 (IL-6) receptor antibodies and antagonists; anti-LFA-1 antibodies, including anti-CD11a and anti-CD18 antibodies; anti-L3T4 antibodies; heterologous anti-lymphocyte globulin; pan-T antibodies, anti-CD3 or anti-CD4/CD4a antibodies; soluble peptide containing a LFA-3 binding domain (WO 90/08187 published Jul. 26, 1990); streptokinase; transforming growth factor-beta (TGF-beta); streptodomase; RNA or DNA from the host; FK506; RS-61443; chlorambucil; deoxyspergualin; rapamycin; T-cell receptor (Cohen et al., U.S. Pat. No. 5,114,721); T-cell receptor fragments (Offner et al., Science, 251: 430-432 (1991); WO 90/11294; Ianeway, Nature, 341: 482 (1989); and WO 91/01133); BAFF antagonists such as BAFF or BR3 antibodies or immunoadhesins and zTNF4 antagonists (for review, see Mackay and Mackay, Trends Immunol., 23:113-5 (2002) and see also definition below); biologic agents that interfere with T cell helper signals, such as anti-CD40 receptor or anti-CD40 ligand (CD154), including blocking antibodies to CD40-CD40 ligand. (e.g., Durie et. al., Science, 261: 1328-30 (1993); Mohan et al., J. Immunol., 154: 1470-80 (1995)) and CTLA4-Ig (Finck et al., Science, 265: 1225-7 (1994)); and T-cell receptor antibodies (EP 340,109) such as T10B9.

"Corticosteroid" refers to any one of several synthetic or naturally occurring substances with the general chemical structure of steroids that mimic or augment the effects of the naturally occurring corticosteroids. Examples of synthetic corticosteroids include prednisone, prednisolone (including methylprednisolone), dexamethasone triamcinolone, and betamethasone.

An "antagonist" or "inhibitor" refers to a molecule capable of neutralizing, blocking, inhibiting, abrogating, reducing or interfering with the activities of a particular or specified protein, including its binding to one or more receptors in the case of a ligand or binding to one or more ligands in case of a receptor. Antagonists include antibodies and antigen-binding fragments thereof, proteins, peptides, glycoproteins, glycopeptides, glycolipids, polysaccharides, oligosaccharides, nucleic acids, bioorganic molecules, peptidomimetics, pharmacological agents and their metabolites, transcriptional and translation control sequences, and the like. Antagonists also include small molecule inhibitors of the protein, and fusion proteins, receptor molecules and derivatives which bind specifically to the protein thereby sequestering its binding to its target, antagonist variants of the protein, antisense molecules directed to the protein, RNA aptamers, and ribozymes against the protein.

The term "attenuates" or "attenuation" as used herein refers to a decrease, reduction or elimination of a condition, disease, disorder, or phenotype, including an abnormality or symptom.

It is to be understood that the terminology "a combination of" two compounds or "combination therapy" does not mean that the compounds have to be administered in admixture with each other. Thus, treatment with or use of such a combination encompasses a mixture of the compounds or separate administration of the compounds, and includes administration on the same day or different days. Thus the terminology "combination" means two or more compounds are used for the treatment, either individually or in admixture with each other. When an antibody and a second compound, for example, are administered in combination to a subject, the antibody is present in the subject at a time when the second compound is also present in the subject, whether the antibody and second compound are administered individually or in admixture to the subject. In certain embodiments, a compound other than the antibody is administered prior to the antibody. In certain embodiments, a compound other than the antibody is administered after the antibody.

The aforementioned therapeutic embodiments are practiced using a therapeutically effective amount of the TNFα inhibitor and/or the secondary agent.

The expression "therapeutically effective amount" refers to an amount that is effective for preventing, ameliorating, or treating a disease or disorder (e.g., inflammatory bowel disease, e.g., ulcerative colitis or Crohn's disease). For example, a "therapeutically effective amount" of an antibody refers to an amount of the antibody that is effective for preventing, ameliorating, or treating the specified disease or disorder. Similarly, a "therapeutically effective amount" of a combination of an antibody and a second compound refers to an amount of the antibody and an amount of the second compound that, in combination, is effective for preventing, ameliorating, or treating the specified disease or disorder or a symptom thereof.

A "symptom" of a disease or disorder (e.g., inflammatory bowel disease, e.g., ulcerative colitis or Crohn's disease) is any morbid phenomenon or departure from the normal in structure, function, or sensation, experienced by a subject and indicative of disease.

Another aspect of the invention provides a method for treating a subject having inflammatory bowel disease (IBD) with a Janus kinase (JAK) inhibitor, comprising determining a level of one or more (e.g., 3 or more) biomarkers selected from the group consisting of interleukin 6 (IL-6), interleukin 8 (IL-8), MCP-1, TNFα, GM-CSF, IFNγ, IL-1β, or a fragment thereof, in a sample obtained from the subject (e.g., ex vivo explant culture of a tissue biopsy), in the presence and absence of a JAK inhibitor; and administering to the subject a composition comprising the JAK inhibitor if the level of the one or more (e.g., 3 or more) biomarkers is lower in the presence of the JAK inhibitor as compared to a level of the biomarker in the absence of the JAK inhibitor, thereby treating the subject having IBD.

In these embodiments, the JAK inhibitor can be a compound selected from the group consisting of ruxolitinib, tofacitinib (tasocitinib; CP-690550), upadacitinib (ABT494), baricitinib (LY3009104, INCB28050), CYT387, Filgotinib (GLPG0634), lestaurtinib, pacritinib (SB1518), JSI-124, and CHZ868, or a combination thereof.

II. Methods for Diagnosing (and Treatment)

In one embodiment, the instant invention relates to methods for determining whether a subject having inflammatory diseases will be responsive to treatment with a test compound for inflammatory disease treatment, such as a tumor necrosis factor alpha (TNFα) inhibitor or JAK inhibitor. Examples of such inflammatory diseases include, those mediated by TNFα, such as, inflammatory bowel disease (IBD), rheumatoid arthritis (RA) and psoriasis. Preferably, the diseases are characterized by presence of one or more disease markers, e.g., inflammatory cytokines, often in inflamed cells and/or tissues, e.g., biopsied material and the like. Particularly, the compositions and methods of the instant invention relate to determining whether a subject having IBD will be responsive to treatment with a TNFα inhibitor.

Thus one aspect of the invention provides a method for determining whether a subject having inflammatory bowel disease (IBD) will be responsive to treatment with a tumor necrosis factor alpha (TNFα) inhibitor (or JAK inhibitor), comprising determining a level of one or more (e.g., 3 or more) biomarkers selected from the group consisting of GM-CSF, IFNγ, IL-10, IL-12p'70, IL-12p40, IL-1β, IL-2, IL-4, IL-5, IL-6, IL-7, IL-8, IL-13, IL-17A, MCP-1, and TNFα, or a fragment thereof, in a sample obtained from the subject (e.g., ex vivo explant culture of a tissue biopsy), in the presence and absence of a TNFα inhibitor (or JAK inhibitor); wherein a decrease in a level of the one or more (e.g., 3 or more) biomarkers in the presence of the TNFα inhibitor (or JAK inhibitor) as compared to a level of the one or more (e.g., 3 or more) biomarkers in the absence of the TNFα inhibitor (or JAK inhibitor) indicates that the subject is responsive to treatment with the TNFα inhibitor (or JAK inhibitor), thereby determining whether a subject having IBD is responsive to treatment with the TNFα inhibitor (or JAK inhibitor).

In one embodiment, the method comprises determining a level of one or more (e.g., 3 or more) biomarkers selected from the group consisting of IL-17A, IL-7, IL-5, IL-4 and IL-13, or a fragment thereof. In another embodiment, the method comprises determining a level of one or more biomarkers selected from the group consisting of IL-6 and IL-8, or a combination thereof. A combination of the biomarkers, or a signature, may be employed.

In one embodiment, the method of determination relates to a diagnostic method. In another embodiment, the method of diagnostic relates to a prognostic method. The term "diagnosis" is used herein to refer to the identification or classification of a molecular or pathological state, disease or condition. For example, "diagnosis" may refer to identification of a particular type of IBD, e.g., UC or Crohn's disease. "Diagnosis" may also refer to the classification of a particular subtype of IBD, e.g., by histopathological criteria or by molecular features (e.g., a subtype characterized by expression of one or a combination of particular genes or proteins encoded by said genes). The term "aiding diagnosis" is used herein to refer to methods that assist in making a clinical determination regarding the presence, or nature, of a particular type of symptom or condition. For example, a method of aiding diagnosis of IBD can comprise measuring the expression of certain genes in a biological sample from an individual.

The term "prognosis" is used herein to refer to the prediction of the likelihood of autoimmune disorder-attributable disease symptoms of an autoimmune disease such as IBD. The term "prediction" is used herein to refer to the likelihood that a patient will respond either favorably or unfavorably to a drug (therapeutic agent) or set of drugs or a therapeutic regimen. In one embodiment, the prediction relates to the extent of those responses. In one embodiment, the prediction relates to whether and/or the probability that a patient will survive or improve following treatment, for example treatment with a particular therapeutic agent, or for a certain period of time without disease recurrence. The predictive methods of the invention can be used clinically to make treatment decisions by choosing the most appropriate treatment modalities for any particular patient. The predictive methods of the present invention are valuable tools in predicting if a patient is likely to respond favorably to a treatment regimen, such as a given therapeutic regimen, including for example, administration of a given therapeutic agent or combination, surgical intervention, steroid treatment, etc., or whether long-term survival of the patient or remission or sustained remission, following a therapeutic regimen is likely.

A "control subject" refers to a healthy subject who has not been diagnosed as having a particular disease, e.g., IBD, and who does not suffer from any sign or symptom associated with that disease.

By "correlate" or "correlating" is meant comparing, in any way, the performance and/or results of a first analysis or protocol with the performance and/or results of a second analysis or protocol. For example, one may use the results of a first analysis or protocol in carrying out a second protocols and/or one may use the results of a first analysis or protocol to determine whether a second analysis or protocol should be performed. With respect to the embodiment of gene expression analysis or protocol, one may use the results of the gene expression analysis or protocol to determine whether a specific therapeutic regimen should be performed.

The term "comparing" as used herein refers to comparing the level of the biomarker in the sample from the individual or patient with the reference level of the biomarker specified elsewhere in this description. It is to be understood that comparing as used herein usually refers to a comparison of corresponding parameters or values, e.g., an absolute amount is compared to an absolute reference amount while a concentration is compared to a reference concentration or an intensity signal obtained from the biomarker in a sample is compared to the same type of intensity signal obtained from a reference sample. The comparison may be carried out manually or computer assisted. Thus, the comparison may be carried out by a computing device (e.g., of a system disclosed herein). The value of the measured or detected level of the biomarker in the sample from the individual or patient and the reference level can be, e.g., compared to each other and the said comparison can be automatically carried out by a computer program executing an algorithm for the comparison. The computer program carrying out the said evaluation will provide the desired assessment in a suitable output format. For a computer assisted comparison, the value of the determined amount may be compared to values corresponding to suitable references which are stored in a database by a computer program. The computer program may further evaluate the result of the comparison, i.e. automatically provide the desired assessment in a suitable output format. For a computer assisted comparison, the value of the determined amount may be compared to values corresponding to suitable references which are stored in a database by a computer program. The computer program may further evaluate the result of the comparison, i.e. automatically provides the desired assessment in a suitable output format.

The phrase "recommending a treatment" as used herein refers to using the information or data generated relating to the level or presence of TNFα mRNA or protein, optionally together with any of the aforementioned biomarkers (e.g., GM-CSF, IFNγ, IL-10, IL-12p70, IL-12p40, IL-1β, IL-2, IL-4, IL-5, IL-6, IL-7, IL-8, IL-13, IL-17, MCP-1) in a sample of a patient to identify the patient as suitably treated or not suitably treated with a therapy. In some embodiment the therapy may comprise a TNFα inhibitor, including an anti-TNFα antibody such as infliximab, adalimumab, golimumab and certolizumab pegol, or antigen-binding fragment thereof. In some embodiments the phrase "recommending a treatment/therapy" includes the identification of a patient who requires adaptation of an effective amount of the TNFα inhibitor being administered. In some embodiments recommending a treatment includes recommending that the amount of TNFα inhibitor being administered is adapted.

The phrase "recommending a treatment" as used herein also may refer to using the information or data generated for proposing or selecting a therapy comprising a TNFα inhibitor for a patient identified or selected as more or less likely to respond to the therapy comprising a TNFα inhibitor. The information or data used or generated may be in any form, written, oral or electronic. In some embodiments, using the information or data generated includes communicating, presenting, reporting, storing, sending, transferring, supplying, transmitting, dispensing, or combinations thereof. In some embodiments, communicating, presenting, reporting, storing, sending, transferring, supplying, transmitting, dispensing, or combinations thereof are performed by a computing device, analyzer unit or combination thereof. In some further embodiments, communicating, presenting, reporting, storing, sending, transferring, supplying, transmitting, dispensing, or combinations thereof are performed by a laboratory or medical professional. In some embodiments, the information or data includes a comparison of the level of TNFα mRNA or protein to a reference level. In some embodiments, the information or data includes an indication that TNFα mRNA or protein (optionally together with a biomarker mRNA or protein) is present or absent in the sample. In some embodiments, the information or data includes an indication that the patient is suitably treated or not suitably treated with a therapy comprising a TNFα inhibitor, including an anti-TNFα antibody such as infliximab, adalimumab, golimumab and certolizumab pegol, or antigen-binding fragment thereof.

A "target" is a group of people or an institution to whom or to which a particular medicament is being promoted or intended to be promoted, as by marketing or advertising, especially for particular uses, treatments, or indications, such as individual patients, patient populations, readers of newspapers, medical literature, and magazines, television or internet viewers, radio or internet listeners, physicians, drug companies, etc.

The expression "not responsive to," "non-response" and grammatical variants thereof, as it relates to the reaction of subjects or patients to one or more of the medicaments (therapeutic agents) that were previously administered to them, describes those subjects or patients who, upon administration of such medicament(s), did not exhibit any or adequate signs of treatment of the disorder for which they were being treated, or they exhibited a clinically unacceptably high degree of toxicity to the medicament(s), or they did not maintain the signs of treatment after first being administered such medicament(s), with the word treatment being used in this context as defined herein. The phrase "not responsive" includes a description of those subjects who are resistant and/or refractory to the previously administered medication(s), and includes the situations in which a subject or patient has progressed while receiving the medicament(s) that he or she is being given, and in which a subject or patient has progressed within 12 months (for example, within six months) after completing a regimen involving the medicament(s) to which he or she is no longer responsive. The non-responsiveness to one or more medicaments thus includes subjects who continue to have active disease following previous or current treatment therewith. For instance, a patient may have active disease activity after about one to three months, or three to six months, or six to 12 months, of therapy with the medicament(s) to which they are non-responsive. Such responsiveness may be assessed by a clinician skilled in treating the disorder in question.

For purposes of non-response to medicament(s), a subject who experiences "a clinically unacceptably high level of toxicity" from previous or current treatment with one or more medicaments experiences one or more negative side-effects or adverse events associated therewith that are considered by an experienced clinician to be significant, such as, for example, serious infections, congestive heart failure, demyelination (leading to multiple sclerosis), significant hypersensitivity, neuropathological events, high degrees of autoimmunity, a cancer such as endometrial cancer, non-Hodgkin's lymphoma, breast cancer, prostate cancer, lung cancer, ovarian cancer, or melanoma, tuberculosis (TB), and the like.

The "amount" or "level" of a biomarker associated with an increased clinical benefit to a patient suffering from a certain disease or disorder, or predictive of response to a particular therapeutic agent or treatment regimen, is a detectable level in a biological sample. These can be measured by methods known to one skilled in the art and also disclosed herein. The expression level or amount of biomarker assessed can be used to determine the response or the predicted response to a treatment or therapeutic agent.

The terms "level of expression" or "expression level" in general are used interchangeably and generally refer to the amount of a polynucleotide or an amino acid product or protein in a biological sample. "Expression" generally refers to the process by which gene-encoded information is converted into the structures present and operating in the cell. Therefore, as used herein, "expression" of a gene may refer to transcription into a polynucleotide, translation into a protein, or even posttranslational modification of the protein. Fragments of the transcribed polynucleotide, the translated protein, or the post-translationally modified protein shall also be regarded as expressed whether they originate from a transcript generated by alternative splicing or a degraded transcript, or from a posttranslational processing of the protein, e.g., by proteolysis. "Expressed genes" include those that are transcribed into a polynucleotide as mRNA and then translated into a protein, and also those that are transcribed into RNA but not translated into a protein (for example, transfer and ribosomal RNAs).

As used herein, the phrase "detecting the level expression" includes methods that quantitate expression levels as well as methods that determine whether a protein of interest is expressed at all. Thus, an assay which provides a yes or no result without necessarily providing quantification of an amount of expression is an assay that requires "detecting the level of expression" as that phrase is used herein. The proteins identified as being differentially expressed in liver cancer may be used in a variety of proteomic assays to detect or quantititate the expression level of a proteins or multiple proteins in a given sample. For example, traditional antibody-based assays, 2D gel electrophoresis, ELISA assays, and the like. For differentially expressed genes, Northern blotting, nuclease protection, RT-PCR, in situ hybridization, sequencing, and differential display methods may be used. Those methods are useful for some embodiments of the invention. However, methods and assays of the invention are most efficiently designed with antibody array or chip-based methods.

The term "expression profile," which is used interchangeably herein with "protein expression profile" and "proteome" or proteomic signature of a cell refers to a set of values representing levels or activity of one or more proteins. An expression profile preferably comprises values representing expression levels of at least about two proteins, preferably at least about 2, 3, 5, 6 or more proteins. Expression profiles may also comprise a level of a protein which is expressed at similar levels in multiple cells and conditions (e.g., actin). For example, an expression profile of a diseased cell of colon in the context of IBD refers to a set of values representing protein levels of at least one control protein and 2 to 6 or more of the proteins in a diseased cell or tissue.

An expression profile in one cell is "similar" to an expression profile in another cell when the level of expression of the proteins in the two profiles are sufficiently similar that the similarity is indicative of a common characteristic, for example, the same type of cell. Accordingly, the expression profiles of a first cell and a second cell are similar when at least 75%, at least 80, at least 90%, at least 95% or more of the proteins that are expressed in the first cell are expressed in the second cell at a level that is within a factor of two relative to the first cell.

III. Other Related Methods

One aspect of the invention provides a method for quantifying an outcome of treatment of IBD with an anti-TNFα antibody or JAK inhibitor in a subject, comprising detecting and quantitating, in a sample obtained from the subject (e.g., ex vivo explant culture of a tissue biopsy), at least one (e.g., 3 or more) biomarker selected from the group consisting of GM-CSF, IFNγ, IL-10, IL-12p70, IL-12p40, IL-1β, IL-2, IL-4, IL-5, IL-6, IL-7, IL-8, IL-13, IL-17A, MCP-1, and TNFα, or a fragment thereof; and comparing a level of expression of the biomarker in the subject's sample with a reference standard, wherein a differential level of expression of the biomarker in the sample compared to the level of expression of the biomarker in the reference standard is indicative of the outcome of treatment of IBD with the anti-TNFα antibody or JAK inhibitor.

As used herein, unless otherwise specified, reduction in expression level refers to statistically significant reduction (e.g., $p<0.05$ or 0.01) based on applicable statistical analysis.

In one embodiment, the method comprises determining a level of one or more (e.g., 3 or more) biomarkers selected from the group consisting of IL-17A, IL-7, IL-5, IL-4 and IL-13, or a fragment thereof.

In another embodiment, the method comprises determining a level of one or more biomarkers selected from the group consisting of IL-6 and IL-8, or a combination thereof.

In these embodiments, the IBD is ulcerative colitis or Crohn's disease.

A "reference standard" can be any number of types of samples or method of determining a reference expression level for each protein, including normal plasma, serum, tissue or cells (e.g., ex vivo explant culture of a tissue biopsy, or supernatant thereof), the normal range from normal plasma, serum, or tissue, the range of expression within a group of patients, or a set of patients with a certain outcome. By "reference standard" it is meant a sample which provides a baseline for the assayed parameter (i.e., a control). Reference standards may comprise normal or non-inflamed cell/tissue sample isolated from a subject as well as cultured primary cells/tissues. Examples of reference standard include, but are not limited to, adjacent normal cells/tissues obtained from the same organ or body location of a patient, a sample isolated from a normal subject, a primary cells/tissues obtained from a depository (for example, American type tissue culture Accession No.: 87253 or 87254, which relate to human embryonic liver at 72 days and 58 days, respectively), etc. A reference standard can also be the expression level for a set of patients, such as a set of IBD patients, or for the set of IBD patients receiving a certain treatment (e.g. TNF-alpha antibodies) or for a set of patients with one outcome versus another outcome. In the former case the specific level of each patient can be assigned to a percentile level of expression, or expressed as either higher or lower than the mean or average. The term "reference standard" as used herein particularly includes normal cells, cells from patients treated with standard therapy, e.g., corticosteroids. A reference standard may also comprise a measured value for example, average/median level of expression of a particular gene in a population. Such a population may comprise normal subjects, patients with IBD who have not undergone any treatment (i.e., treatment naïve), IBD patients undergoing cytostatic therapy, IBD patients undergoing anti-TNF-alpha therapy other than anti-TNF-alpha antibodies or patients having non-irritable forms of the IBD. A "positive reference standard" or "positive control" as is known in the art, comprising, for example, biopsy samples obtained from IBD patients or positive histological samples (e.g., expressing the biomarkers) may be optionally employed.

In one embodiment, wherein the IBD is Crohn's disease, the following reference standards including one or more (e.g., all) of those listed below, which are tailored for biopsy samples obtained from intestinal mucosa, may be employed (values in parenthesis represent range of concentration of various biomarkers):

(a) IL-5: about 3.5 pg/ml (about 1.0-5.0 pg/ml);
(b) IL-7: about 8.2 pg/ml (about 5.0-10.0 pg/ml);
(c) IL-13: about 9.0 pg/ml (about 7.0-12.0 pg/ml);
(d) IL-2: about 11.0 pg/ml (about 8.0-15.0 pg/ml);
(e) TNF-α: about 20.0 pg/ml (about 15.0-25.0 pg/ml);
(f) IL-17A: about 22.0 pg/ml (about 18.0-26.0 pg/ml);
(g) IFNγ: about 28.0 pg/ml (about 25.0-32.0 pg/ml);
(h) IL-12p70: about 29.0 pg/ml (about 25.0-35.0 pg/ml);
(i) IL-1B: about 20.0 pg/ml (about 17.0-30.0 pg/ml);
(j) IL-4: about 29.0 pg/ml (about 25.0-35.0 pg/ml);
(k) IL-10: about 44.0 pg/ml (about 40.0-55.0 pg/ml);
(l) GM-CSF: about 55.0 pg/ml (about 45.0-60.0 pg/ml);
(m) IL-12p40: about 55.0 pg/ml (about 40.0-75.0 pg/ml);
(n) IL-6: about 700 pg/ml (about 500.0-800.0 pg/ml),
(o) MCP-1: about 900 pg/ml (about 700.0-1100.0 pg/ml; and
(p) IL-8: about 6000 pg/ml (about 4000.0-9000.0 pg/ml).

In another embodiment, wherein the IBD is Crohn's disease, the following reference standards including one or more (e.g., all) of those listed below, which are tailored for biopsy samples obtained from intestinal mucosa, may be employed (values in parenthesis represent range of concentration of various biomarkers):

(a) IL-5: about 2.1 pg/ml (about 1.0-4.0 pg/ml);
(b) IL-7: about 2.8 pg/ml (about 2.0-4.0 pg/ml);
(c) IL-13: about 5.0 pg/ml (about 3.0-7.0 pg/ml);
(d) IL-2: about 6.0 pg/ml (about 4.0-8.0 pg/ml);
(e) TNF-α: about 5.8 pg/ml pg/ml (about 4.0-8.0 pg/ml);
(f) IL-17A: about 20.0 pg/ml (about 17.0-24.0 pg/ml);
(g) IFNγ: about 9.8 pg/ml pg/ml (about 7.0-12.0 pg/ml);
(h) IL-12p70: about 29.0 pg/ml (about 25.0-35.0 pg/ml);

(i) IL-1B: about 4.6 pg/ml (about 3.0-7.0 pg/ml);
(j) IL-4: about 14.0 pg/ml (about 11.0-18.0 pg/ml);
(k) IL-10: about 12.0 pg/ml (about 10.0-15.0 pg/ml);
(l) GM-CSF: about 19.0 pg/ml (about 15.0-22.0 pg/ml);
(m) IL-12p40: about 34.0 pg/ml (about 30.0-45.0 pg/ml);
(n) IL-6: about 125 pg/ml (about 100.0-140.0 pg/ml),
(o) MCP-1: about 425 pg/ml (about 300.0-500.0 pg/ml); and
(p) IL-8: about 3000 pg/ml (about 2000.0-4000.0 pg/ml).

Another aspect of the invention provides a method for quantifying an outcome of treatment of Crohn's disease (CD) with an anti-TNFα antibody in a subject, comprising detecting and quantitating, in a sample obtained from the subject (e.g., ex vivo explant culture of a tissue biopsy), at least one (e.g., 3 or more) biomarker selected from the group consisting of GM-CSF, IFNγ, IL-10, IL-12p70, IL-12p40, IL-1β, IL-2, IL-4, IL-5, IL-6, IL-7, IL-8, IL-13, IL-17A, MCP-1, and TNFα, or a fragment thereof; and comparing a level of expression of the biomarker in the subject's sample with a reference standard, wherein a reduction in the level of expression of the biomarker in the sample compared to the level of expression of the biomarker in the reference standard is indicative of the outcome of treatment of CD with the anti-TNFα antibody.

In certain embodiments, the reference standard comprises about 3.5 pg/ml IL-5, about 8.2 pg/ml IL-7, about 9.0 pg/ml IL-13, about 11.0 pg/ml IL-2, about 20.0 pg/ml TNF-α, about 22.0 pg/ml IL-17A, about 28.0 pg/ml IFN, about 29.0 pg/ml IL-12p70, about 20.0 pg/ml IL-1B, about 29.0 pg/ml IL-4, about 44.0 pg/ml IL-10, about 55.0 pg/ml GM-CSF, about 55.0 pg/ml IL-12p40, about 700 pg/ml IL-6, about 900 pg/ml MCP-1 and about 6000 pg/ml IL-8.

Another aspect of the invention provides a method for quantifying an outcome of treatment of ulcerative colitis (UC) with an anti-TNFα antibody in a subject, comprising detecting and quantitating, in a sample obtained from the subject (e.g., ex vivo explant culture of a tissue biopsy), at least one (e.g., 3 or more) biomarker selected from the group consisting of GM-CSF, IFNγ, IL-10, IL-12p70, IL-12p40, IL-1β, IL-2, IL-4, IL-5, IL-6, IL-7, IL-8, IL-13, IL-17A, MCP-1, and TNFα, or a fragment thereof; and comparing a level of expression of the biomarker in the subject's sample with a reference standard, wherein a reduction in the level of expression of the biomarker in the sample compared to the level of expression of the biomarker in the reference standard is indicative of the outcome of treatment of UC with the anti-TNFα antibody.

In certain embodiments, the reference comprises about 2.1 pg/ml IL-5, about 2.8 pg/ml IL-7, about 5.0 pg/ml IL-13, about 6.0 pg/ml IL-2, about 5.8 pg/ml TNF-α, about 20.0 pg/ml IL-17A, about 9.8 pg/ml IFN, about 29.0 pg/ml IL-12p70, about 4.6 pg/ml IL-1B, about 14.0 pg/ml IL-4, about 12.0 pg/ml IL-10, about 19.0 pg/ml GM-CSF, about 34.0 pg/ml IL-12p40, about 125 pg/ml IL-6, about 425 pg/ml MCP-1 and about 3000 pg/ml IL-8.

Another aspect of the invention relates to a method for monitoring an effectiveness of an anti-tumor necrosis factor alpha (TNFα) antibody, or antigen-binding fragment thereof, comprising determining a level of one or more (e.g., 3 or more) biomarkers selected from the group consisting of interleukin 17A (IL-17A), interleukin 7 (IL-7), interleukin 5 (IL-5), interleukin 4 (IL-4) and interleukin 13 (IL-13), or a fragment thereof, in a sample obtained from the subject (e.g., ex vivo explant culture of a tissue biopsy) prior to the initiation of the treatment; determining the level of the one or more (e.g., 3 or more) biomarkers in a second sample(s) from the subject after at least a portion of the treatment has been administered; comparing the level of the one or more (e.g., 3 or more) biomarkers in the first sample(s) with a level of the one or more (e.g., 3 or more) biomarkers in the second sample(s), wherein a difference in the level of the one or more (e.g., 3 or more) markers in the first sample(s) as compared to the level of the one or more (e.g., 3 or more) markers in the second sample(s) indicates that the subject is responding to the treatment. Under these embodiments, in one instance, the response indicates remission of the IBD. In another instance, the response indicates stabilization of the IBD.

Another aspect of the invention relates to a method for monitoring an effectiveness of a JAK inhibitor, comprising determining a level of one or more (e.g., 3 or more) biomarkers selected from the group consisting of interleukin 6 (IL-6), interleukin 8 (IL-8), MCP-1, TNFα, GM-CSF, IFNγ, IL-1β, or a fragment thereof, in a sample obtained from the subject (e.g., ex vivo explant culture of a tissue biopsy) prior to the initiation of the treatment; determining the level of the one or more (e.g., 3 or more) biomarkers in a second sample(s) from the subject after at least a portion of the treatment has been administered; comparing the level of the one or more (e.g., 3 or more) biomarkers in the first sample(s) with a level of the one or more (e.g., 3 or more) biomarkers in the second sample(s), wherein a difference in the level of the one or more (e.g., 3 or more) biomarkers in the first sample(s) as compared to the level of the one or more (e.g., 3 or more) markers in the second sample(s) indicates that the subject is responding to the treatment. Under these embodiments, in one instance, the response indicates remission of the IBD. In another instance, the response indicates stabilization of the IBD.

IV. Method of Screening for Test Agents

Another aspect of the invention relates to a method for screening for an agent capable of influencing the outcome of a patient suffering from inflammatory bowel disease (IBD), comprising contacting a sample obtained from the patient (e.g., ex vivo explant culture of a tissue biopsy) with a test agent; and detecting the expression level of one or more (e.g., 3 or more) biomarkers selected from the group consisting of GM-CSF, IFNγ, IL-10, IL-12p70, IL-12p40, IL-1β, IL-2, IL-4, IL-5, IL-6, IL-7, IL-8, IL-13, IL-17A, MCP-1, and TNFα, or a fragment thereof, in a sample before and after contacting with the test agent; wherein an attenuation in the levels of the biomarker after contacting with the test agent compared to the levels of the biomarker before contacting with the test agent indicates that the test agent is capable of influencing the outcome of the patient suffering from IBD.

In one embodiment, the biomarker is selected from the group consisting of interleukin 17A (IL-17A), interleukin 7 (IL-7), interleukin 5 (IL-5), interleukin 4 (IL-4) and interleukin 13 (IL-13), or a fragment thereof. In another embodiment, the biomarker is IL-6 or IL-8, or a combination thereof.

In one embodiment, the screened agent is a TNFα inhibitor. Particularly preferably, the screened agent is an anti-TNFα antibody or a fragment thereof or a biosimilar thereof, e.g., a neutralizing or antagonizing anti-TNFα antibody or a fragment thereof. In another embodiment, the screened agent is a protein, peptide or aptamer that binds to TNFα and inhibits or prevents binding of TNFα to its receptor and/or effector molecule, e.g., TNFα-receptor I or TNFα-receptor II.

In another embodiment, the agent is an integrin anti-α4β7 antibody, e.g., vedolizumab. In another embodiment, the agent is janus kinase (JAK) inhibitor, e.g., tofacitinib. In yet another embodiment, the agent is an antibody that binds to interleukin 12 and/or interleukin 23, e.g., ustekinumab.

A representative method of screening for test agents is exemplified in Example 2.

V. Biomarkers

In one aspect, the present invention provides biomarkers. The term "biomarker" as used herein refers to an indicator of a phenotype of a patient, e.g., a pathological state or likely responsiveness to a therapeutic agent, which can be detected in a biological sample of the patient. Biomarkers include, but are not limited to, DNA, RNA, protein, carbohydrate, or glycolipid-based molecular markers.

In one embodiment, the biomarker is a "protein biomarker." The term protein includes any molecule containing a peptide bond, including, but not limited to, peptides, polypeptides, polyamino acids, proteins, etc., including fragments and variants thereof. Preferably, the protein biomarker is selected from the group consisting of granulocyte macrophage colony-stimulating factor (GM-CSF), interferon gamma (IFNγ), interleukin 10 (IL-10), interleukin 12 70-kDa (IL-12p70), interleukin 12 40-kDa (IL-12p40), interleukin 1 beta (IL-1β), interleukin 2 (IL-2), interleukin 4 (IL-4), interleukin 5 (IL-5), interleukin 6 (IL-6), interleukin 7 (IL-7), interleukin 8 (IL-8), interleukin 13 (IL-13), interleukin 17 (IL-17), monocyte chemoattractant protein-1 (MCP-1), and tumor necrosis factor alpha (TNFα), or a fragment thereof. Particularly preferably, the biomarker is selected from the group consisting of interleukin 17A (IL-17A), interleukin 7 (IL-7), interleukin 5 (IL-5), interleukin 4 (IL-4) and interleukin 13 (IL-13), or a fragment thereof.

In another embodiment, the biomarker is a "nucleic acid biomarker." The term nucleic acid includes any molecule containing a plurality of nucleotides, each of which contains a 5-carbon sugar, a phosphate group, and a nitrogenous base. The term includes, but is not limited to, DNA, RNA, artificial nucleic acids, including analogs thereof, etc., including fragments and variants thereof. Preferably, the nucleic acid biomarker is an mRNA (or cDNA) encoding a protein biomarker selected from the group consisting of GM-CSF, IFNγ, IL-10, IL-12p70, IL-12p40, IL-1β, IL-2, IL-4, IL-5, IL-6, IL-7, IL-8, IL-13, IL-17A, MCP-1, and TNFα, or a fragment thereof. Particularly preferably, the nucleic acid biomarker encodes a protein biomarker selected from the group consisting of IL-17A, IL-7, IL-5), IL-4, and IL-13, or a fragment thereof.

In another embodiment, the invention provides for the use of "signatures" or "profiles," comprising a single biomarker or a combination of 2, preferably 3, more preferably 4, particularly preferably 5 and most preferably 6 or more of the aforementioned biomarkers, or fragments thereof. Non-limiting examples of such signatures include, but are not limited to, for example, a signature comprising two biomarkers which are IL-17A and IL-7; a signature comprising three biomarkers which are IL-7, IL-5 and IL-4; a signature comprising four biomarkers which are IL-7, IL-5, IL-4 and IL-13; a signature comprising five biomarkers which are IL-17A, IL-7, IL-5, IL-4 and IL-13, etc.

In one embodiment, the instant invention relates to "proteomic signatures" containing at least 1, at least 2, at least 3, at least 4, at least 5, at least 6, at least 7 or more protein biomarkers selected from the group consisting of GM-CSF, IFNγ, IL-10, IL-12p70, IL-12p40, IL-1β, IL-2, IL-4, IL-5, IL-6, IL-7, IL-8, IL-13, IL-17A, MCP-1, and TNFα, or a fragment thereof. The proteomic signature may comprise cytokines with statistically significant reduction in expression in the supernatant from the ex vivo explant culture of the biopsy obtained from a IBD patient.

In another embodiment, the instant invention relates to "genetic signatures" containing at least 1, at least 2, at least 3, at least 4, at least 5, at least 6, at least 7 or more nucleic acid biomarkers selected from the group consisting of GM-CSF, IFNγ, IL-10, IL-12p70, IL-12p40, IL-1β, IL-2, IL-4, IL-5, IL-6, IL-7, IL-8, IL-13, IL-17A, MCP-1, and TNFα, or a fragment thereof. The genetic signature may comprise cytokines with statistically significant reduction in mRNA expression in cells of the ex vivo explant culture derived from the biopsy obtained from a IBD patient.

In another embodiment, the biomarker is selected from the group consisting of IL-6 and IL-8, or a fragment thereof.

A skilled artisan will appreciate that owing to the higher predictive power of a combination of biomarkers, the use of a combination of biomarkers (or signatures) such as ones described hereinbefore, are particularly preferred.

It is understood that one skilled in the art can utilize art-known techniques for obtaining the structural information of the various biomarkers of the present invention. For example, wherein the biomarker is a protein, such as, for example, GM-CSF, one skilled in the art can obtain the structural information of the protein/gene/RNA sequence of such biomarkers via the NCBI's website (available on the world-wide-web at ncbi(dot)nlm(dot)nih(dot)gov).

In order to purely facilitate the understanding, a skilled worker will appreciate that GM-CSF, as used herein, can relate to human or mouse orthologs of GM-CSF, such as, for example, human or mouse GM-CSF. Thus, in one embodiment, the GM-CSF is human GM-CSF (protein: NP_000749; mRNA: NM_000758). In another embodiment, the GM-CSF is mouse GM-CSF (protein: NP_034099; mRNA: NM_009969).

Similarly, IFNγ may relate to human IFNγ (protein: NP_000610; mRNA: NM_000619) or mouse IFNγ (protein: NP_03236; mRNA: NM_008337).

IL-10, as used herein, may relate to human IL-10 (mRNA: NM_000572; protein: NP_000563) or mouse IL-10 (mRNA: NM_010548; protein: NP_034678).

Likewise, IL-12p'70 refers to the active heterodimer cytokine encoded by two separate genes, IL-12A (p35) (mRNA human: NM_000882; mRNA mouse: NM_001159424; protein human: NP_000873; protein mouse: NP_001152896) and IL-12B (p40) (mRNA human: NM_002187; mRNA mouse: NM_001303244; protein human: NP_002178; protein mouse: NP_001290173).

Likewise, IL-1β, as used herein, may relate to human IL-1β (mRNA: NM_000576; protein: NP_000567) or mouse IL-1β (mRNA: NM_008361; protein: NP_032387).

IL-2, as used herein, may relate to human IL-2 (mRNA: NM_000586; protein: NP_000577.2) or mouse IL-2 (mRNA: NM_008366; protein: NP_032392.1).

IL-4, as used herein, may relate to human IL-4 (mRNA: NM_172348 and NM_000589; protein: NP_000580.1 and NP_758858.1) or mouse IL-4 (mRNA: NM_021283; protein: NP_067258.1).

IL-5, as used herein, may relate to human IL-5 (mRNA: NM_000879; protein: NP_000870.1) or mouse IL-5 (mRNA: NM_010558; protein: NP_034688.1).

IL-6, as used herein, may relate to human IL-6 (mRNA: NM_000600 and NM_001318095; protein: NP_000591.1) or mouse IL-6 (mRNA: NM_031168 and NM_001314054; protein: NP_112445.1 and NP_001300983.1).

IL-7, as used herein, may relate to human IL-7 (mRNA: NM_000880, NM_001199886, NM_001199887, or NM_001199888; protein: NP_000871.1, NP_001186815.1, NP_001186816.1, or NP_001186817.1) or mouse IL-7

(mRNA: NM_008371, NM_001313888, NM_001313889, or NM_001313890; protein: NP_032397.1).

IL-8, as used herein, may relate to human IL-8 (mRNA: NM_000584; protein: NP_000575.1). The mouse ortholog of IL-8 is unknown.

IL-13, as used herein, may relate to human IL-13 (mRNA: NM_002188; protein: NP_002179.2) or mouse IL-13 (mRNA: NM_008355; protein: NP_032381.1).

IL-17A, as used herein, may relate to human IL-17A (mRNA: NM_002190.2; protein: NP_002181.1) or mouse IL-17A (mRNA: NM_010552.3; protein: NP_034682.1).

MCP-1, as used herein, may relate to human MCP-1 (mRNA: NM_002982; protein: NP_002973.1) or mouse MCP-1 (mRNA: NM_011331; protein: NP_035461.2).

TNFα, as used herein, may relate to human TNFα (mRNA: NM_000594; protein: NP_000585) or mouse TNFα (mRNA: NM_001278601; protein: NP_001265530).

The aforementioned accession numbers are incorporated by reference herein in their entirety.

Fragments and variants of the aforementioned biomarkers are known in the art. For example, the UNIPROT database entry of each of the aforementioned biomarkers lists "natural variants," including structural relationship between the variant and the wild-type biomarker. Purely as representation, the human IL-1β protein (UNIPROT: P01584) includes a natural variant (VAR_073951) having E→N amino acid substitution at amino acid residue 141 of the putative human IL-1β protein sequence. Fragments, if known, are similarly listed under this section.

Embodiments of the instant invention further relate to an antibody arrays which comprises of a plurality of antibody molecules, each of which specifically binds to an antigenic compositions containing a plurality of the aforementioned biomarkers, or fragments thereof. A typical antibody array may comprise at least 2, at least 3, at least 4, at least 5, at least 6, at least 7, at least 8, at least 9, at least 10, at least 11, or more antibodies, each of which bind with specificity to the aforementioned biomarkers or fragments thereof.

The invention further comprises kits useful for the practice of one or more of the methods of the invention. In some preferred embodiments, a kit may contain one or more solid supports having attached thereto one or more of the aforementioned antibodies. The solid support may be a high-density antibody array. Kits may further comprise one or more reagents for use with the arrays, one or more signal detection and/or array-processing instruments, one or more protein databases and one or more analysis and database management software packages.

A "kit" is any manufacture (e.g. a package or container) comprising at least one reagent, e.g., a medicament for treatment of an IBD, e.g., UC or Crohn's disease, or a probe for specifically detecting a biomarker gene or protein of the invention. In certain embodiments, the manufacture is promoted, distributed, or sold as a unit for performing the methods of the present invention.

A "package insert" is used to refer to instructions customarily included in commercial packages of therapeutic products or medicaments, that contain information about the indications, usage, dosage, administration, contraindications, other therapeutic products to be combined with the packaged product, and/or warnings concerning the use of such therapeutic products or medicaments and the like.

In one embodiment, the instant invention relates to a biochip comprising a plurality of antibodies which specifically bind to the aforementioned polypeptides. Preferred biochips comprise at least 2, at least 3, at least 4, at least 5, at least 6, at least 7, at least 8, at least 9, or all of the proteins from the group consisting of GM-CSF, IFNγ, IL-10, IL-12p70, IL-12p40, IL-1β, IL-2, IL-4, IL-5, IL-6, IL-7, IL-8, IL-13, IL-17A, MCP-1, and TNFα, or a fragment thereof. A control antibody which specifically binds to a control protein, e.g., serum exosome protein, may also be employed.

The invention includes methods of using the databases, such as methods of using computer systems to present information identifying the expression level in a tissue or cell of at least two of the aforementioned proteins, comprising the step of comparing the expression level of at least one protein in the tumor tissue or cell to the level of expression of the protein in the database. In some preferred embodiments, the method is drawn to the detection of the expression level of one or more of GM-CSF, IFNγ, IL-10, IL-12p70, IL-12p40, IL-1β, IL-2, IL-4, IL-5, IL-6, IL-7, IL-8, IL-13, IL-17A, MCP-1, and TNFα, or a fragment thereof. A control antibody, e.g., an antibody binding to serum exosome protein, may be employed for comparative analysis. The skilled artisan is aware of the fact that many biological functions are accomplished by altering the expression of various proteins and/or activity thereof. For example, fundamental biological processes such as inflammation, are often characterized by the variations in the expression levels of groups of proteins involved in an ingenuity pathway. The instant invention therefore also relates to a method of ingenuity pathway analysis of a broad spectrum of IBD comprising detecting one or more proteins. For example, in the present invention there is provided a method for the grouping proteins into one or more signature profiles based on the expression level thereof, e.g., very high expression, moderate expression and low expression. A representative grouping is shown in FIG. 1 (described in detail in Example 1).

Oligonucleotides and Arrays Based Thereon

The invention comprises oligonucleotide arrays which are useful for the practice of one or more of the methods of the invention. Such arrays may contain an oligonucleotide which specifically hybridizes to a gene encoding GM-CSF, IFNγ, IL-10, IL-12p70, IL-12p40, IL-1β, IL-2, IL-4, IL-5, IL-6, IL-7, IL-8, IL-13, IL-17A, MCP-1, and TNFα, or a fragment thereof. A control oligonucleotide which specifically hybridizes to a gene encoding glyceraldehyde 3-phosphate dehydrogenase (GAPDH) may be optionally employed for comparative purposes.

The terms "array" or "matrix" refer to an arrangement of addressable locations or "addresses" on a device. The locations can be arranged in two-dimensional arrays, three-dimensional arrays, or other matrix formats. The number of locations may range from several to at least hundreds of thousands. Most importantly, each location represents a totally independent reaction site. A "nucleic acid array" refers to an array containing nucleic acid probes, such as oligonucleotides or larger portions of genes. The nucleic acid on the array is preferably single-stranded. Arrays wherein the probes are oligonucleotides are referred to as "oligonucleotide arrays" or "oligonucleotide chips." An "antibody array" refers to an array containing antibody molecules that are capable of binding to one or more antigens (i.e., proteins). A "microarray," also referred to herein as a "biochip" or "biological chip," is an array of regions having a density of discrete regions of at least about 100/cm$^2$, and preferably at least about 1000/cm$^2$. The regions in a microarray have typical dimensions, for example, diameters, in the range of between about 10-250 µm, and are separated from other regions in the array by about the same distance.

Preferably, such arrays may comprise a plurality of oligonucleotides which specifically hybridize to at least 2, at least 3, at least 4, at least 5 or at least 6, at least 7, at least 8, at least 9, or more of the aforementioned genes. Preferred methods may detect all or nearly all of the aforementioned genes. Any combination of genes may be employed, for example, a set of genes that are significantly down-regulated, e.g., IL-17A, IL-7, IL-5), IL-4, and IL-13, or a fragment thereof.

The invention also relates to primers and/or probes for measuring the level of expression of GM-CSF, IFNγ, IL-10, IL-12p70, IL-12p40, IL-1β, IL-2, IL-4, IL-5, IL-6, IL-7, IL-8, IL-13, IL-17A, MCP-1, and TNFα, or a fragment thereof in a sample. The primers and/or probes may be designed by using art known techniques based on the structural information (i.e., accession numbers). The genes can be measured by any method common in the art such as PCR, in situ hybridization, sequencing, etc.

The aforementioned protein and/or nucleic acid biomarkers may be detected using automated assay techniques. In one embodiment the biomarker levels are grouped as percentiles within or based on a set of patient samples, such as all patients with HCC. In such embodiments, a threshold level of expression is established wherein higher or lower levels of expression relative to, for instance, a particular percentile, is used as the basis for predicting outcome. The reference standard can also be defined by biomarker levels in a non-IBD population (for example, healthy subjects, or patients with other gastrointestinal disorders, but without IBD).

Biomarker Detection

In one embodiment the levels of biomarkers are measured using an antibody-based detection strategy (for example, enzyme-linked immuosorbent assay (ELISA), immunoblotting (WB) or immunohistochemistry (IHC)). However, the aforementioned method is not limited to antibody-based assays. Any method of detection of the expression of the gene and/or polypeptide products thereof can be reliably employed. Such method include, but are not limited to, for example, RT-PCR analysis, hybridization based analysis (i.e., Northern analysis), spectophotometry and/or proteomic analysis (i.e., mass spectral analysis). More sophisticated techniques for assaying for secondary modification of proteins (for example, phosphorylation, acetylation, farnesylation, etc.) and the effect thereof on the activity of such modified proteins are known in the art (for example, immunoblotting, yeast-2-hybrid assays, reporter-based assays, activity assays, etc.).

In one embodiment, the protein biomarkers are detected using routine immunoassays, e.g., multiplex ELISA assay (MILLIPLEX MAP Human Cytokine/Chemokine Magnetic Bead Panel; Millipore, Mass.). Signal detection and analysis may be performed using any routine luminescence, fluorescence, enzymatic and non-enzymatic assays, e.g., MAGPIX luminescence assays (Luminex Corporation, TX).

"Oligonucleotide," as used herein, refers to short, single stranded polynucleotides that are at least about seven nucleotides in length and less than about 250 nucleotides in length. Oligonucleotides may be synthetic. The terms "oligonucleotide" and "polynucleotide" are not mutually exclusive. The description above for polynucleotides is equally and fully applicable to oligonucleotides.

The term "primer" refers to a single stranded polynucleotide that is capable of hybridizing to a nucleic acid and allowing the polymerization of a complementary nucleic acid, generally by providing a free 3'-OH group.

The term "amplification" refers to the process of producing one or more copies of a reference nucleic acid sequence or its complement. Amplification may be linear or exponential (e.g., PCR). A "copy" does not necessarily mean perfect sequence complementarity or identity relative to the template sequence. For example, copies can include nucleotide analogs such as deoxyinosine, intentional sequence alterations (such as sequence alterations introduced through a primer comprising a sequence that is hybridizable, but not fully complementary, to the template), and/or sequence errors that occur during amplification.

The term "detection" includes any means of detecting, including direct and indirect detection.

"Elevated expression" or "elevated levels" refers to an increased expression of a mRNA or a protein in a patient relative to a control, such as an individual or individuals who are not suffering from an autoimmune disease, e.g., IBD, or relative to a pre-established threshold or cut-off value, or relative to the median for a population of patients and/or subjects.

"Low expression" or "low expression levels" refers to a decreased expression of a mRNA or a protein in a patient relative to a control, such as an individual or individuals who are not suffering from an autoimmune disease, e.g., IBD, or relative to a pre-established threshold or cut-off value, or relative to the median for a population of patients and/or subjects.

The term "multiplex-PCR" refers to a single PCR reaction carried out on nucleic acid obtained from a single source (e.g., a patient) using more than one primer set for the purpose of amplifying two or more DNA sequences in a single reaction.

This invention is further illustrated by the following examples which should not be construed as limiting. The entire contents of all references, patents and published patent applications cited throughout this application, as well as the Figures and the Sequence Listing, are hereby incorporated herein by reference.

VI. Apparatus

The automated processing and analysis of tissue samples can improve the speed, reliability and accuracy of diagnosis and evaluation of therapeutic options for a particular patient. Current methods have instruments that separately perform steps of the procedure that each require manual intervention to move samples being processed between stations. By eliminating manual steps in the process a substantial improvement in the efficacy of determining therapeutic options can be realized.

Figure 7:
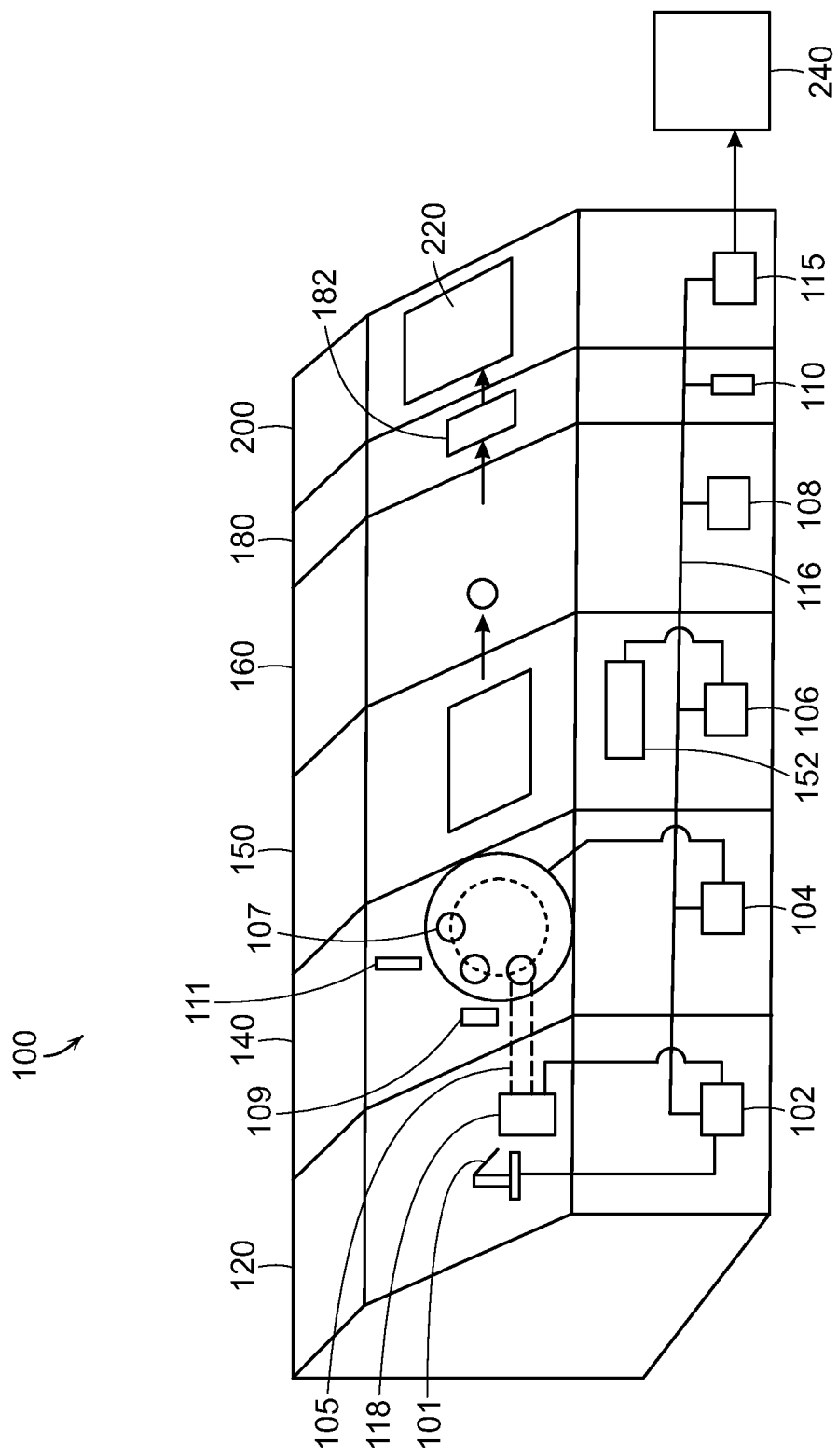
FIG. 7 schematically illustrates an automated system for sample processing and analysis in accordance with preferred embodiment

In preferred embodiments, the automated system 100 shown in FIG. 7 can include one or more system controllers 102 that operate the processing stages of the system. The system can be configured in a single housing or separate housing elements connected by channels enabling automated transport of samples. The one or more controllers 102-110 are connected to a central processor 115 using bus 116. The processor can be programmed to operate the stages in sequence for a given sample set. Samples can be translated through the system using disposable containers (e.g. vials, tissue culture dishes, etc) that are automatically replaced for transport of a different patient's samples. Other components, such as arrays of or multichannel pipettes used to transfer fluid samples between stations, can be cleaned (including change of pipette tips) before reuse.

The initial step involves retrieving a sample by biopsy or other tissue sampling process as described herein. The sample is situated on holder 118 is then processed and individual sample portions or slices are placed into wells to receive culture media. The initial processing can include a tissue cutter 120. Unlike existing tissue choppers such as the McIlwain system available form Warner Instruments, Hamden Conn., the present system has a translating stage with a blade 101 that operates in response to controller 102 which also operates a motorized track 105 to transport the sample slices or portions to a liquid dispenser 140. The sample portions are placed in individual wells 107 which can be arranged on a rotating assembly so the track can deliver individual sample portions to each well. A sensor 109 such as an optical sensor can detect the individual samples to trigger well movement. Other robotic delivery devices can also be used. A culture media can be automatically delivered to each well in precise volumes with one or more pipettes 111 or one or more other fluid delivery devices in response to controller 104. The wells can then be moved to an incubator 150 in which controller 106 operates heating and humidity system 152 for a programmed time period. Incubator systems such as the VWR air jacketed CO2 incubator employ temperature sensors to monitor conditions that can be used for feedback control.

Figure 6:
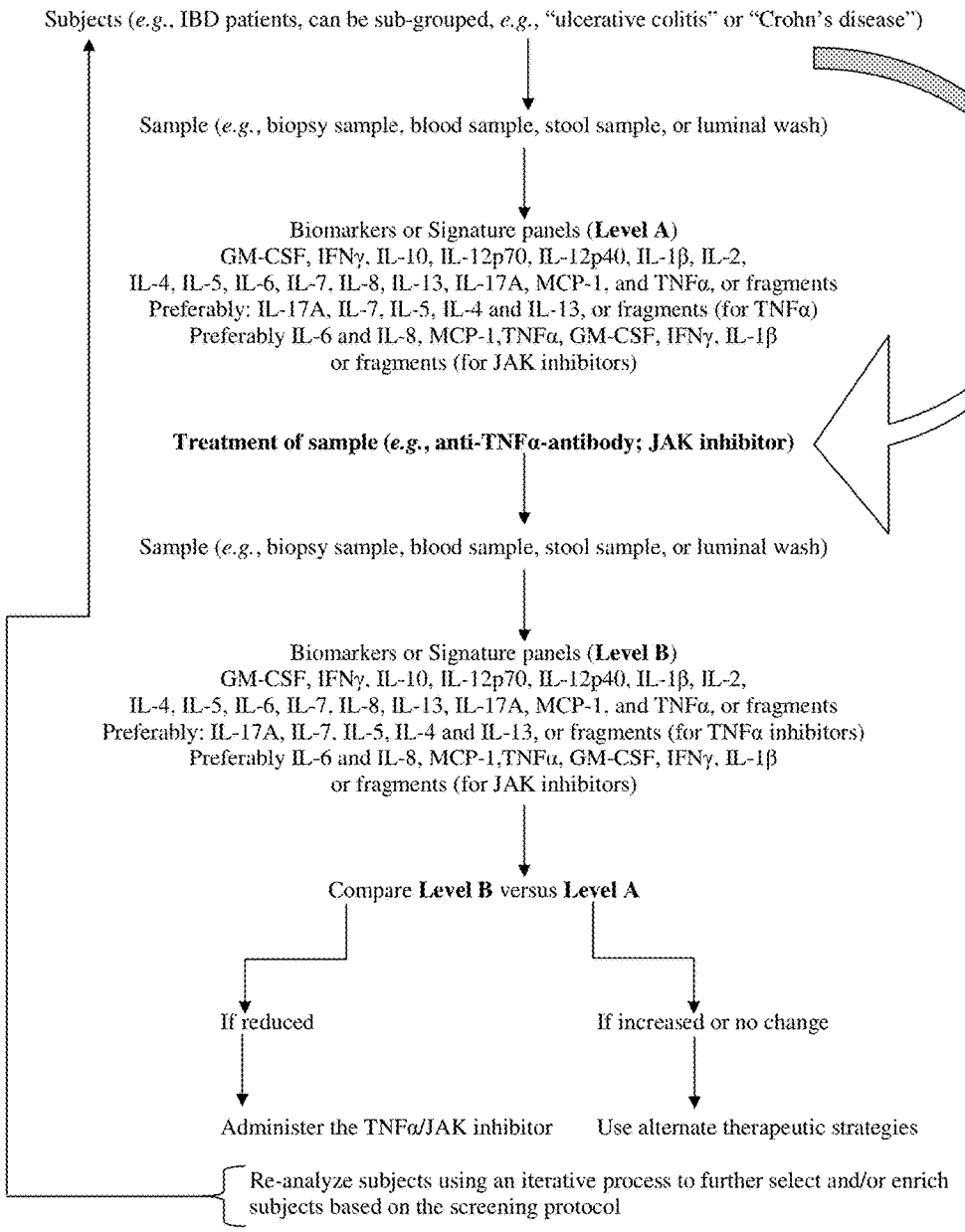
FIG. 6 shows a schematic chart outlining the various steps associated with an exemplary embodiment of the therapeutic and/or diagnostic methods of the instant invention. A similar strategy may be involved in screening for new test agents.
Figure 8:
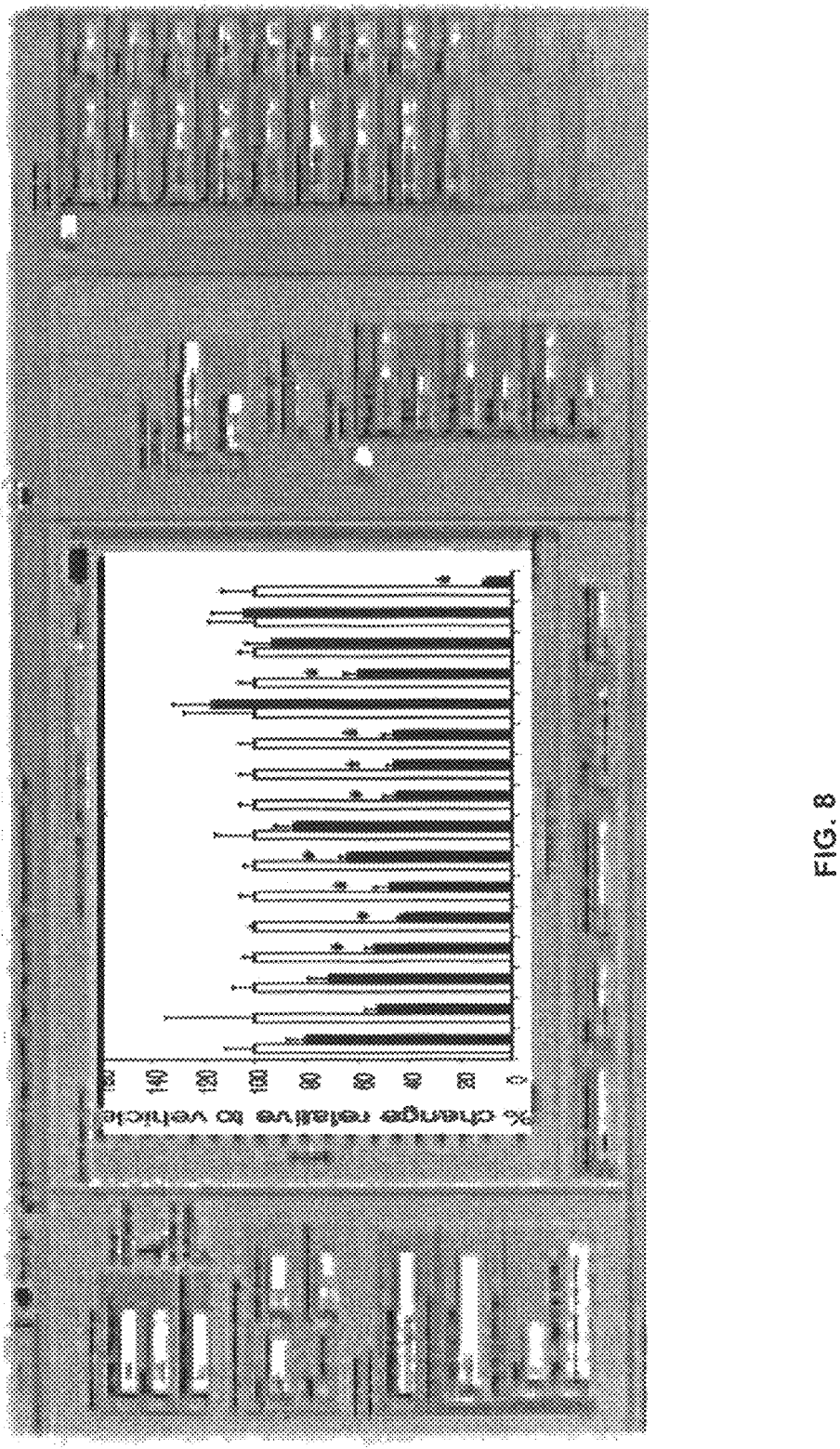
FIG. 8 illustrates a display screen for the processing system.

After the samples have been incubated, the wells are moved through assembly 160 so that the material (e.g., supernatant) from each well to be analyzed is isolated, prepared for immunoassay (e.g., removing cell/tissue debris by centrifugation or filtration), and delivered to analyzer 180. A microchannel plate 182 or cassette can be used to store all the processed sample portions for a particular patient. Systems using microchannel devices are available from Gyros AB of Uppsala, Sweden including the Gyros XPlore and Gryolal xP., and also from EMD Millipore Corporation, Billerica, Mass. Microfluidic devices are described in further detail in International Application No. PCT/SE02/01539 filed on Aug. 28, 2002, and PCT/GB99/00954, filed Mar. 19, 1999, now U.S. Pat. Nos. 8,030,062, and 9,376,658, for example, the entire contents of these patent and applications being incorporated herein by reference. The analyzer performs a multiplexed cytokine analysis as described herein to generate panels that are presented on display 220. A typical screen is shown in FIG. 8. The data processor 115 in processing system 200 with a plurality of memory devices can also be used to process the data as described previously herein and illustrated in FIG. 6, or the data can be sent via a network to an external processor 240 having a memory to store the data.

EXAMPLES

Example 1: Correlation of Therapeutic and Ex Vivo Responses to Anti-TNFα Therapy in Clinical Study Study Subjects Patients with established diagnosis of CD (N=29) or UC (N=16) of more than 6 month's duration were included in the study. Adult individuals (N=38) were recruited at the IBD Center of Beth Israel Deaconess Medical Center (BIDMC) and pediatric patients (N=7) at the IBD Center of Boston's Children's Hospital (BCH), both tertiary care institutions, during an 8-month period. Recruitment took place during a scheduled endoscopic procedure one day per week from the patient pool of three Gastroenterologists at BIDMC and one Gastroenterologist at BCH. Patients suspected or positive for *Clostridium difficile* or cytomegalovirus infection at the time of endoscopy were excluded from the study. For data analysis purposes, patients were grouped, after study enrollment, to two independent cohorts: Cohort 1 (N=23) consisted of patients naïve to exposure to anti-TNFα or other biologics at the time the biopsies were taken; about half of them (52%) were under treatment with steroids, immunomodulators (Azathioprine or 6-Mercaptopurine) or their combination. In Cohort 2 (N=22) were included patients under induction or maintenance therapy with anti-TNFα as well as patients with a history of anti-TNFα treatment, currently in remission or treated with the newest drugs for IBD (vedolizumab, tofacitinib, ustekinumab). For simplicity, the Harvey-Bradshaw index (HBI) was used for all patients to assess the clinical parameters of disease severity at the time of enrollment and a score (0-10) for each patient was provided by the treating physician. An HBI score<5 indicates clinical remission and 27.3% of patients in cohort 1 and 21.7% of patients in cohort 2 had HBI score≥5. Likewise, an endoscopy score (0-3) was assigned based on the findings during the endoscopic procedure and 41% of patients in cohort 1 and 52% of patients in cohort 2 had an endoscopy score≥2. The correlation coefficient R for HBI and endoscopic scores was 0.4 (p=0.006).

During a hospital visit for an endoscopic procedure that was part of their standard care, patients were asked by the study coordinator whether they were willing to participate in this research study and sign the informed consent approved by the Institution's Committee on Clinical Investigations. From each patient, four extra punch biopsies were taken from the macroscopically most diseased areas of the inflamed intestinal mucosa, put on ice and transferred to the lab within 30 minutes of their harvesting.

Culture of Intestinal Mucosal Explants

From each patient, intestinal mucosal biopsies were minced into several pieces and distributed in 8 wells of a 96-well plate in 250 µl of Dulbecco's Modified Eagle Medium (DMEM) supplemented with 10% FBS and anti-biotic-antimycotic (Life Technologies, CA). Half of the cultures were treated with infliximab (REMICADE®; 0.5 mg/ml; Janssen Biotech, Inc, NJ) and the plate was incubated at 37° C. in a humidified chamber of 95% $O_2$/5% $CO_2$ for 18 hours. Culture supernatants were collected, filtered and stored at −80° C. GM-CSF, IFNγ, IL-10, IL-12p'70, IL-12p40, IL-10, IL-2, IL-4, IL-5, IL-6, IL-7, IL-8, IL-13, IL-17, MCP-1 and TNFα levels were determined using a multiplex ELISA assay (MILLIPLEX® MAP Human Cytokine/Chemokine Magnetic Bead Panel; Millipore, Mass.) according to the manufacturer's instructions. Signal detection and analysis was performed by MAGPIX® (Luminex Corporation, TX).

Statistical Analysis

Within each patient, differences in cytokine release between control and infliximab-treated cultures (n=4 per group) were assessed by the Mann-Whitney test. Cytokine changes in patients with CD (N=29) or UC (N=16) were expressed as mean±SEM and evaluated by unpaired t-test followed by Bonferroni correction for multiple comparisons. In rate or percentage comparisons a chi-square test was applied. The non-parametric Mann-Whitney test was chosen for the rest of two-group analyses. The STATView 2.0 software (SAS Institute) was used for all tests with the exception of the Receiver Operating Characteristic (ROC) analysis for which STATA13 was used.

Findings

Treatment of Human Mucosal Explants with Anti-TNFα Releases Global Cytokine Responses The impact of anti-TNFα (infliximab) treatment was investigated in vitro using mucosal biopsy cultures derived from the most inflamed areas of the terminal ileum or colon of a total of 45 patients with IBD, 64% with CD and 36% with UC. At the time the biopsies were taken, 32 patients (71%) were receiving medications for their IBD and 16 of them were under an anti-TNFα regimen. The assay read-out consisted of a panel of 15 cytokines, chemokines and inflammatory mediators, and its design was based on previously reported biomarkers for CD and UC, on biomarkers that correlated with response to anti-TNFα treatment and on plausible TNF-alpha related biological mechanisms (Tracey et al., Rismo et al., Iskandar et al., *Transl Res* 159:313-325, 2012; Umehara et al., *Hepatogastroenterology* 53:879-882, 2006). For each patient and each cytokine, data were generated for the two conditions (plus/minus infliximab) using the median of 4 independent cultures.

Overall, based on their abundance, cytokines secreted in culture supernatants from mucosal explants at baseline could be grouped in three categories: cytokines with low levels of expression under the conditions tested, like IL-5 (0.6-11 pg/ml), IL-7 (0-37 pg/ml), IL-13 (0-41.5 pg/ml) and IL-2 (1.16-29.6 pg/ml)), intermediate levels of expression such as TNFα (1.3-113.4 pg/ml)), IL-17A (3.7-76.6 pg/ml), IL-1 beta (0.5-128 pg/ml)), IL-4 (3-147 pg/ml), IFNγ (3-131.7 pg/ml), IL-12p4 0(11.7-169.2 pg/ml), IL-12p70 (6.7-75.4 pg/ml), IL-10 (3.3-131.7 pg/ml) and GM-CSF (3.1-177.3 pg/ml)) and very high levels of expression (IL-6 (4.7-2194 pg/ml), MCP-1 (52.7-7051 pg/ml) and IL-8 (188-24107 pg/ml)) (FIG. 1). Cytokine levels tended to be higher in patients with CD, which might reflect the intestinal location from which the biopsy was taken (ileal versus colonic) (Table 1). IL-1β in particular, was at least a log lower in patients with UC. Hence, CD and UC patients were analyzed as separate groups for the effects of infliximab treatment in cytokine release as shown in FIG. 1.

The Th2 type cytokines IL-4, IL-5 and IL-13 are presumed to play a key role as effector cytokines in UC (Strober et al., *Gastroenterology* 140:1756-1767, 2011) and their secretion by CD explants as found in the present study could be explained by tissue injury caused by processing of the biopsy material. In a recent report IL-13 production by mucosal explants did not differ between CD and UC, while IL-4 and IL-5 were undetectable in both groups (Biancheri et al., *Eur J Immunol* 44:370-385, 2014). These discrepancies could be attributed to differences in the culture conditions (presence of serum, total volume of culture) and the assay used to measure cytokine levels.

TABLE 1

Demographics and Clinical Characteristics of IBD Patients Evaluated ex vivo

| Characteristic | Anti-TNFα naïve* | Anti-TNFα exposed* |
|---|---|---|
| N= | 23 | 22 |
| Gender M/F | 10/13 | 14/8 |
| Age | | |
| ≤16 | 7 | 0(0) |
| 17-40 | 9 | 10 |
| >41 | 7 | 12 |
| CD/UC | 9/14 | 20/2 |
| HBI score ≥5 | 7 | 4 |
| Biopsy location (L1, L2, L3) | 2, 4, 17 | 6, 10, 6 |
| Endoscopy score ≥2 | 10 | 11 |
| Concomitant Medication^ | | |
| Anti-TNFα | 0 | 10 |
| Steroids | 3 | 0 |
| AZA/6-MP | 5 | 1 |

TABLE 1-continued

Demographics and Clinical Characteristics of IBD Patients Evaluated ex vivo

| Characteristic | Anti-TNFα naïve* | Anti-TNFα exposed* |
|---|---|---|
| Anti-TNFα/Steroids | 0 | 3 |
| Anti-TNFα/AZA/6-MP | 0 | 3 |
| Steroids/AZA/6-MP | 4 | 0 |
| Other | 0 | 3 |

Continued variables are expressed as median and range (min-max) and categorical variables as percentages.
L1: ileum; L2: ileocolonic; L3: colon
HBI: Harvey-Bradshaw index;
^at the time the biopsy was taken Changes in TNFα levels served as a positive control for the assay, and TNFα was found to be robustly down-regulated by infliximab in all patients tested (p<0.0001), though variation in the degree of inhibition among patients was noted (FIG. 1). Compared to TNFα, the magnitude of infliximab-mediated inhibition of the rest of cytokines was relatively modest (<30%) and reached statistical significance for IL-2 (p<0.001), IL-12p40 (p<0.05) and IL-5 (p<0.05) in patients with CD and IL-1β (p<0.05) and IL-7 (p<0.05) in patients with UC (FIG. 1).

These results might suggest that high intergroup variability perhaps can mask the global effects of anti-TNFα on cytokine release. To further interrogate this possibility, we assessed each patient individually for the number of cytokines significantly down-regulated in the presence of infliximab. Within each subject, cytokine release inhibition in response to infliximab was evaluated by a non-parametric test (Mann-Whitney). Indeed, some patients appeared to be good responders and some not. The cytokine profile of a patient who demonstrated robust cytokine inhibition by the ex vivo challenge with infliximab and that of a patient who did not respond is presented in FIG. 2. The results of the quantitative analysis of the number of cytokines per patient, besides TNFα, that were significantly inhibited by infliximab ex vivo revealed a non-canonical distribution with one cluster of patients showing inhibition of 0 cytokines (minimum 0, maximum 12, median 2) (FIG. 3A). The median value was subsequently used as a cut-off and patients with down-regulation of 0-2 cytokines were considered non-responders ex vivo.

Figure 3B:
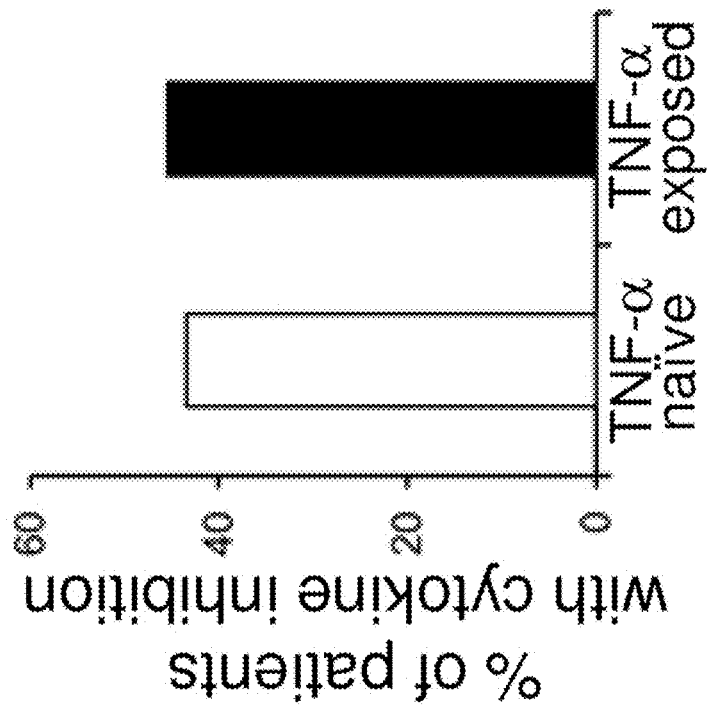
FIGS. 3A and 3B show the effects of ex vivo infliximab treatment on cytokine secretion. Mucosal biopsies from patients with IBD (N=46) were cultured for 18 hours in the presence of infliximab or media alone (4 replicas per condition). For each patient and each cytokine, differences in cytokine abundance in culture supernatants between control and infliximab-treated cultures were evaluated by a non-parametric test (Mann-Whitney).

In patient cohort 1 as described in table 1, which included anti-TNFα naïve IBD patients, the ex vivo response rate was 10/23 (45.5%); and in cohort 2 of anti-TNFα exposed patients was 10/22 (43.5%) (Fisher's exact p-value>0.9) (FIG. 3B). Notably, these response rates are quite comparable to those seen in IBD patients receiving anti-TNFα therapy (9, 11). These results at large might suggest that concomitant patient therapies, including anti-TNFα, do not interfere with the performance of the ex vivo test.

Correlation of Therapeutic and Ex Vivo Responses to Anti-TNFα Therapy

Upon study completion, a total of 28 patients (24 of cohort 2 and 5 from cohort 1) with IBD, 82% with CD, had received anti-TNFα therapy. Specifically, 18 patients were treated with infliximab, 8 patients with adalimumab, 1 patient with golimumab and 1 patient with cetrolizumab pegol. The study participants' hospital electronic records were reviewed by physicians blinded to the results of the ex vivo testing and clinical responses to treatment with anti-TNFα were assessed. The duration of clinical follow-up is summarized in Table 2.

TABLE 2

Two-by-two contingency table depicting
the prognostic properties of the subject testing

| TheRPA | Clinical Response | | Predictive Value |
|---|---|---|---|
| | Yes | No | |
| Positive | 10 | 2 | Positive: 83.3% |
| Negative | 1 | 15 | Negative: 93.8% |
| | Sensitivity | Specificity | |
| | 90.9% | 88.2% | |

Statistically significant inhibition of ≥3 cytokines in response to infliximab treatment ex vivo was used as a cut-off for predicting sustained clinical responses to anti-TNFα therapy. The assay had 9.1% (1/11) false positive and 11.8% (2/17) false negative results. Fisher's Exact p-value<0.0001.

Patients belonging to cohort 1 (N=6) came into the study as anti-TFNalpha naïve and had the shorter follow-up. Sixty one percent of patients (17 out of 28) failed to sustain clinical response to anti-TNFα treatment based on the following criteria adopted from previous studies (Atreya, 2014; Karmiris et al., *Gastroenterology* 137:1628-1640, 2009; Bortlik et al., *J Crohns Colitis* 7:736-743, 2013):

(a) need for hospitalization or surgical intervention for IBD-related problems (N=4);

(b) dose or frequency escalation of anti-TNFα treatment or switching to another anti-TNFα regimen (N=4);

(c) adding corticosteroids or an immunomodulator to the therapeutic scheme (N=3);

(d) treatment with emerging IBD drugs such as vedolizumab, tofacitinib, or ustekinumab (N=6).

Information about drug trough and anti-drug antibody levels were available in 5 of 17 non-responder patients and all of them had adequate drug levels in the absence of anti-drug antibodies.

Figure 4B:
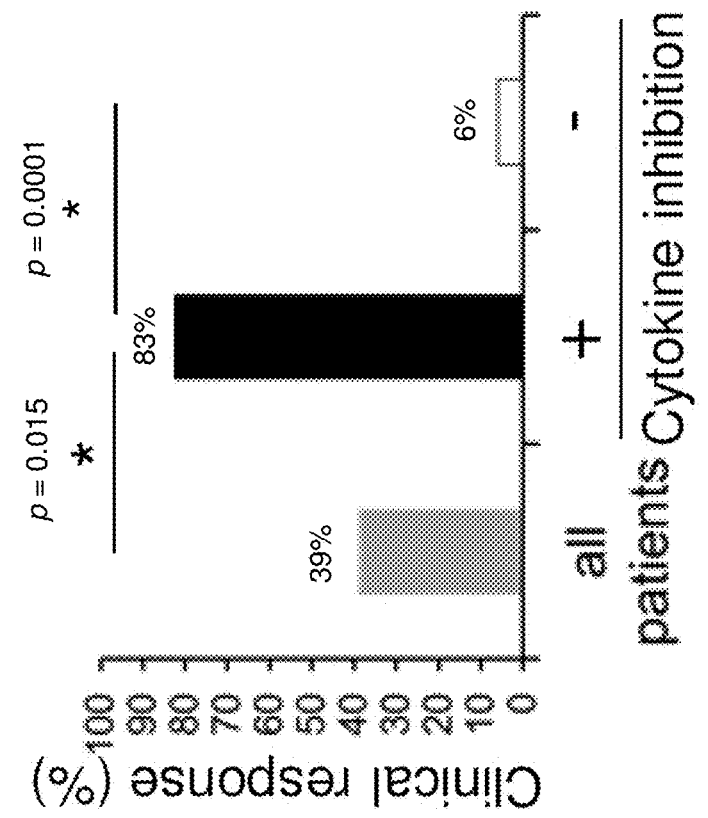
FIGS. 4A and 4B show bar charts displaying correlation between ex vivo response to anti-TNFα treatment and clinical response to anti-TNFα treatment in patients with IBD.
Figure 4A:
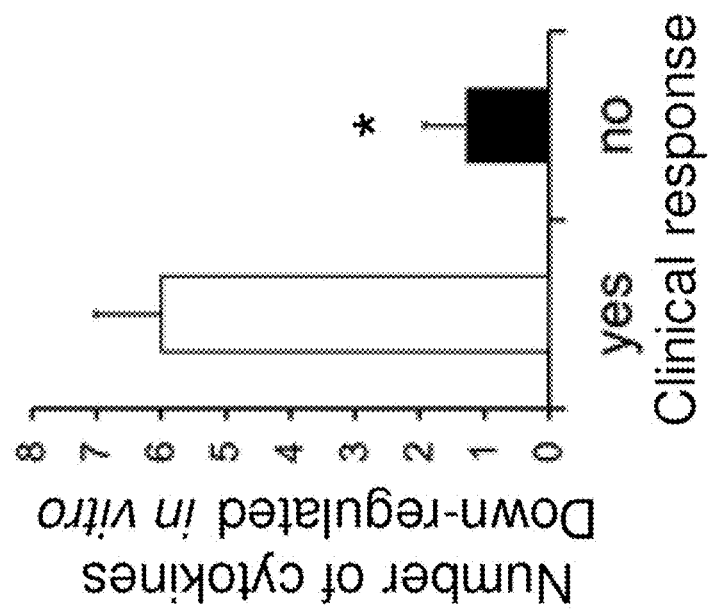

It was found that, as a group, clinical responders had a greater number of cytokines down-regulated in the ex vivo assay compared to non-responders (6.0±1.02 versus 1.29±0.63 respectively; p=0.0012 by a non-parametric test) (FIG. 4A).

Receiver Operating Characteristic (ROC) analysis was further used to evaluate the number of cytokines down-regulated per patient ex vivo as a predictor of clinical responses to anti-TNFα therapy. The area under the curve (AUC) was 0.869 (p=0.0011) (data not shown) and a cut-off value of >3 was associated with optimal sensitivity (90.91%) and specificity (88.24%) (Table 3). The positive and negative predictive values for the test were 83.3% and 93.8%, respectively.

While the overall clinical responses were 39% in this study, when patients were grouped according to the results of their ex vivo testing as described above, the clinical response rate was 83% for the sub-group of ex vivo responders (10/12) and 6% (1/16) for the ex vivo non-responders (p=0.015 between ungrouped patients and patients selected based on >3 cytokine responses in the ex vivo treatment with infliximab (FIG. 4B).

TABLE 3

Follow-up for IBD patients receiving anti-TNFα therapy

| | Responders N = 11 | Non-Responders N = 17 |
|---|---|---|
| Cohort 1 | | |
| 6-24 weeks | 2 | 4 |
| Cohort 2 | | |
| 6-24 weeks | 0 | 2 |
| 24-54 weeks | 2 | 6 |
| >54 weeks | 7 | 5 |

Patients were grouped according to their clinical outcome to responders and non-responders to anti-TNFalpha treatment.

Furthermore, it was found that the cytokines from the panel that were used for the ex vivo analysis were differentially down-regulated in clinical responders versus non-responders to anti-TNFα therapy. It was found that ex vivo inhibition by infliximab of IL-17A, IL-7, IL-5 and IL-4/IL-13 was almost exclusively observed in the clinical responders (Table 4).

TABLE 4

Cytokine inhibition by ex vivo infliximab treatment (according to clinical responses to anti-TNFα therapy in patients with IBD)

| Infliximab Treatment | Clinical Response | | | | |
|---|---|---|---|---|---|
| | Yes (n = 11) | | No (n = 17) | | |
| | N | % | N | % | p-value |
| GM-CSF | 1 | 9.1 | 1 | 5.9 | ns |
| IFNγ | 5 | 45.5 | 4 | 23.5 | ns |
| IL-10 | 2 | 18.2 | 2 | 11.8 | ns |
| IL-12p40 | 5 | 45.5 | 3 | 20.0^ | ns |
| IL-12p70 | 3 | 27.3 | 3 | 17.6 | ns |
| IL-13^ | 7 | 70.0 | 0 | 0.0^ | <0.001 |
| IL-17A^ | 8 | 72.7 | 0 | 0.0^ | <0.001 |
| IL-1β | 5 | 45.5 | 2 | 11.8 | ns |
| IL-2 | 5 | 45.5 | 2 | 11.8 | ns |
| IL-4 | 7 | 63.6 | 1 | 5.9 | <0.01 |
| IL-5^ | 9 | 81.8 | 1 | 7.7 | <0.001 |
| IL-6 | 0 | 0.0 | 1 | 5.9 | ns |
| IL-7^ | 8 | 88.8 | 0 | 0.0 | <0.001 |
| IL-8 | 0 | 0.0 | 1 | 5.9 | ns |
| MCP-1 | 1 | 9.1 | 1 | 5.9 | ns |

The absolute number of patients and the percentage are shown.
^In some patients values were below the assay's detection limit or missing.
ns: p-value >0.05 by Fisher's Exact test.

The involvement of the Th2 type cytokines (IL4 and IL-13) was totally unexpected since all clinical responders had CD, which is primarily a Th1/Th17 driven disease (Storber et al., 2011). Interestingly, the aforementioned findings are in line with a recent published report on the prognostic significance of inhibition of secreted IL-5 by infliximab by the patient's stimulated peripheral blood cells (Magnusson et al., *Aliment Pharmacol Ther* 41:1149-1161, 2015).

Example 2: Analysis of Cytokine Profiles in Response to Treatment with Various Agents Patients with IBD were treated with 0.5 mg/ml infliximab (an anti-TNFα antibody; therapeutic agent), 100 µM tofacitinib (a Janus kinase (JAK) inhibitor) and an experimental drug (at 10 µM concentration) in accordance with the protocol described above. Following treatment, biopsy samples were obtained and analyzed for cytokine profiles using standard ELISA assays. Results are shown in FIGS. 5A-5C. As shown in FIG. 5A, patients who respond to the anti-TNFα antibody infliximab displayed attenuation in the levels of many biomarkers, with reductions in the level of IL-12p40, IL-12p70, IL-13, IL-17A, IL-2, IL-4, IL-5, and IL-7 achieving statistical significance in the cytokine responder group compared to those in the non-responder group (TNFα levels were significantly attenuated in both groups).

Next, the cytokine profiles of patients treated with 100 µM tofacitinib (a JAK inhibitor which has been used in the treatment of ulcerative colitis; see NCT 00787202, Nov. 6, 2008) were analyzed. The results, as shown in FIG. 5B, demonstrate that levels of IL-6, IL-8, MCP-1, and TNFα were significantly attenuated in responders, whereas non-responders only showed attenuation in the levels of MCP-1 and TNFα. More surprisingly, the levels of IL-12p40, IL-12p70, IL-13, IL-17A, IL-2, IL-4, IL-5, and IL-7 were significantly elevated in the non-responder group (contrast with the cytokine profile of responders treated with the anti-TNFα antibody, which shows attenuation in the levels of these biomarkers). Lastly, the cytokine profiles of patients treated with 10 µM concentration of an experimental drug (ED) were analyzed. The results, as shown in FIG. 5C, demonstrate that, save for the observed elevation in IL-6 in the non-responder group, none of the biomarkers studied was modulated in response to the experimental drug, suggesting that this experimental drug will not be effective to treat this patient.

Additional similar experiments were conducted for different patients using the same or different therapeutic agents, and the results are shown in FIG. 5D-5H.

Figure 5D:
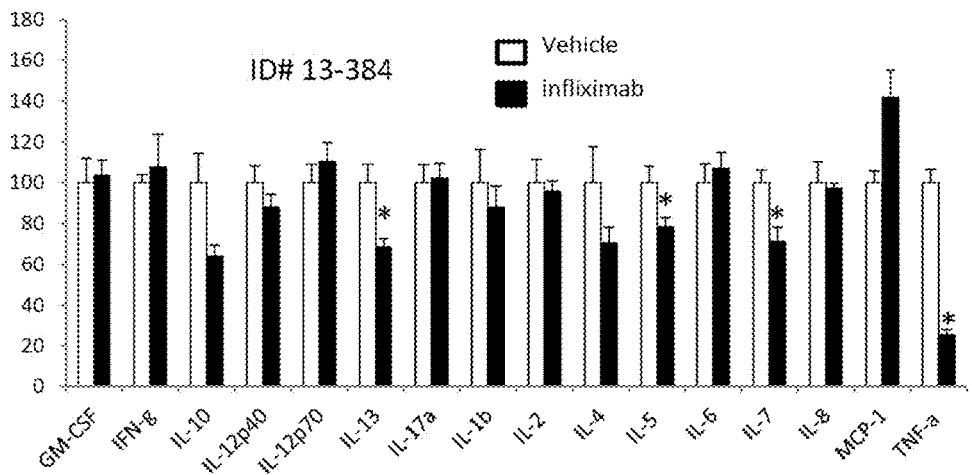

In particular, FIG. 5D shows changes in cytokine profiles of a patient (ID 13-284) treated with anti-TNFα antibody infliximab. The patient is an ex vivo responder with three cytokine expression down-regulation in addition to the direct target of infliximab—TNFα. This suggests that infliximab will be effective to treat this patient.

Figure 5E:
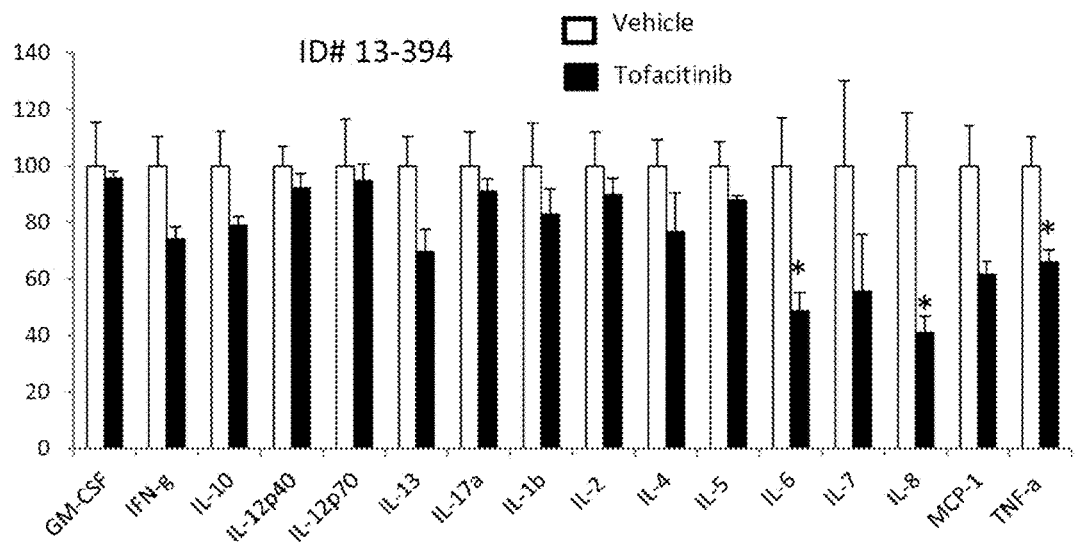
Figure 5F:
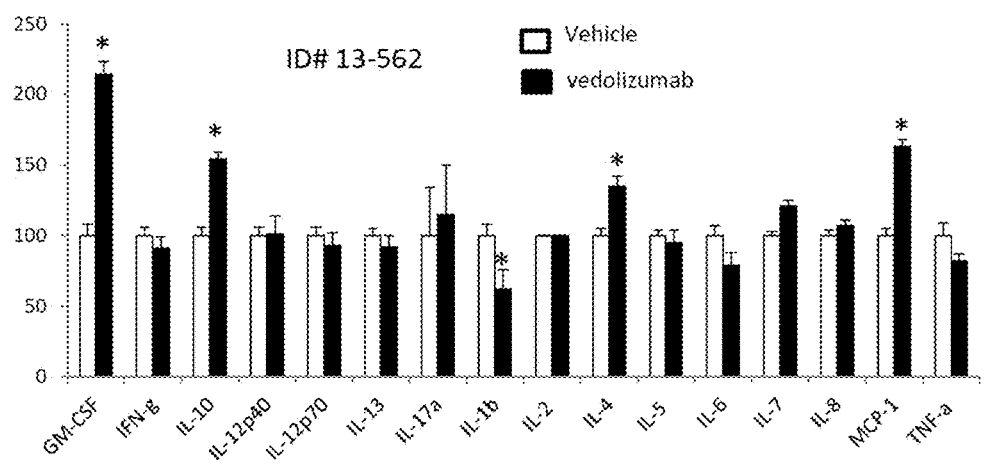

FIG. 5E shows changes in cytokine profiles of a patient (ID 13-394) treated with JAK inhibitor tofacitinib. The patient is an ex vivo responder with three cytokine expression down-regulation. This suggests that tofacitinib will be effective to treat this patient. FIG. 5F shows changes in cytokine profiles of a patient (ID 13-562) treated with anti-integrin antibody vedolizumab. The patient is an ex vivo non-responder with only one cytokine expression down-regulation and four cytokine expression up-regulation. This suggests that vedolizumab will not be effective to treat this patient.

Figure 5G:
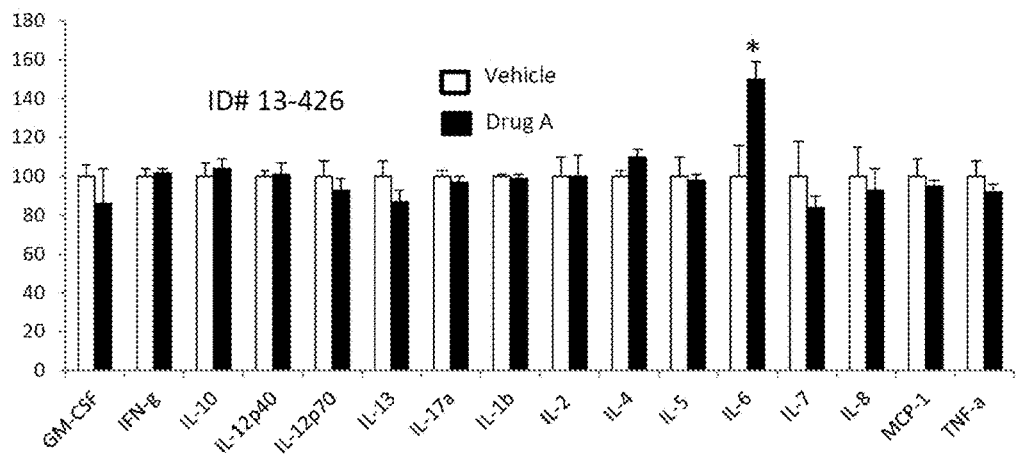

FIG. 5G shows changes in cytokine profiles of a patient (ID 13-426) treated with an experimental drug A, which is a small molecule G-protein coupled receptor (GPCR) antagonist. The patient is an ex vivo non-responder with one cytokine expression up-regulation. This suggests that drug A will not be effective to treat this patient.

Figure 5H:
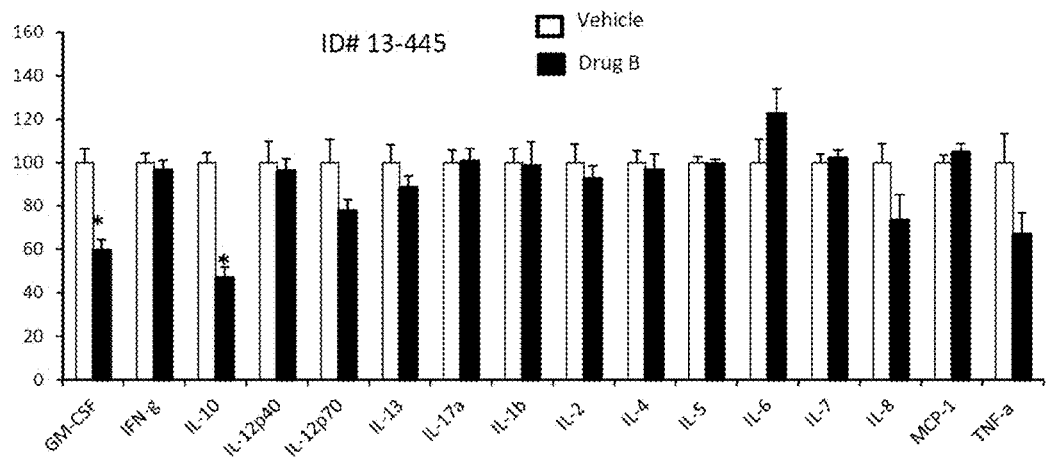

FIG. 5H shows changes in cytokine profiles of a patient (ID 13-445) treated with an experimental drug B, which is a small molecule protease inhibitor. The patient is an ex vivo non-responder with only two cytokine expression down-regulation. This suggests that drug B will not be effective to treat this patient.

Example 3: Exemplary Embodiment

The embodiment described herein is a non-limiting exemplary embodiment that illustrates certain aspects of the invention. While conditions described herein may be of general applicability and can be combined with any features or embodiments of the invention described herein elsewhere, the conditions should not be construed as limiting in any respect.

In certain embodiments, the method of the invention requires the use of patient samples, such as mucosal punch biopsies collected during an endoscopic procedure (e.g., colonoscopy or sigmoidoscopy). Preferably, the biopsies are obtained from an inflamed intestinal region of the patient, such as the macroscopically most inflamed region from the ileum, the ileocolonic region, or the colon of the patient.

The biopsy or biopsies are then placed in a suitable culture medium pre-cooled on ice, such as in a sterile plastic tube containing about 100 µL of media pre-cooled on ice. Ideally, the biopsy will be kept in this condition for no more than 30 minutes before being used in the next step.

The biopsy is then transferred, using sterile forceps, to the center of a tissue chopper receptacle with about 100 µL of ice cold culture media. Multiple punch mucosal biopsies can be transferred to the same drop of pre-cooled media, before a suitable tissue chopped is operated to cut the biopsy/biopsies to proper sizes for culturing.

Typically, the settings of the tissue chopper can be adjusted to create pieces of biopsies of suitable sizes for culturing. An exemplary set of tissue chopper parameters include: sectioning at 5-10 µm; 2 minutes vertical; 2 minutes horizontal; speed=2.

Once the tissue chopping is done, a suitable volume of media pre-warmed to 37° C. is added to the chopped pieces to collect the biopsy pieces. The container/dish containing the biopsy pieces can be slightly tilted (e.g., 45° C.) to facilitate the collection of the pieces.

As a general operating condition, about 1 mL of media can be added to each punch biopsy, resulting in a total volume of about 1.2 mL (including the 0.1 mL of cold media in which the biopsy is transported, and the 0.1 mL of pre-warmed media added after tissue chopping to facilitate collection). This 1.2 mL can be dispensed to 6 of the 96-well tissue culture plate, with about 200 µL in each well, for a total of 6 replica for each biopsy. The tissue culture plate preferably has flat bottom.

According to this setting, each biopsy can be used to create 6 individual cultures. A portion (e.g., 50%) of these individual cultures can be treated with one or more test compounds, while the remaining individual cultures can be treated with vehicle control. It is not necessary, and it is sometimes avoided, to subject all individual cultures derived from the same biopsy to the same treatment. In certain embodiments, random individual cultures, regardless of their origin, are treated by the same test compound, while the rest of the individual cultures are treated by vehicle control.

The rest of the empty wells in the tissue culture plate can optionally be filled with the same type of media.

The tissue culture plate is then incubated at 37° C. under cover and proper humidity (e.g., in a humidified chamber for tissue cultures), with 95% $O_2$/5% $CO_2$. A typical culture length is about 18 hours, but this can very depending on specific needs, such as 6 hrs, 8 hrs, 10 hrs, 12 hrs, 14 hrs, 16 hrs, 18 hrs, 20 hrs, 22 hrs, 24 hrs, or longer.

At the end of a pre-determined culture period, or at a time a sample is to be collected, about 50 µL of supernatant is drawn from each well without disrupting the tissue pellet. Such supernatant can be used for multiplex cytokine analysis. An additional 50 µL of supernatant may be collected from each well as back-up or can be stored at −20° C.

Multiplex cytokine analysis can then be performed using any suitable platform, such as microfluidic immunoassay chip or other related technology (e.g., Gyrolab XPLORE™)

The detection panel may include the following 16 cytokines that are disease-related (IBD-related): interleukin 17A (IL-17A), interleukin 7 (IL-7), interleukin 5 (IL-5), interleukin 4 (IL-4) and interleukin 13 (IL-13), granulocyte macrophage colony-stimulating factor (GM-CSF), interferon gamma (IFNγ), interleukin 10 (IL-10), interleukin 12 70-kDa (IL-12p70), interleukin 12 40-kDa (IL-12p40), interleukin 1 beta (IL-1β), interleukin 2 (IL-2), interleukin 6 (IL-6), interleukin 8 (IL-8), monocyte chemoattractant protein-1 (MCP-1), and tumor necrosis factor alpha (TNFα). The panel can be modified to include additional cytokines and pro-inflammatory mediators related to IBD, including IL-3, IL-9, IL-22, IL-23, IL-25, IL-35, IL-36, IL-37, TL1A, LIGHT and TGF-beta.

Data analysis is carried out to determine the cytokine levels in the culture supernatant of the individual cultures, based on standard curves, and are expressed as pg/ml. In case samples fall outside the detection range, they will be removed from the analysis. For each cytokine to be evaluated, at least 5 replicas are preferred. Within each patient, cytokine levels can be compared between vehicle- and drug-treated cultures using Mann-Whitney test.

Figure 2:
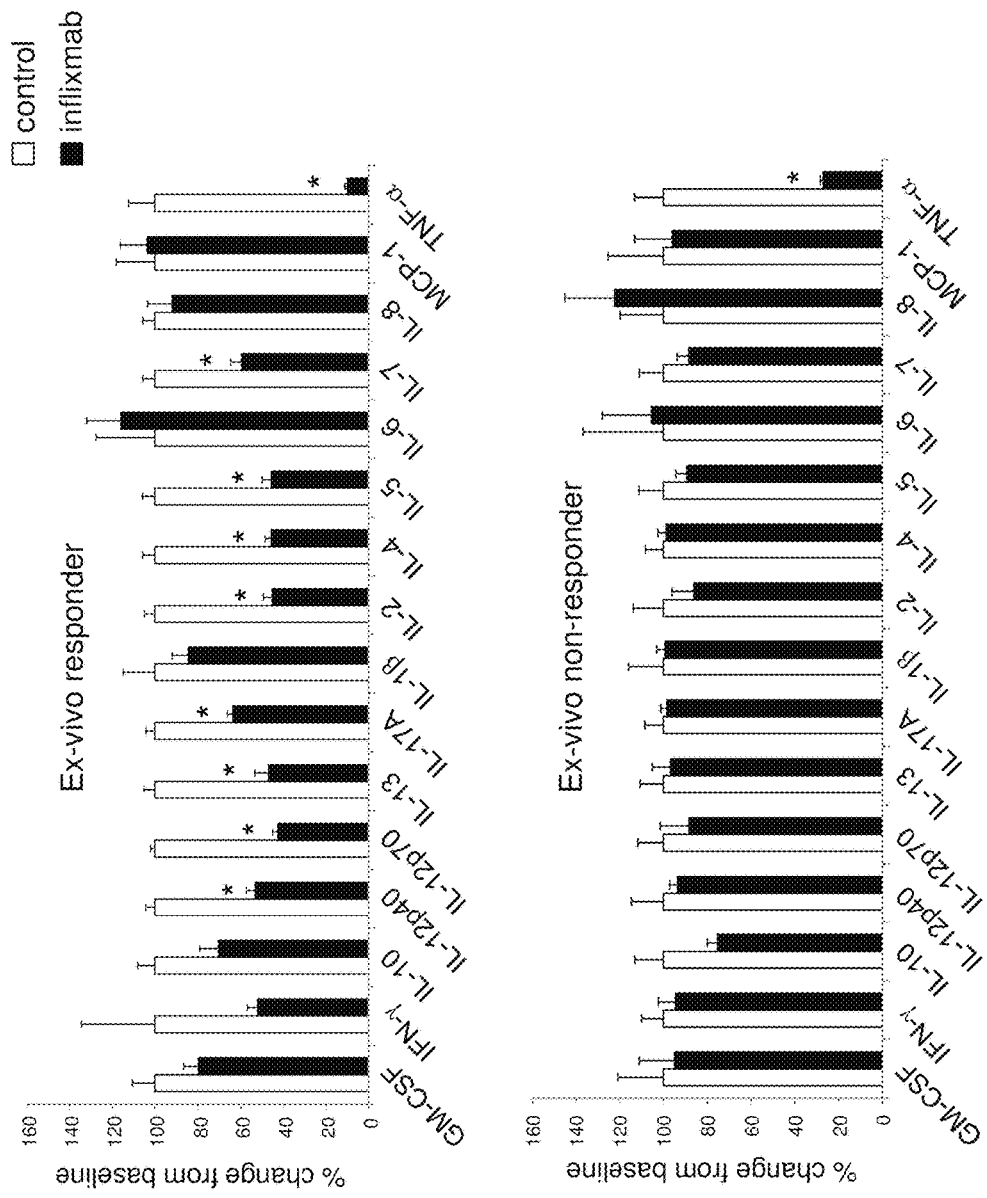
FIG. 2 shows bar charts displaying individual cytokine changes in response to infliximab treatment ex vivo. Cytokine changes in two representative patients—one responder (ID 1-278, upper panel) and one non-responder (ID 1-350, lower panel)—are shown. Cytokines were measured in culture supernatants of mucosal explants by multiplex ELISA. *p<0.05 by Mann-Whitney test compared to vehicle treated cultures.
Figure 3A:
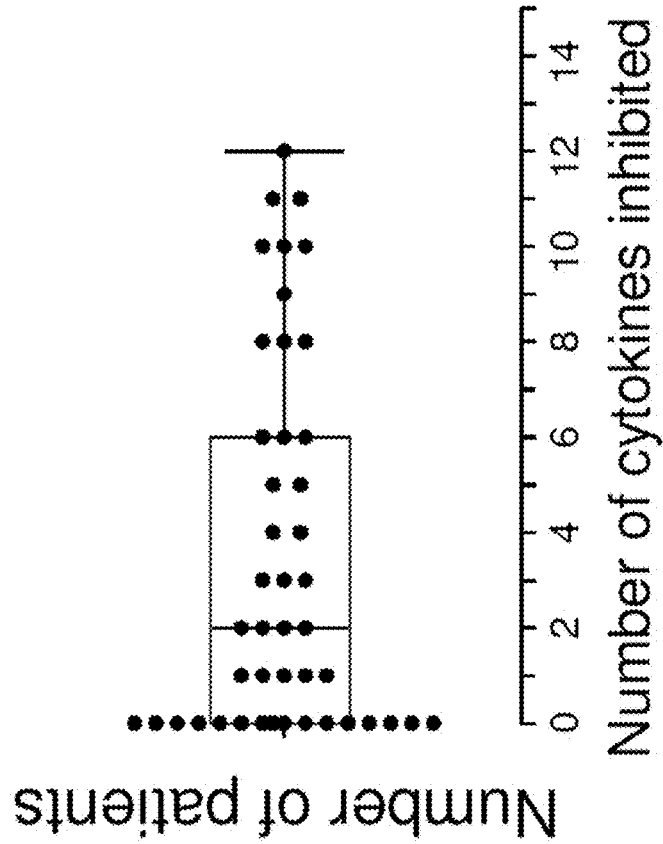

The results of this analysis can be presented in bar graphs as shown in FIG. 2. For each cytokine, cytokine concentration can be transformed—each is divided by the "mean or average" value of the vehicle-treated group, and multiplied by 100. Mean±standard error of the mean (SEM) values will be generated for vehicle- and drug-treated groups, and plotted in a graph as shown in FIG. 2.

Cytokines that are found to be inhibited at a level of statistical significance (e.g., p-value<0.05) based on the statistical test described above can be marked by a "*".

A patient with IBD will be considered to be "sensitive" to a treatment with the test drug or compound under investigation, if two or more cytokines are inhibited in addition to cytokine (s) that are direct targets of the drug (i.e., TNFα for infliximab; IL-12/IL-23 for ustekinumab). The system may also generate a print-out depicting those results.

A typical culture media suitable for use in the method of the invention is Dulbecco's Modified Eagle Medium (DMEM) supplemented with 10% FBS and antibiotic-antimycotic (Life Technologies, CA).

In certain embodiments, automated or semi-automated medical devices can be used to carry out one or more steps of the methods of the invention. Such medical devices may comprise a container or a dish that carries the biopsy material. The container may be functionally attached or connected to a tissue chopper that cuts/minces/chops/slices a collected biopsy (fresh or thawed), such that the cut/minced/chopped/sliced biopsy portions can be temporarily kept before further culturing. The container can be temperature-regulated, e.g., may be kept at a constant temperature of about 0-4° C.

EQUIVALENTS

Those skilled in the art will recognize, or be able to ascertain using no more than routine experimentation, many equivalents to the specific embodiments and methods described herein. Such equivalents are intended to be encompassed by the scope of the following claims.

What is claimed is:

1. A method of determining the number of cytokines, chemokines and inflammatory mediators exhibiting statistically significant down-regulation after contacting a candidate compound with a mucosal explant culture of a biopsy from a macroscopically diseased area of an inflamed intestinal mucosa from a subject having inflammatory bowel disease (IBD), the method comprising:
   (a) comparing the expression levels of a panel of cytokines, chemokines, and inflammatory mediators relating to IBD or treatment thereof, in the supernatant of a first mucosal explant culture and in the supernatant of a second mucosal explant culture; and,
   (b) determining the number of cytokines, chemokines and inflammatory mediators, from said panel of cytokines, chemokines, and inflammatory mediators, that exhibit statistically significant down-regulation in the second mucosal explant culture compared to the first mucosal explant culture;
wherein said first mucosal explant culture is produced from the biopsy in the absence of a candidate compound, and said second mucosal explant culture is produced from the biopsy in the presence of the candidate compound; and,
wherein said panel comprises, consists essentially of, or consists of: interleukin 17A (IL-17A), interleukin 7 (IL-7), interleukin 5 (IL-5), interleukin 4 (IL-4), interleukin 13 (IL-13), granulocyte macrophage colony-stimulating factor (GM-CSF), interferon gamma (IFNγ), interleukin 10 (IL-10), interleukin 12 70-kDa (IL-12p70), interleukin 12 40-kDa (IL-12p40), interleukin 1 beta (IL-1β), interleukin 2 (IL-2), interleukin 6 (IL-6), interleukin 8 (IL-8), monocyte chemoattractant protein-1 (MCP-1), and tumor necrosis factor alpha (TNFα), optionally further comprising, consisting essentially of, or consisting of one or more of: interleukin 3 (IL-3), interleukin 9 (IL-9), interleukin 22 (IL-22), interleukin 23 (IL-23), interleukin 25 (IL-25), interleukin 35 (IL-35), interleukin 36 (IL-36), interleukin 37 (IL-37), TNF-like ligand 1A (TL1A), LIGHT (Lymphotoxin-like Inducible protein that competes with Glycoprotein D for Herpesvirus entry on T cells) and Transforming Growth Factor-beta (TGF-beta).

2. A method of identifying a compound suitable for inflammatory bowel disease (IBD) treatment, the method comprising: using the method of claim 1, identifying, from a library of candidate compounds, a candidate compound that results in statistically significant down-regulation of: (1) three or more cytokines, chemokines and inflammatory mediators selected from the group consisting of: IL-12p40, IL-12p70, IL-13, IL-17A, IL-2, IL-4, IL-5, TNF-α, and IL-7; or (2) three or more cytokines, chemokines and inflammatory mediators selected from the group consisting of: IL-6, IL-8, TNF-α, and MCP-1, thereby identifying the compound suitable for inflammatory bowel disease (IBD) treatment.

3. A method of selecting two or more compounds for combination therapy for inflammatory bowel disease (IBD) treatment in a subject, the method comprising:
   (a) using the method of claim 1, identifying a first candidate compound resulting in statistically significant down-regulation of a first subset of three or more of cytokines, chemokines and inflammatory mediators selected from the group consisting of: IL-12p40, IL-12p70, IL-13, IL-17A, IL-2, IL-4, IL-5, TNF-α, and IL-7; or selected from the group consisting of: IL-6, IL-8, TNF-α, and MCP-1;
   (b) using the method of claim 1, identifying a second candidate compound resulting in statistically significant down-regulation of a second subset of three or more of cytokines, chemokines and inflammatory mediators selected from the group consisting of:

IL-12p40, IL-12p70, IL-13, IL-17A, IL-2, IL-4, IL-5, TNF-α, and IL-7; or selected from the group consisting of: IL-6, IL-8, TNF-α, and MCP-1;

(c) administering an effective amount of the first candidate compound and an effective amount of the second candidate compound to the subject for combination therapy, when said first subset and said second subset of three or more of said cytokines, chemokines and inflammatory mediators are completely different, or have no more than 1 or 2 overlap.

4. A method of diagnosing and treating inflammatory bowel disease (IBD) in a subject, the method comprising:
(a) comparing the expression levels of a panel of cytokines, chemokines, and inflammatory mediators selected from the group consisting of: IL-12p40, IL-12p70, IL-13, IL-17A, IL-2, IL-4, IL-5, IL-7, IL-6, IL-8, TNF-α, and MCP-1, in the supernatant of a first mucosal explant culture and in the supernatant of a second mucosal explant culture, wherein said first mucosal explant culture is produced from a biopsy from a macroscopically diseased area of an inflamed intestinal mucosa from the subject in the absence of a candidate compound, and said second mucosal explant culture is produced from the biopsy in the presence of the candidate compound;
(b) diagnosing the subject as being suitable for IBD treatment using the candidate compound, when three or more cytokines, chemokines, and inflammatory mediators, or two or more cytokines, chemokines, and inflammatory mediators that are not a direct target of the candidate compound, from said panel exhibit statistically significant down-regulation after contacting the candidate compound with the second mucosal explant culture, and,
(c) administering an effective amount of the candidate compound to the subject diagnosed in step (b) as being suitable for IBD treatment using the candidate compound,
thereby diagnosing and treating IBD in said subject.

5. The method of claim 4, wherein the IBD is selected from the group consisting of: ulcerative colitis (UC), Crohn's disease (CD), collagenous colitis, and lymphocytic colitis.

6. The method of claim 4, wherein said three or more cytokines, chemokines, and inflammatory mediators, or said two or more cytokines, chemokines, and inflammatory mediators that are not the direct target of the candidate compound, comprise, consist essentially of, or consist of: (1) IL-12p40, IL-12p70, IL-13, IL-17A, IL-2, IL-4, IL-5, and/or IL-7, or (2) IL-6, IL-8, and/or MCP-1.

7. The method of claim 4, wherein said three or more cytokines, chemokines, and inflammatory mediators are at least 5, 6, or 7 cytokines.

8. The method of claim 4, wherein said compound is a JAK (Janus Kinase) inhibitor, and wherein step (b) comprises diagnosing the subject as being suitable for IBD treatment using said JAK inhibitor, when at least one cytokine, chemokine, and inflammatory mediator from a panel of cytokines, chemokines, and inflammatory mediators selected from the group consisting of: IL-6, IL-8, TNF-α, and MCP-1, exhibit statistically significant down-regulation after contacting said JAK inhibitor with said second mucosal explant culture.

9. The method of claim 4, wherein said compound is a TNFα inhibitor and wherein step (b) comprises diagnosing the subject as being suitable for IBD treatment using said TNFα inhibitor, when three or more cytokines, chemokines, and inflammatory mediators, or two or more cytokines, chemokines, and inflammatory mediators that are not a direct target of said TNFα inhibitor, from a panel of cytokines, chemokines, and inflammatory mediators selected from the group consisting of: IL-12p40, IL-12p70, IL-13, IL-17A, IL-2, IL-4, IL-5, TNF-α, and IL-7, exhibit statistically significant down-regulation after contacting said TNFα inhibitor with said second mucosal explant culture.

10. The method of claim 4, wherein expression levels of said panel of cytokines, chemokines, and inflammatory mediators are determined using an assay selected from the group consisting of: enzyme-linked immuosorbent assay (ELISA), mass spectrometry (MS), immunoblotting (WB), and immunohistochemistry (IHC).

11. The method of claim 4, wherein the subject is a treatment-naïve subject who has not previously undergone therapy for IBD with a biological agent.

12. The method of claim 4, wherein the biopsy is obtained through an endoscopic procedure.

13. The method of claim 4, wherein the biopsy is obtained from the macroscopically most diseased area(s) of the inflamed intestinal mucosa.

14. The method of claim 4, wherein the biopsy is obtained from terminal ileum, ileocolonic region, or colon of the subject.

15. The method of claim 4, wherein the biopsy and the explant culture thereof comprise a mixture of different intestinal cell types including epithelial cells, immune cells, and stroma cells.

16. The method of claim 4, wherein the biopsy and the explant culture thereof are not stimulated or activated with an exogenous factor to promote cytokine secretion.

17. The method of claim 4, wherein the first and second explant cultures are maintained at about 37° C. for about 18 hrs in a humidified chamber with 95% $O_2$/5% $CO_2$.

18. The method of claim 4, wherein the first and second explant cultures each comprises 4, 5, or 6 replicas.

19. The method of claim 4, wherein statistical significance ($p<0.05$) is established based on the Mann-Whitney test.

20. A method of selecting a patient population with inflammatory bowel disease (IBD) which is sensitive to treatment using a compound, the method comprising:
(a) comparing the expression levels of a panel of cytokines, chemokines, and inflammatory mediators selected from the group consisting of: IL-12p40, IL-12p70, IL-13, IL-17A, IL-2, IL-4, IL-5, IL-7, IL-6, IL-8, TNF-α, and MCP-1, in the supernatant of a first mucosal explant culture and in the supernatant of a second mucosal explant culture, wherein said first mucosal explant culture is produced from a biopsy from a macroscopically diseased area of an inflamed intestinal mucosa from a subject who is a candidate for IBD treatment, in the absence of the candidate compound, and said second mucosal explant culture is produced from the biopsy in the presence of the candidate compound;
(b) selecting the subject as being suitable for IBD treatment using the compound, when three or more cytokines, chemokines, and inflammatory mediators, or two or more cytokines, chemokines, and inflammatory mediators that are not a direct target of the candidate compound, from said panel exhibit statistically significant down-regulation after contacting the compound with the second mucosal explant culture; and,
(c) repeating steps (a)-(b) for a different subject from a plurality of patients that are candidates for IBD treatment, until a pre-determined number of subjects is selected as being suitable for IBD treatment using the compound.

* * * * *